US012642537B2

(12) United States Patent
Moore et al.

(10) Patent No.: US 12,642,537 B2
(45) Date of Patent: Jun. 2, 2026

(54) SURGICAL GUIDES AND METHODS OF MANUFACTURE AND USE

(71) Applicant: WRIGHT MEDICAL TECHNOLOGY, INC., Memphis, TN (US)

(72) Inventors: Jesse G. Moore, Germantown, TN (US); Julia C. Alspaugh, Memphis, TN (US); David G. Reynolds, Fairport, NY (US); Paul M. Stemniski, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 691 days.

(21) Appl. No.: 17/663,730

(22) Filed: May 17, 2022

(65) Prior Publication Data

US 2022/0370081 A1 Nov. 24, 2022

Related U.S. Application Data

(60) Provisional application No. 63/223,224, filed on Jul. 19, 2021, provisional application No. 63/201,950, filed on May 20, 2021.

(51) Int. Cl.
*A61B 17/15* (2006.01)
*A61B 34/10* (2016.01)
(Continued)

(52) U.S. Cl.
CPC .......... *A61B 17/151* (2013.01); *A61B 17/157* (2013.01); *A61B 34/10* (2016.02);
(Continued)

(58) Field of Classification Search
CPC ..... A61B 17/151; A61B 17/157; A61B 34/10; A61B 2034/104; A61B 2034/108;
(Continued)

(56) References Cited

U.S. PATENT DOCUMENTS

| 9,089,342 B2 | 7/2015 | Carroll et al. |
| 9,402,640 B2 | 8/2016 | Reynolds et al. |

(Continued)

FOREIGN PATENT DOCUMENTS

| WO | 2015185865 A1 | 12/2015 |
| WO | 2020239909 A2 | 12/2020 |

OTHER PUBLICATIONS

Extended European Search Report issued in connection with European Patent Application No. 22174367.7, Oct. 17, 2022, 9 pages.

*Primary Examiner* — Sameh R Boles
(74) *Attorney, Agent, or Firm* — DUANE MORRIS LLP

(57) ABSTRACT

Medical devices may include a patient-engaging section and an instrument-engaging section positioned on a body of the device and the methods of forming such devices. Medical devices described herein may include resection guides, resection guide locators, and/or instruments for use in surgical methods. Devices described herein may have sections that are complementary to a natural anatomical surface of a target area of bone of a predetermined patient. In some instances, a resection guide and resection guide locator may have portions configured to couple the resection guide to the resection guide locator. Resection guides and/or resection guide locators may include openings for receiving an instrument or tool during an operation on the predetermined patient target area of bone.

9 Claims, 73 Drawing Sheets

(51) Int. Cl.
　　*A61B 17/00*　　　　(2006.01)
　　*A61B 17/56*　　　　(2006.01)
(52) U.S. Cl.
　　CPC ................. *A61B 2017/0023* (2013.01); *A61B 2017/00526* (2013.01); *A61B 2017/568* (2013.01); *A61B 2034/104* (2016.02); *A61B 2034/108* (2016.02)
(58) Field of Classification Search
　　CPC .. A61B 2017/0023; A61B 2017/00526; A61B 2017/568
　　See application file for complete search history.

(56)　　　　　　　　References Cited

U.S. PATENT DOCUMENTS

| | | | |
|---|---|---|---|
| 10,675,096 B2 * | 6/2020 | Utz | ...................... A61B 17/157 |
| 2012/0239045 A1 | 9/2012 | Li | |
| 2012/0317080 A1 | 12/2012 | Van Lierde et al. | |
| 2015/0374388 A1 | 12/2015 | Aram et al. | |
| 2018/0185033 A1 * | 7/2018 | Fritzinger | .......... A61B 17/1764 |
| 2019/0254681 A1 * | 8/2019 | Couture | ............... A61B 17/157 |
| 2021/0113222 A1 | 4/2021 | Khatibi et al. | |

\* cited by examiner

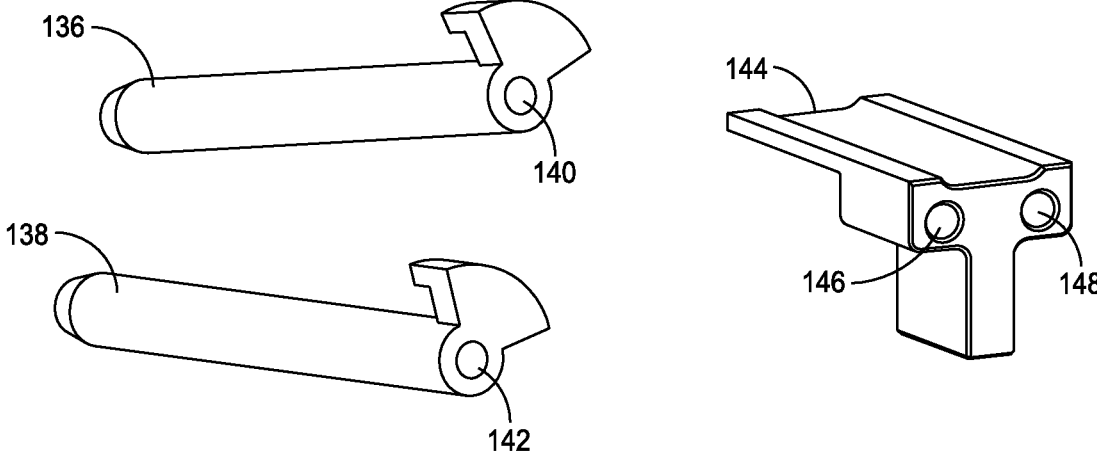
FIG. 22A
FIG. 22C
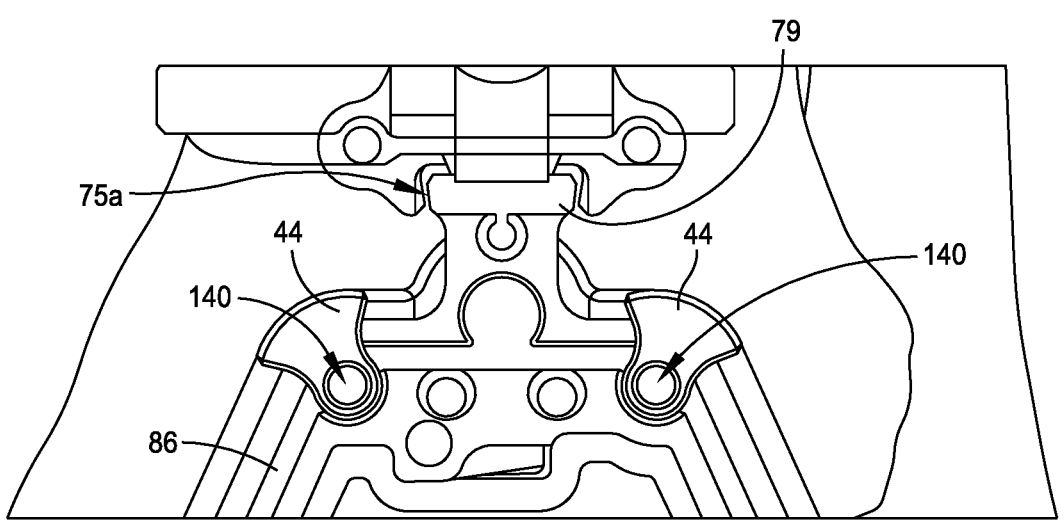
FIG. 22B

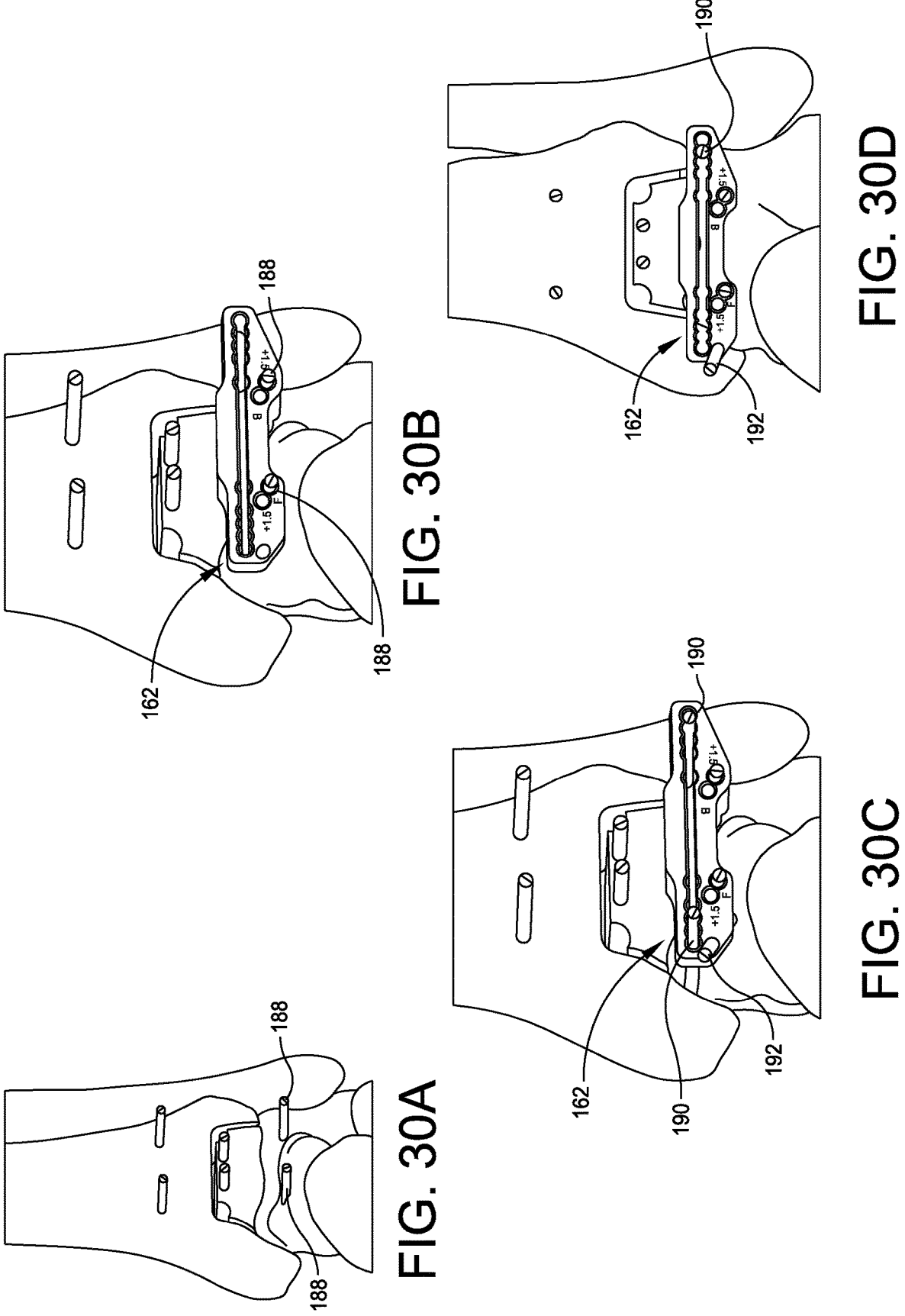

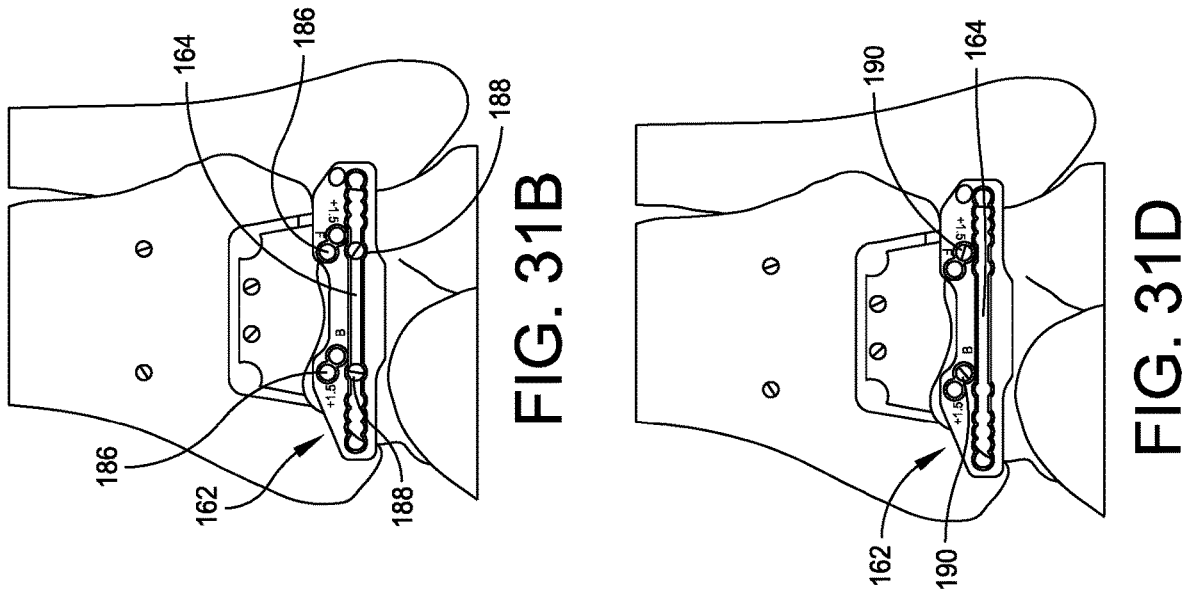
FIG. 31B
FIG. 31A
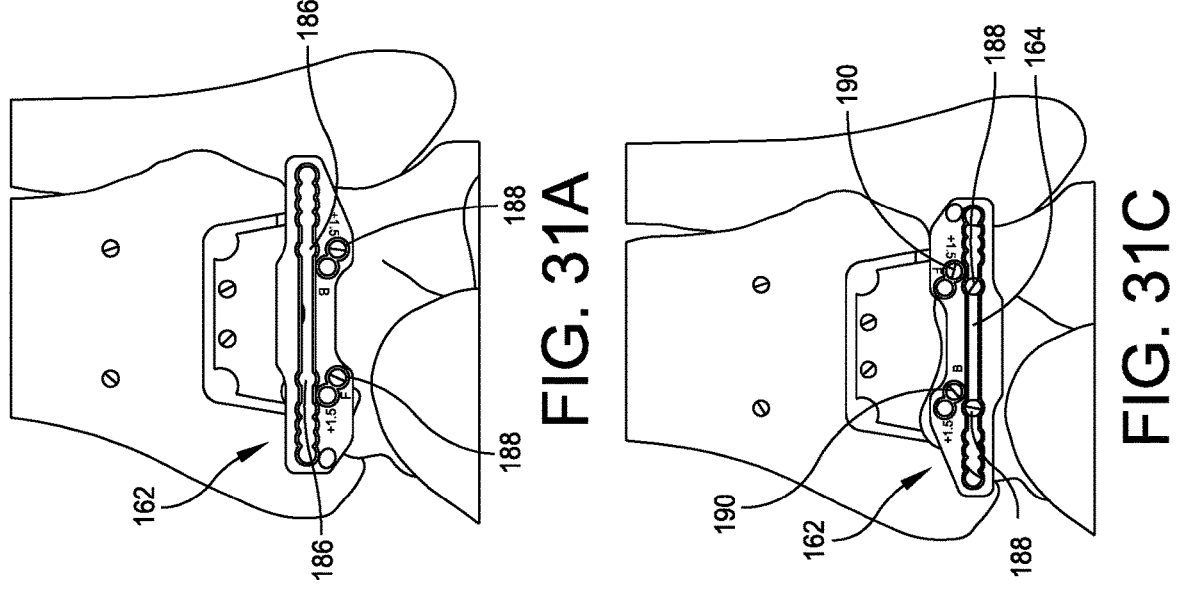
FIG. 31D
FIG. 31C

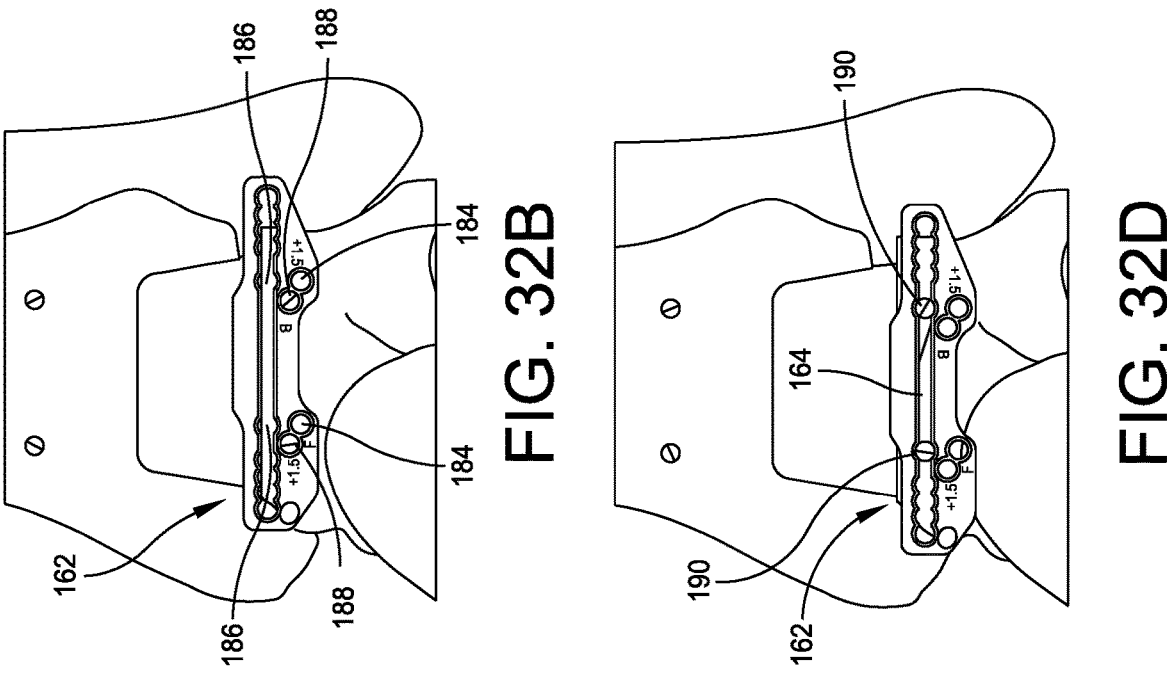
FIG. 32A
FIG. 32B
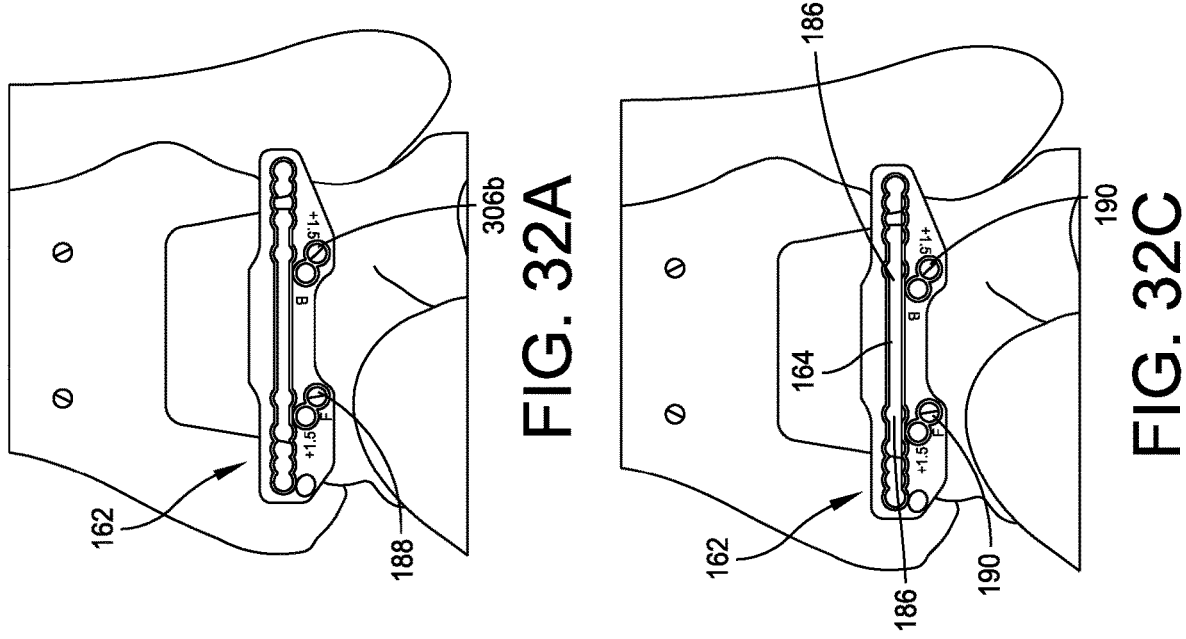
FIG. 32C
FIG. 32D

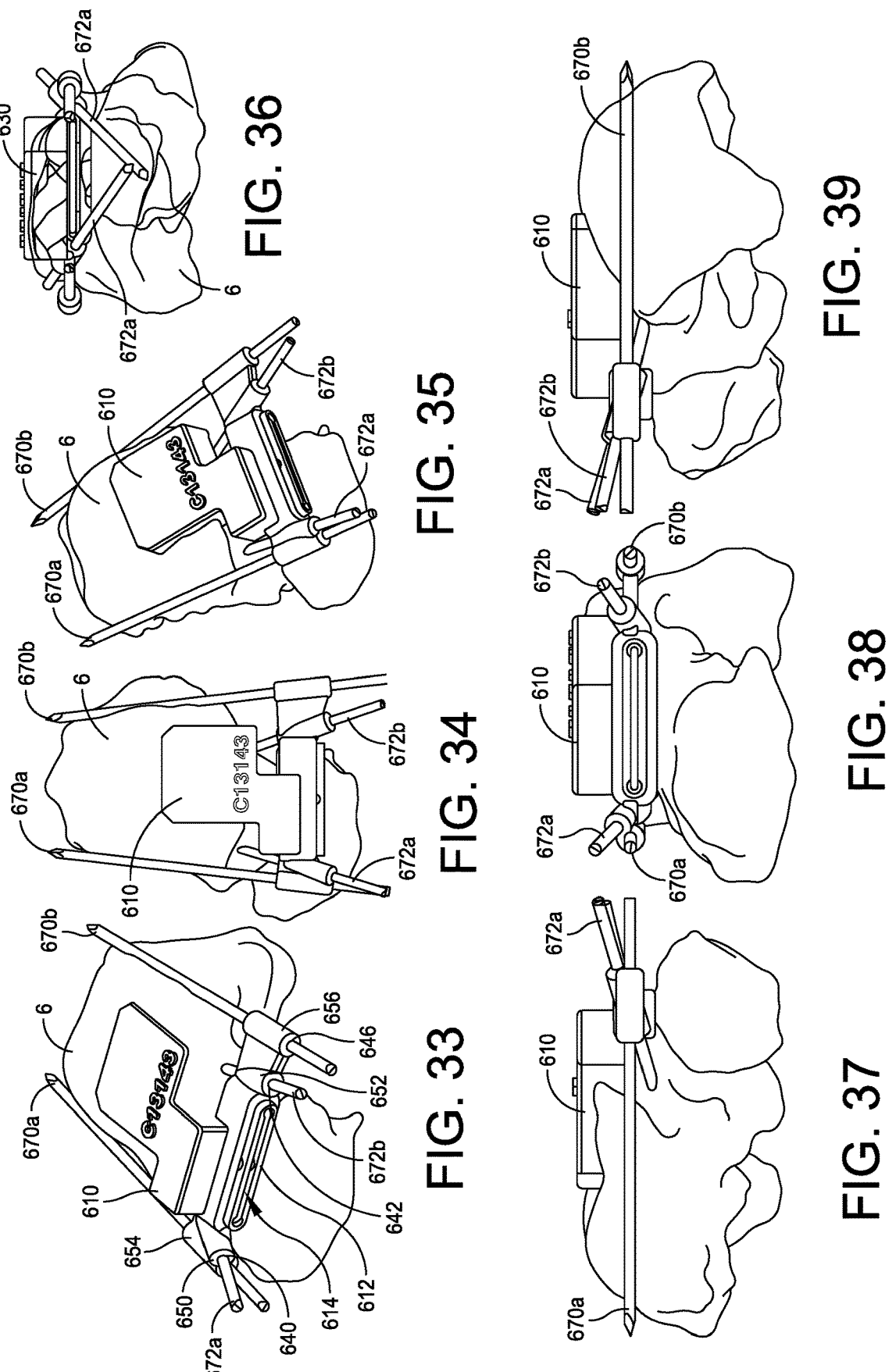

Collect data from patient

Form patient-specific section provide standard section

Couple patient-specific section to the standard section
to form device for use in surgery

384

386

388

388

402

400

400

398

404

390

392

394

396

394

406

406

SURGICAL GUIDES AND METHODS OF MANUFACTURE AND USE

CROSS-REFERENCE TO RELATED APPLICATIONS

This application claims priority under 35 U.S.C. § 119(e) to U.S. Provisional Application No. 63/201,950, filed May 20, 2021, and U.S. Provisional Application No. 63/223,224, filed Jul. 19, 2021, the entireties of which are incorporated herein by reference.

TECHNICAL FIELD

The disclosure relates to surgical devices and methods of manufacture and use thereof. More specifically, the disclosure relates to guide systems with components having at least one surface that matches a profile of a target area, for example, a bone surface of a patient, and the manufacturing methods of the components of the guide system and use thereof in surgical procedures.

BACKGROUND

Joint replacement surgeries are complicated and time consuming. Generally, any steps removed or combined may lead to a faster surgical time, increased customer satisfaction, and/or reduced risk for the patient. Joint replacement surgery with patient-specific instruments may remove alignment steps. However, materials and manufacturing techniques for patient-specific instruments are limited. For example, patient-specific components are generally manufactured using plastic. In surgeries, it is desirable to inhibit and preferably prevent generation of any plastic debris creation during use. Thus, procedures such as drilling, cutting, reaming, etc. generally require the use of a separate component and/or instrument to complete. In fact, when using a patient specific component, pinning is one of the few procedures that using current manufacturing techniques will create little to no plastic debris when positioned in the patient.

As described herein, components from multiple materials may allow for a wider array of steps in a surgical procedure being performed using a specific device during surgery. For example, use of metal protective sleeves or guides in a patient specific device may allow for use of a patient specific component in surgery when completing a step drilling, /cutting/reaming through is a feasible possibility.

Total joint replacement prostheses typically include a specially designed jig or fixture to enable a surgeon to make accurate and precise bone resections in and around the joint being prepared to accept the prosthesis. The ultimate goal with any total joint prosthesis is to approximate the function and structure of the natural, healthy structures that the prosthesis is replacing. Should the prosthesis not be properly attached to the joint or not properly aligned, discomfort to the patient, gait problems, or degradation of the prosthesis may result.

SUMMARY

Utilizing computer-assisted surgery and/or minimally-invasive systems may improve outcomes for patients by allowing for the use of patient-specific methods, instruments, and/or devices. In particular, joint replacement surgeries are complicated and time consuming and any steps that can be removed or combined may decrease surgical time thereby potentially reducing infection risk for the patient and likely increasing patient and/or doctor satisfaction. Joint replacement surgery with patient-specific instruments (e.g. using pre-operative planning such as imaging, computer assisted design, and/or additive manufacturing methods such as three-dimensional (3D) printing capabilities to use the patient's anatomy as a way to produce instruments and/or devices with patient specific surfaces as well as align instruments precisely) removes alignment steps. Patient-specific instruments and/or devices may be manufactured, in part, using plastic. However, some procedures that include drilling, cutting, reaming, etc., through a device may require liners positioned in areas through which the activity occurs. In particular, metal liners, such as sleeves may inhibit production of debris during use, for example, when drilling, cutting, reaming, or the like through a device having protective components and/or liners such as metal sleeves and/or guides. In some instances, combining components and/or liners inside an injection molded plastic body, which may be coupled to a patient-specific surface, may provide unique alignment for a patient while reducing costs of manufacturing and allowing drilling and cutting instruments to be used with patient-specific instruments and/or device while only touching an embedded component such as a metal sleeve.

Devices, elements, and/or instruments may be formed from materials selected for particular properties of interest. Materials used in devices, instruments, and/or elements may be selected based on properties such as compatibility with in vivo use, strength such as yield strength and/or ultimate strength, Young's modulus, creep/viscoelasticity, fatigue, resistance to abrasive wear, compatibility with post-processing procedures such as cleaning, and sterilization and/or other properties of interest. Materials of interest for use in devices, instruments, and/or elements thereof may include but are not limited to plastics such as polycarbonate (PC), polyethylene (PE), methyl methacrylate (MMA), polymethyl methacrylate (PMMA), polyether ether ketone (PEEK), poly ether ketone ketone (PEKK), acrylonitrile butadiene styrene (ABS), polylactic acid (PLA), hydroxyapatite, ceramics such as calcium phosphate ceramics, carbon-based materials such as carbon fiber, graphite, graphene, metals such as titanium, tantalum, and niobium, alloys like stainless steel, cobalt-chromium alloys, titanium alloys, aluminum alloys, and/or nitinol In some embodiments, it may be desired to use a material having a hardness selected based on the requirement of use.

For patient-specific surgical alignment guides, surgical planning for implant sizing and alignment may be performed pre-operatively based on a computer tomography (CT), magnetic resonance imaging (MRI) or other three dimensional (3D) medical imaging dataset, usually in a 3D computer aided design (CAD) environment. Based on the planned location and alignment of the respective implants, the surgical alignment guide may be designed to replicate the planned implant alignment in concert with the other surgical preparation instruments by fitting over the patient's bone and/or cartilage in one specific position based on the topography of the patient's anatomy. As an additional intra-operative check using imaging, such as fluoroscopy may be useful in confirming that the location of the alignment guide has been achieved to the surgeon's satisfaction. Such an ability to check the alignment of the guide early in the surgical procedure, prior to fully committing to the placement of the alignment guide, may reduce the risk of improperly preparing the bone and give the surgeon an opportunity to find a location and alignment of the guide that meets his expectations.

Use of a combination of pre-operative planning, additive manufacturing, such as 3D printing capabilities, and/or molding may allow use of devices conforming to the patient's anatomy to ensure proper alignment of components. For example, utilizing guides, such as metal sleeves inside an injection molded plastic body affixed to a reduced profile patient-specific surface may provide alignment with a surface in a patient's body while reducing costs of manufacturing. Further, utilizing such a construction may allow drilling and cutting instruments to be used in conjunction with patient-specific components and/or devices while inhibiting and/or preventing contact between the patient specific component and/or device and the instrument, for example, by limiting contact of an instrument to the embedded metal subcomponent, for example a metal sleeve.

In some instances, a device used in the methods described herein may include multiple body sections and guides. For example, a device may include two plastic body section and two metal inserts. In particular, a device body may include a patient-specific portion that is injection molded and a standardized "main body" shape with metal pieces inserted into the mold before manufacturing.

During manufacturing of such a device, elements such as guides capable of acting as drill sleeves, cut sleeves and/or as guides for other elements during use, fasteners, pins such as guidewires, Denham pins, transfixation wires, K-wires ("Kirschner wires"), olive wires (e.g., BB-taks™), spheres (e.g., pellets and/or metal spheres like BBs), or other elements known in the art, may be inserted into the molds in specific locations and/or orientations that depend on the type of surgery to be performed, the geometry of a patient's anatomy, and/or target surfaces, for example, surfaces of bone. In some instances, these elements may be metal inserts including, but not limited to drill sleeves such as cannulated cylinders, cut sleeves such as hollow oval prisms and/or other geometric shapes, metal cylinders, pins, wires such as K-wires olive wires (i.e., BB-taks™), spheres, pellets, labels, etc. Customization of a device may include selecting elements such as inserts based on a position of use in vivo, geometry of the patient, surgical procedure such as minimally invasive surgery (MIS), and/or types of instruments to be used such as blades (e.g., saw blades).

Devices described herein may include indicators such as labels on one or more surfaces (e.g., patient specific labels and/or use labels, reference points, measuring members, provided on surfaces of devices and/or elements thereof) and/or embedded therein. These indicators on elements of a device may be used to identify parts during manufacturing and/or surgery.

Matching surfaces of a device to a patient, in particular, to the natural anatomical surface of a patient's bone may ensure a better fit during use during surgery or use in vivo thereafter. For example, in a multi-sectional device components of the device may include a patient-specific component having a negative surface from the patient's target bone region on a bone-engaging surface and a coupling surface designed to be coupled to a standard body component. In some instances, the bone-engaging surface may be positioned on a surface opposite the coupling surface.

A device may be formed from a patient-specific component and a standard body component that coupled in a manner that allows them to permanently coupled or temporarily coupled, for example, the standard body component may be separated from the patient-specific component such that the standard body component may be reused. In some instances, the patient-specific component and the standard body component may be affixed permanently to each other during an assembly manufacturing step using couplers including, but not limited to fasteners, adhesives such as glue, etc. and combinations thereof.

The disclosed embodiments provide a modular system for enabling secure connection and accurate placement of one or more cutting guides in relation to a resection guide locator while providing a variety of connection options for easily placing tools and/or cutting guides for use during the operation. The modular configuration of the system thereby enables cutting guides (shown or not shown) to be simply and securely positioned for use in a step of a surgical procedure, with multiple different connection options being provided (e.g., aligned holes, projections, etc.) In combination with patient-specific configuration of the components, a more robust surgical system can be produced with multiple cutting guide options, all easily implemented as desired.

Disclosed embodiments may be used in a variety of applications and methods, including surgical methods for operating on a patient, and, in particular, a joint (e.g., an ankle joint, an elbow, knee, shoulder, etc.). The disclosed components may include features for positioning guide openings for receiving tools (e.g., saws, drills, drivers, etc.) for performing steps of a procedure. In one embodiment, a method includes positioning a resection guide locator with respect to a joint. For example, the resection guide locator may be positioned with respect to a first bone (e.g., tibia) of an ankle joint. A first component, such as resection guide may be attached to the resection guide locator, such as by inserting the resection guide into the receptacle of the resection guide locator. A first operative step may be performed using the resection guide, such as a resection cut of the tibia. With the resection guide locator and the first component in place, a second component, such as a second resection guide, may be attached. For example, a second resection guide may be attached to the receptacle of the first resection guide, and a second operative step performed. For example, a talar resection guide may be attached to a first resection guide and a talar resection step performed. In another embodiment, the second component may be a corner protector peg attached to the first resection guide. In some embodiments, components may be assembled on the patient, or may be pre-assembled prior to positioning with respect to the patient. The disclosed embodiments are thus applicable as a modular system providing a user with multiple options for performing a procedure.

Devices described herein may include a body that includes one or more sections with components positioned therein. For example, a device may have two sections and one or more metal inserts positioned throughout the body. Body sections may be injection molded from materials selected. For example, body sections may be formed using insert molding or overmolding. In an embodiment, a standardized "main body" section with inserts may be formed by placing inserts into the mold before manufacturing. Inserts may include sleeves, for example, drill sleeves, cut sleeves, bearings, fasteners such as pins, screws, and/or staples or combinations thereof. Inserts may be formed of materials suitable for use in the body and selected for predetermined properties required by the intended use. In some embodiments, materials may be selected from metals, composites, or the like. It may be desirable, in some instances, to use a material having a hardness greater than about 80 Brinnell to reduce and/or inhibit production of debris during use. For example, materials used may include stainless steel grades equivalent to 316 stainless steel or a stainless steel that is harder. Material selection may also be influenced by the design of a device and/or elements thereof. In particular, size of the device and/or elements and/or the desired fit between the device, elements, and/or the target area may necessitate use of specific materials to meet the requirements of use.

In one aspect, a method includes forming a mold insert for a mold cavity, the insert having a surface that corresponds to a surface topology of a bone. The method further including positioning the mold insert in the mold cavity. Materials for use in devices described herein may be selected based on desired properties of the materials, such as characteristics of polymer materials, required properties of the device, and/or suitability for use in 3D printing such as stereolithography, selective laser sintering, or the like. In some instances, some of material used to form at least a portion of the device may be radiolucent. For example, a method may include injecting a radiolucent material into the cavity to form a surgical guide having a surface that is complementary to the surface topology of the bone.

In another aspect, a method includes positioning a standard section of a device in a printing cavity of an additive manufacturing machine. In general, a geometry of the standard section may not be patient specific. In some embodiments, a method for making a device may include positioning a standard section within an additive manufacturing machine such that a patient-specific engaging section may be coupled to the standard section. The patient-specific engaging section may include at least one surface that is adapted to match surface topology of a bone.

In another aspect, a method includes providing a standard guide body having a geometry that is not patient specific.

In some instances a portion of the guide body may form a patient match body that includes at least one surface that is adapted to match surface topology of a bone. The method further includes affixing the guide body to the patient match body to form a surgical guide that is customized to a patient.

In another aspect, a surgical guide includes a patient match body, a standard guide body, and a sleeve. The patient match body has a surface that is complementary to a surface topology of a bone. The patient match body defines a first aperture. The standard guide body is fixedly coupled to the patient match body. The standard guide body defines a second aperture aligned with the first aperture. The sleeve extends through the first aperture and the second aperture.

In another aspect, a surgical guide includes a patient match body and an insert. The patient match body has a surface that is complementary to a surface topology of a bone. The insert is coupled to the patient match body using an injection molding process such that the insert is fixedly coupled to the body.

In another aspect, a method includes forming a patient match body having a surface that is complementary to a surface topology of a bone. The method further includes positioning the patient match body in a mold cavity. The method further includes injecting material into the cavity to form a second body that is fixedly coupled to the patient match body. At least one aperture extends through the patient match body and the second body, and wherein the aperture is configured to guide a surgical instrument during a surgery.

In another aspect, a method includes positioning a metallic body in a printing cavity of an additive manufacturing machine. The method further includes forming a patient match body in the printing cavity of the additive manufacturing machine such that the patient match body is affixed to the metallic body. The patient match body includes at least one surface that is adapted to match surface topology of a bone.

In another aspect, a method includes positioning a metallic body in a mold cavity. The method further includes injecting material into the mold cavity to form a patient match body such that the patient match body is affixed to the metallic body. The patient match body includes at least one surface that is adapted to match surface topology of a bone.

Although the invention has been described in terms of exemplary embodiments, it is not limited thereto. Rather, the appended claims should be construed broadly, to include other variants and embodiments of the invention, which can be made by those skilled in the art without departing from the scope and range of equivalents of the invention.

BRIEF DESCRIPTION OF THE DRAWINGS

These and other features and advantages of the apparatuses and methods described herein will be more fully disclosed in, or rendered obvious by, the following detailed description of the preferred embodiments, which is to be considered together with the accompanying drawings wherein like numbers refer to like parts.

FIG. 22A depicts a side perspective view of an embodiment of corner protectors;

FIG. 22B depicts a front view of an embodiment of a medical device that includes a resection guide locator and a resection guide coupled to each other and bone and corner protectors positioned in the resection guide;

FIG. 22C depicts a side perspective view of an embodiment of a connector configured to be inserted into a resection guide;

FIG. 30A depicts a perspective view of a talar pin guides positioned for use in an embodiment of an exemplary process for positioning a resection guide with respect to a joint;

FIG. 30B depicts a perspective view of a modular resection guide coupled to bone and talar pin guides positioned for use in an embodiment of an exemplary process with respect to a joint;

FIG. 30C depicts a perspective view of a modular resection guide coupled to bone and talar pin guides positioned for use in an embodiment of an exemplary process with respect to a joint;

FIG. 30D depicts a front view of a modular resection guide coupled to bone and talar pin guides positioned for use in an embodiment of an exemplary process with respect to a joint;

FIG. 31A depicts a front view of a modular resection guide coupled to bone and positioned for use in an embodiment of an exemplary process with respect to a joint;

FIG. 31B depicts a front view of a modular resection guide coupled to bone and positioned for use in an embodiment of an exemplary process with respect to a joint;

FIG. 31C depicts a front view of a modular resection guide coupled to bone and positioned for use in an embodiment of an exemplary process with respect to a joint;

FIG. 31D depicts a front view of a modular resection guide coupled to bone and positioned for use in an embodiment of an exemplary process with respect to a joint;

FIG. 32A depicts a front view of a modular resection guide coupled to bone and positioned for use in an embodiment of an exemplary process with respect to a joint;

FIG. 32B depicts a front view of a modular resection guide coupled to bone and positioned for use in an embodiment of an exemplary process with respect to a joint;

FIG. 32C depicts a front view of a modular resection guide coupled to bone and positioned for use in an embodiment of an exemplary process with respect to a joint;

FIG. 32D depicts a front view of a modular resection guide coupled to bone and positioned for use in an embodiment of an exemplary process with respect to a joint;

FIG. 33 depicts a perspective view an embodiment of a resection guide locator and pins coupled to bone;

FIG. 34 depicts a top perspective view an embodiment of a resection guide locator and pins coupled to bone;

FIG. 35 depicts a top perspective view an embodiment of a resection guide locator and pins coupled to bone;

FIG. 36 depicts a top cross-sectional view an embodiment of a resection guide locator and pins coupled to bone;

FIG. 37 depicts a side view an embodiment of a resection guide locator and pins coupled to bone;

FIG. 38 depicts a front view an embodiment of a resection guide locator and pins coupled to bone;

FIG. 39 depicts a side view an embodiment of a resection guide locator and pins coupled to bone;

FIG. 60 depicts a side view of an embodiment of a device for use in orthopedic surgery having a patient-specific surface, a standard section and inserts;

FIG. 61 depicts a side view of an embodiment of a device for use in orthopedic surgery having a patient-specific surface, a standard section and inserts;

FIG. 62 depicts a side view of an embodiment of a device for use in orthopedic surgery having a patient-specific surface, a standard section and inserts;

FIG. 63 depicts a side view of an embodiment of a device for use in orthopedic surgery having a patient-specific surface, a standard section and inserts;

FIG. 64 depicts a flow-chart depicting steps involved in forming a device for use in orthopedic surgery having a patient-specific surface;

FIG. 65 depicts a schematic cross-sectional view of an embodiment of a device for use in orthopedic surgery positioned within a mold and wherein the device has a patient-specific surface, a standard section with device engaging surface, and inserts positioned therein;

FIG. 66 depicts a schematic cross-sectional view of an embodiment of a device for use in orthopedic surgery positioned within a mold and wherein the device has a patient-specific surface, a standard section with device engaging surface, and inserts positioned therein;

FIG. 67 depicts a schematic cross-sectional view of an embodiment of a device for use in orthopedic surgery positioned within a mold that includes a mold insert and wherein the device has a patient-specific surface, a device engaging surface, and sleeves positioned therein;

FIG. 68 depicts a schematic cross-sectional view of an embodiment of a device for use in orthopedic surgery positioned within a mold that includes a mold insert and wherein the device has a patient-specific surface, a device engaging surface, and sleeves positioned therein;

FIG. 69 depicts a schematic cross-sectional view of an embodiment of a device for use in orthopedic surgery positioned within a mold that includes a mold insert and wherein the device has a patient-specific surface, a device engaging surface, and sleeves positioned therein;

FIG. 70 depicts a schematic of an enlarged cross-sectional view of a mold, a mold insert, and a portion of a device on which an indicator is formed during molding;

FIG. 71 depicts a front perspective view of a resection guide;

Figure 72:
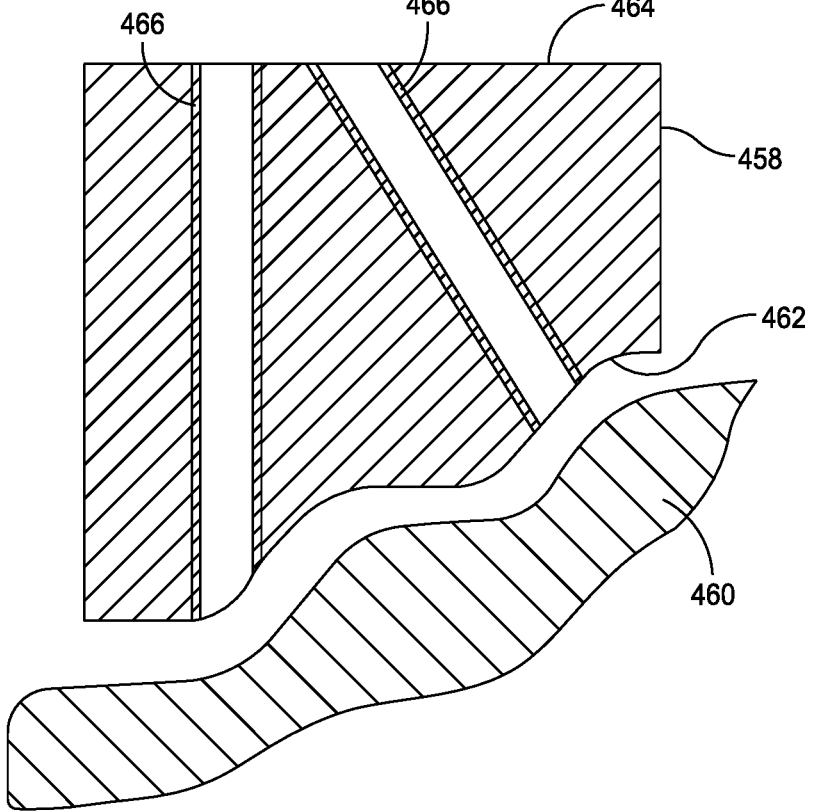
Figure 73:
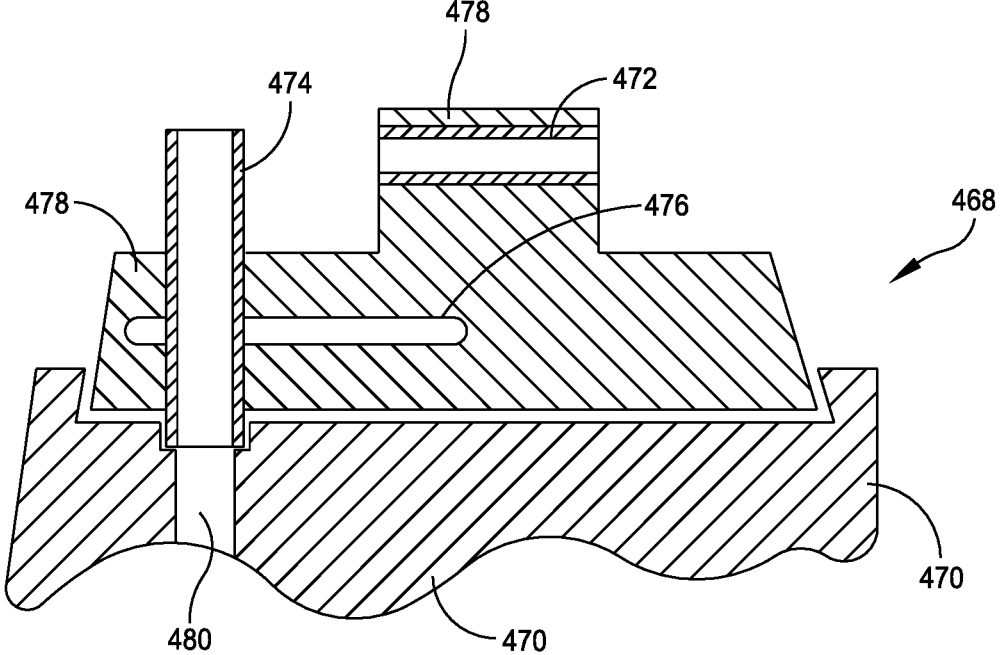
Figure 74:
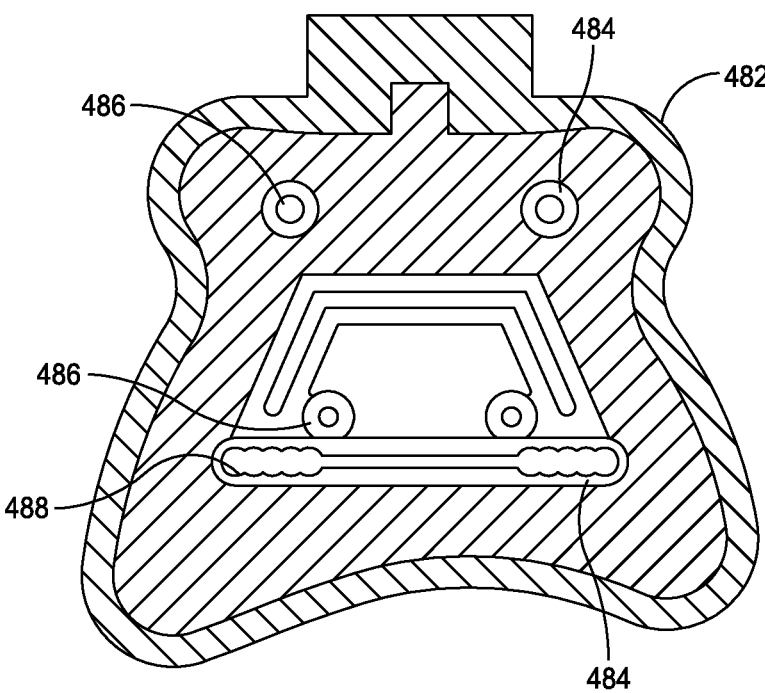
Figure 75:
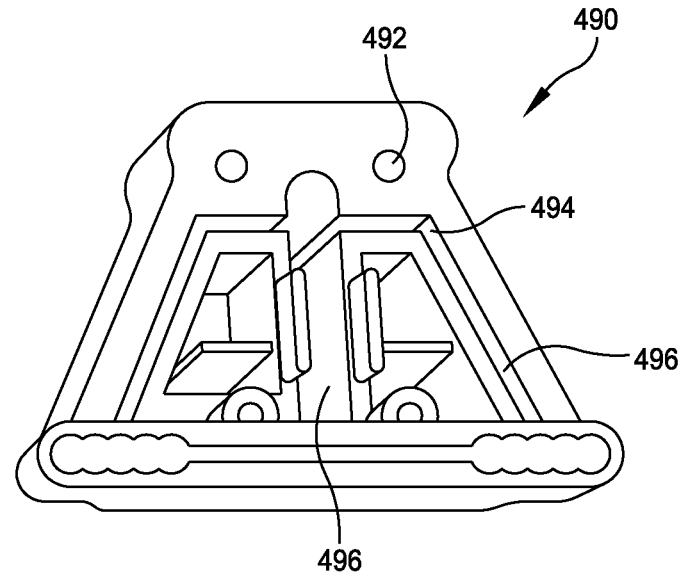
Figure 76:
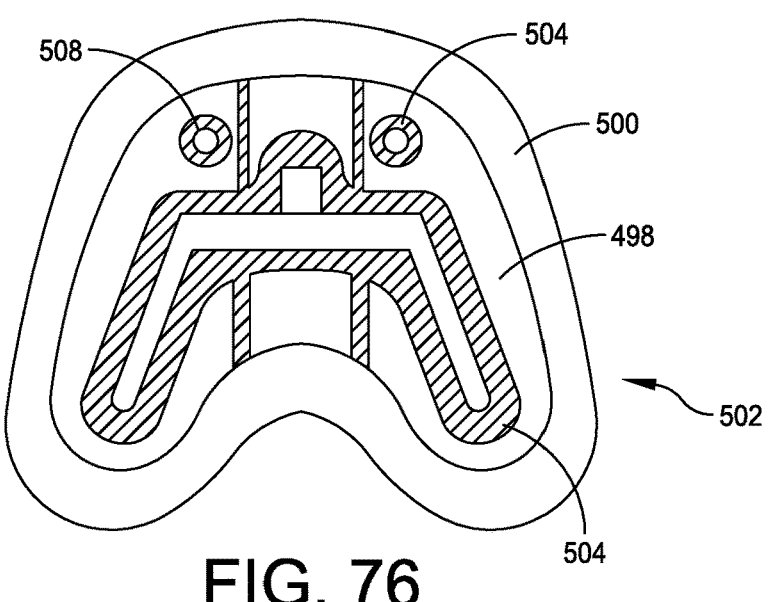
Figure 77:
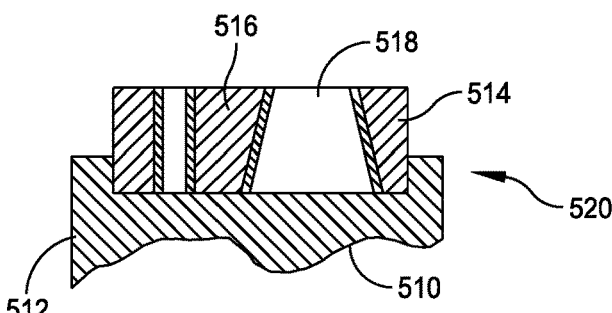
Figure 78:
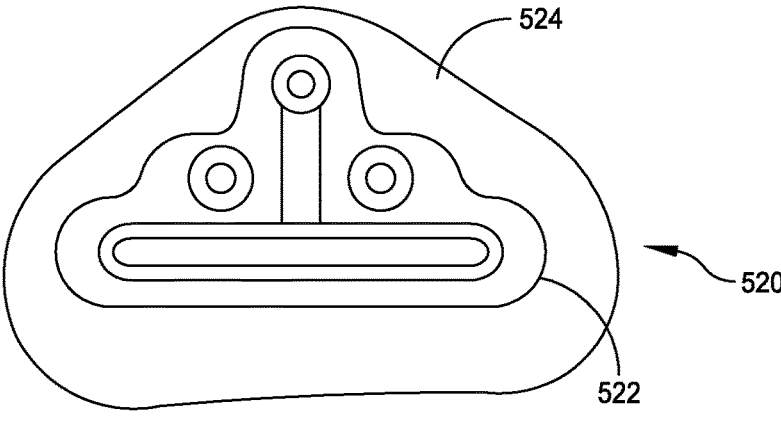

FIG. 72 depicts a schematic cross-sectional view of an embodiment of a device for use in orthopedic surgery positioned proximate bone and wherein the device has a patient-specific surface, a standard section with device engaging surface, and inserts positioned therein;

FIG. 73 depicts a cross-sectional view of an embodiment of a device for use in orthopedic surgery having a patient-specific surface, a standard section with device engaging surface, and inserts positioned therein;

FIG. 74 depicts a front perspective view of a resection guide;

FIG. 75 depicts a front perspective view of a resection guide;

FIG. 76 depicts a front perspective view of a resection guide;

FIG. 77 depicts a cross-sectional view of an embodiment of a device for use in orthopedic surgery having a patient-specific surface, a standard section with device engaging surface, and inserts positioned therein; and FIG. 78 depicts a front perspective view of a resection guide.

DETAILED DESCRIPTION

This description of the exemplary embodiments is intended to be read in connection with the accompanying drawings, which are to be considered part of the entire written description. The drawing figures are not necessarily to scale and certain features of the invention may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Disclosed embodiments include custom manufactured surgical instruments and devices such as guides (e.g., resection guides) and/or fixtures that may be based upon a patient's anatomy as determined by a computer tomography scanner (CT), magnetic resonance imaging machine (MRI), fluoroscopy, or the like medical imaging technology. In some instances, a CT or MRI scanned image or series of images may be taken of a patient's joint, for example a knee, shoulder, elbow, or ankle. For example, when using images for an ankle surgery it may be helpful to include images of the limb from the pelvis and/or the foot. Any CT and/or MRI scanned image data may then be converted to a solid computer model of the lower limb often including the pelvis, femur, patella, tibia, or foot to determine implant alignment, type and sizing using specialized modeling methods that are often embodied in computer software. Computer generated solid models that are derived from CT or MRI scan image data will often include precise and accurate information regarding the surface contours surrounding the structures that have been imaged, e.g., the surface topography of the bones or contour of fascia that have been imaged. It will be understood that by surface topography it is meant the location, shape, size and distribution of surface features such as concavities and prominences or the like.

Disclosed embodiments further include components, such as guides, guide adapters, and mounts, that include features for creating a modular surgical system. For example, a mount can be configured to features that enable the mount to be used with any of a plurality of cutting guides, depending on a needed step or procedure related to the surgery. For example, a separate resection guide can be insertable into a mount to provide multiple attachment options for a plurality of cutting guides. Further, the mount can include features that improve upon its connection to patient anatomy and/or its connection to a cut guide or other separate component. The mount and/or cut guides can include particular geometries to achieve these and other benefits attained by the disclosed embodiments.

FIGS. 1A, 2A, 3A, and 3B illustrate a medical device 15, according to a first embodiment. The medical device 15 includes a resection guide locator 10 and a resection guide 12. The resection guide locator 10 can be, for example, a tibial resection guide locator formed from a resilient polymer material of the type that is suitable for use in connection with stereolithography, selective laser sintering, or the like manufacturing equipment. Resection guide locator 10 can comprise a unitary block structure with bone engaging features configured for complimentary matching with anatomical surface features of a selected region of the patient's natural bone (e.g., a portion of the tibia). The resection guide 12 can itself be a cutting guide for guiding an instrument during a surgical procedure. For instance, the resection guide 12 may include features for guiding a saw, drill, or other tool during an operation. The resection guide 12 can also include features particularly adapted to allowing additional components to be connected to the resection guide locator 10, as will be further described.

For example, the resection guide locator 10 can include a cruciform tibial yoke 14 projecting upwardly from a base 16 that further defines a guide receptacle 18 for receiving at least a portion of the resection guide 12. Cruciform tibial yoke 14 can include a pair of spaced apart arms 20, 22 that project outwardly from a central post 24. Arms 20, 22 and central post 24 can each have a conformal bone engaging surface that is complementary to the contours of a corresponding portion of the patient's lower tibia. The bone engaging surfaces can be configured for complementary matching with anatomical surface features of a selected region of the patient's natural bone using patient specific instrument software using images of the patient.

The guide receptacle 18 is configured to receive at least a portion of the resection guide 12. The resection guide 12 can include features that enable connection to one or more of a variety of cutting guides, depending on the needs or step of a surgical procedure. In an exemplary embodiment, the guide receptacle 18 and the resection guide 12 include a complementary shape.

Figure 1A:
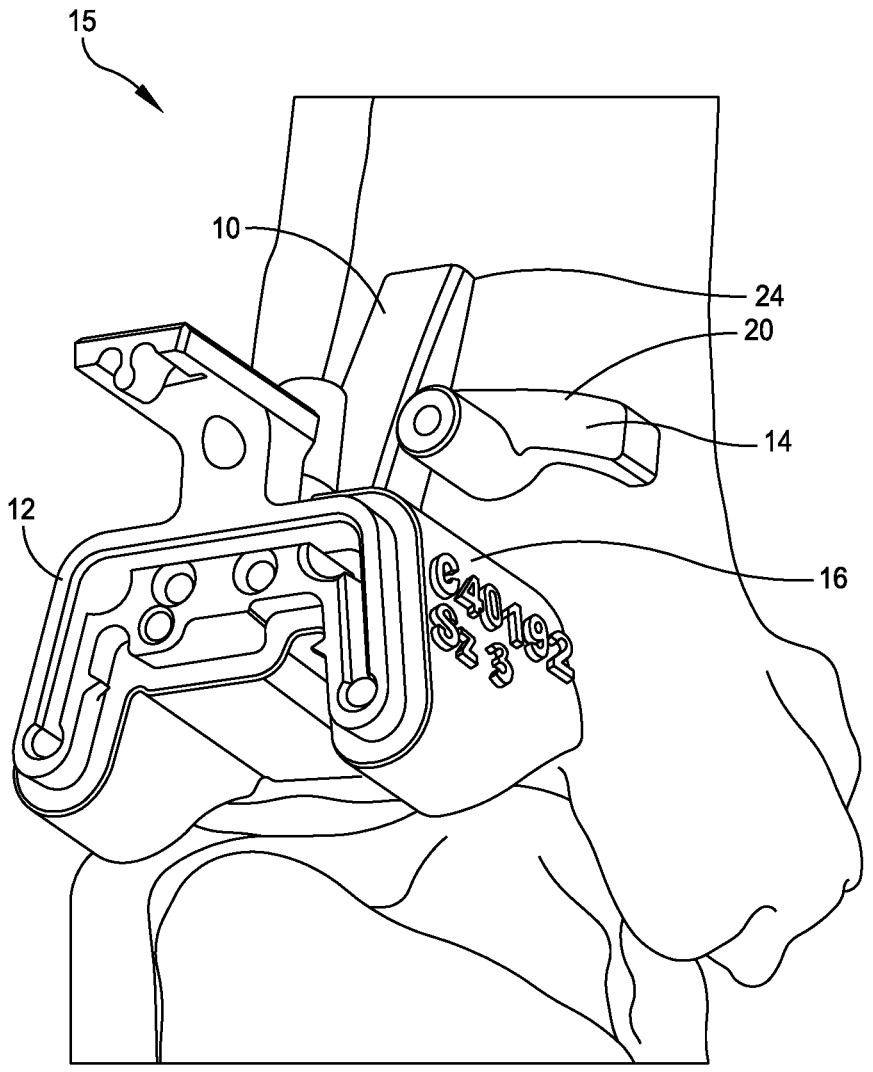
FIG. 1A depicts a medical device positioned near bones of a joint.
Figure 1B:
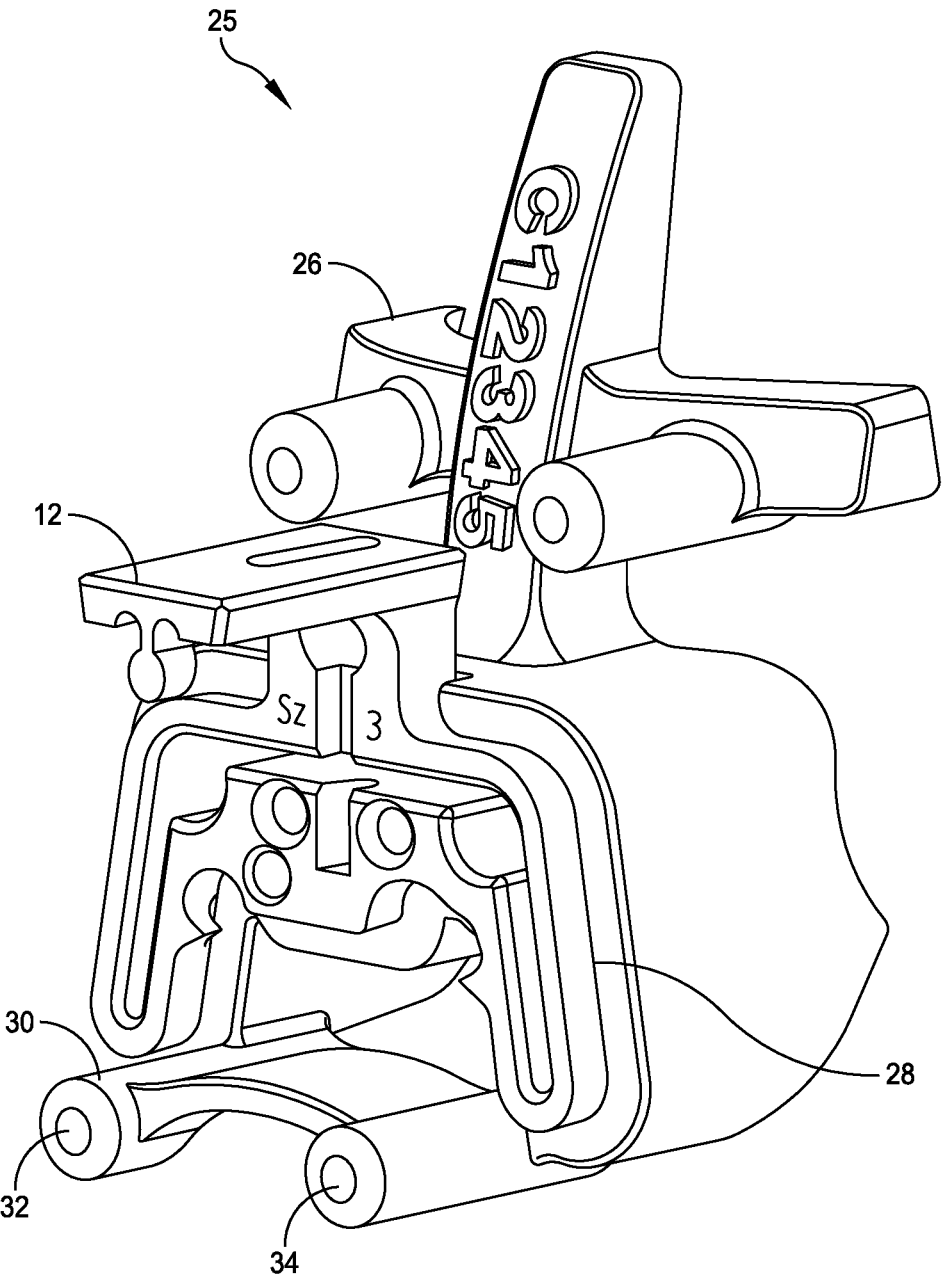
FIG. 1B depicts a perspective view of a medical device that includes a resection guide locator and a resection guide.
Figure 2A:
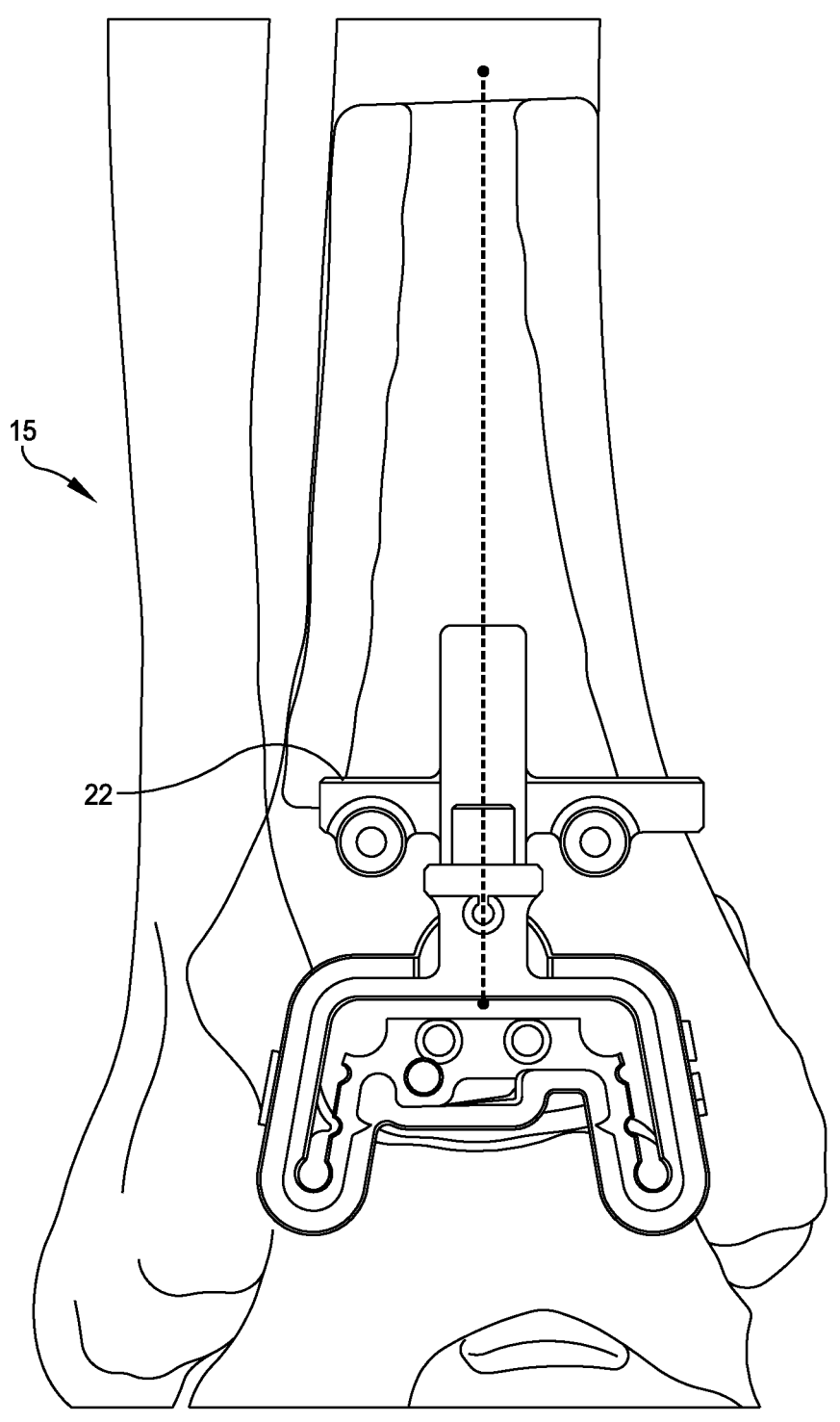
FIG. 2A depicts a front view of a medical device that includes a resection guide locator and a resection guide positioned on bones.
Figure 2B:
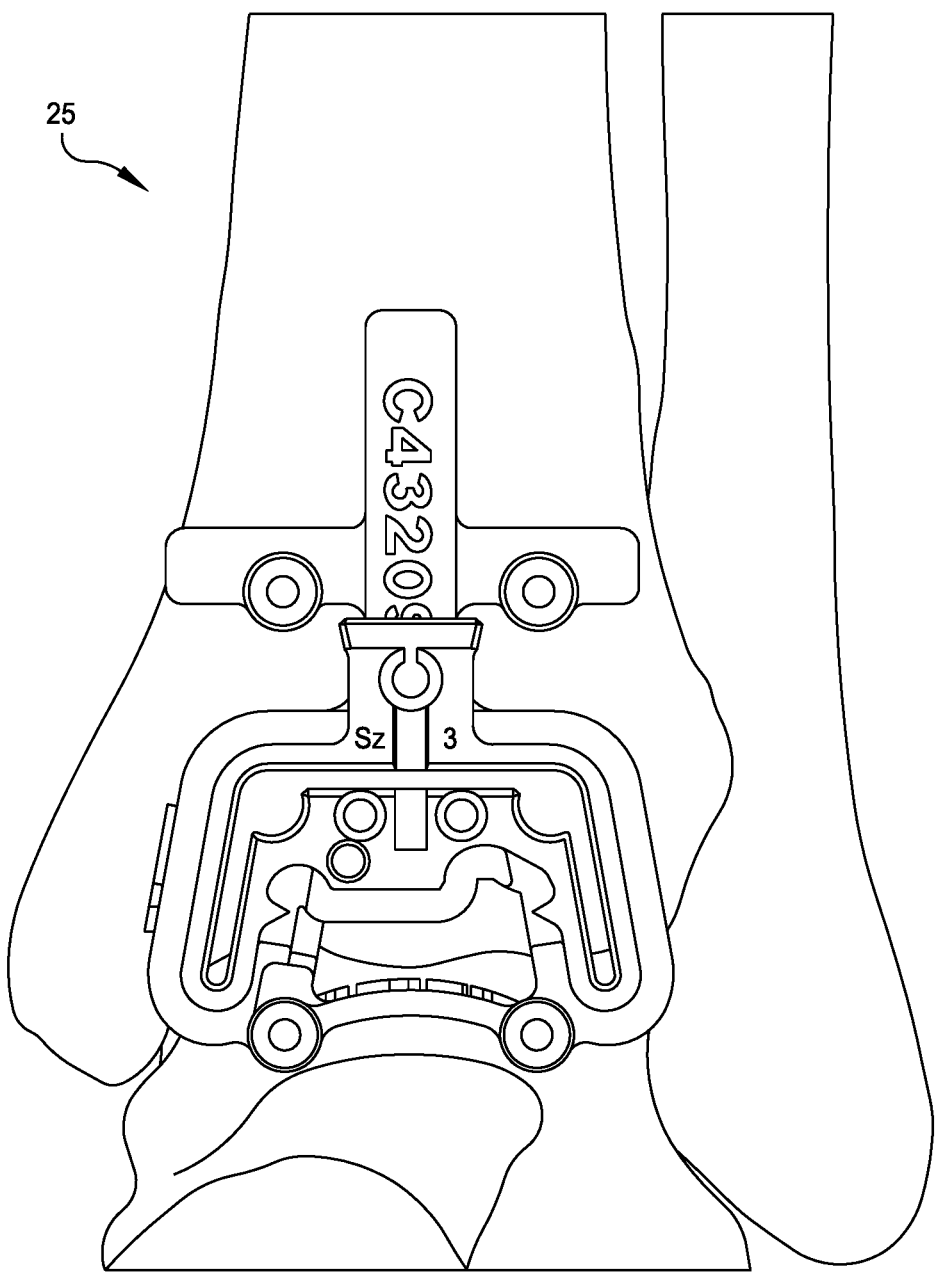
FIG. 2B depicts a front view of a medical device that includes a resection guide locator and a resection guide positioned on bones.

FIGS. 1B and 2B illustrate a medical device 25, according to a second embodiment. The medical device 25 includes a resection guide locator 26 according to an exemplary embodiment. The resection guide locator 26 is similar to the resection guide locator 10 and can be used in conjunction with the resection guide 12 or another similar resection guide. For example, the resection guide locator 26 may comprise a guide receptacle 28 for receiving the resection guide 12. The resection guide locator 26 may further include an extension 30 comprising a pair of talar pin guides 32, 34. The talar pin guides 32, 34 may include holes for receiving and guiding pins or wires into the talus during a medical procedure. The extension 30 may be integrally formed with the rest of the resection guide locator 26.

Figure 1C:
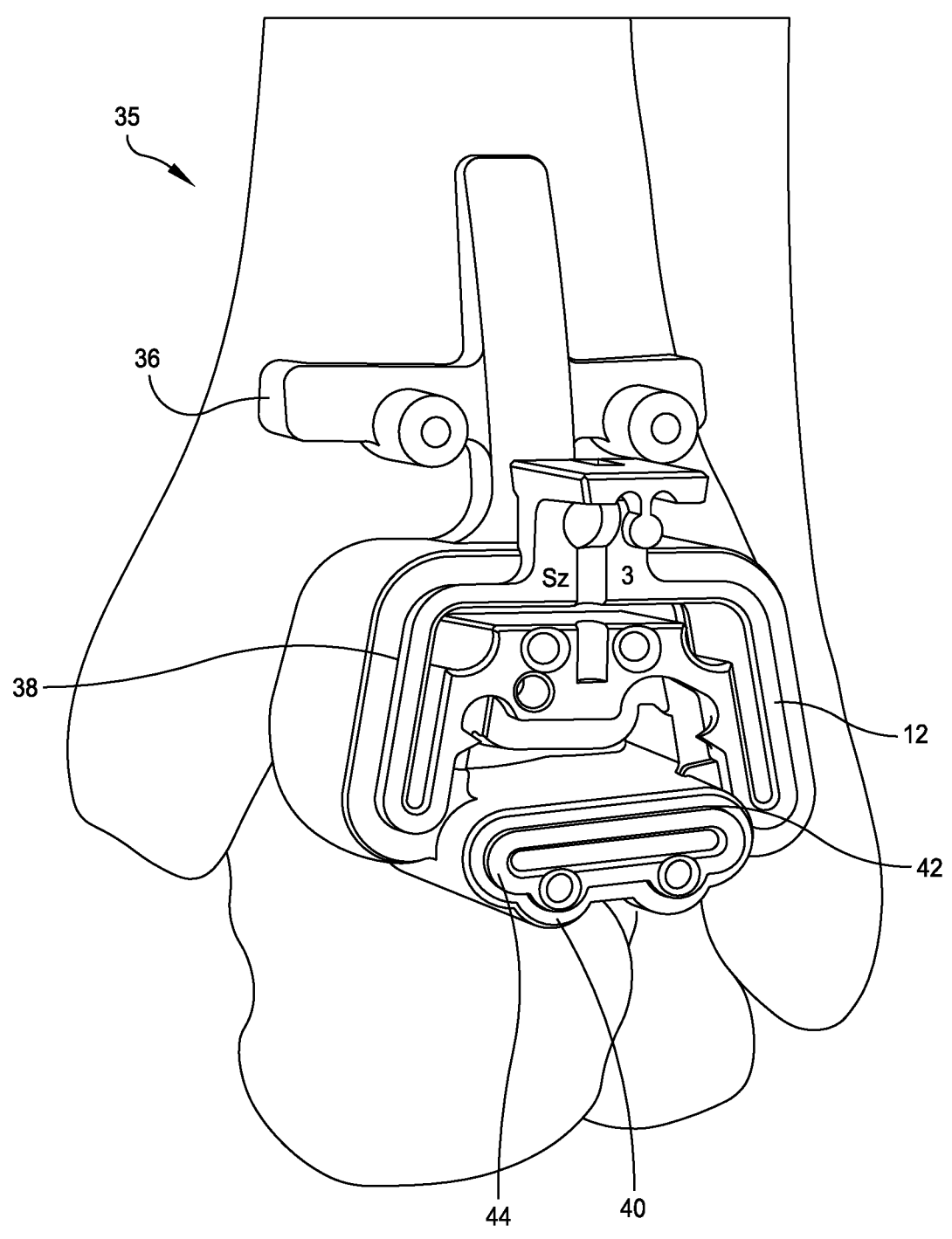
FIG. 1C depicts a perspective view of a medical device that includes a resection guide locator and a resection guide positioned on a bone.
Figure 2C:
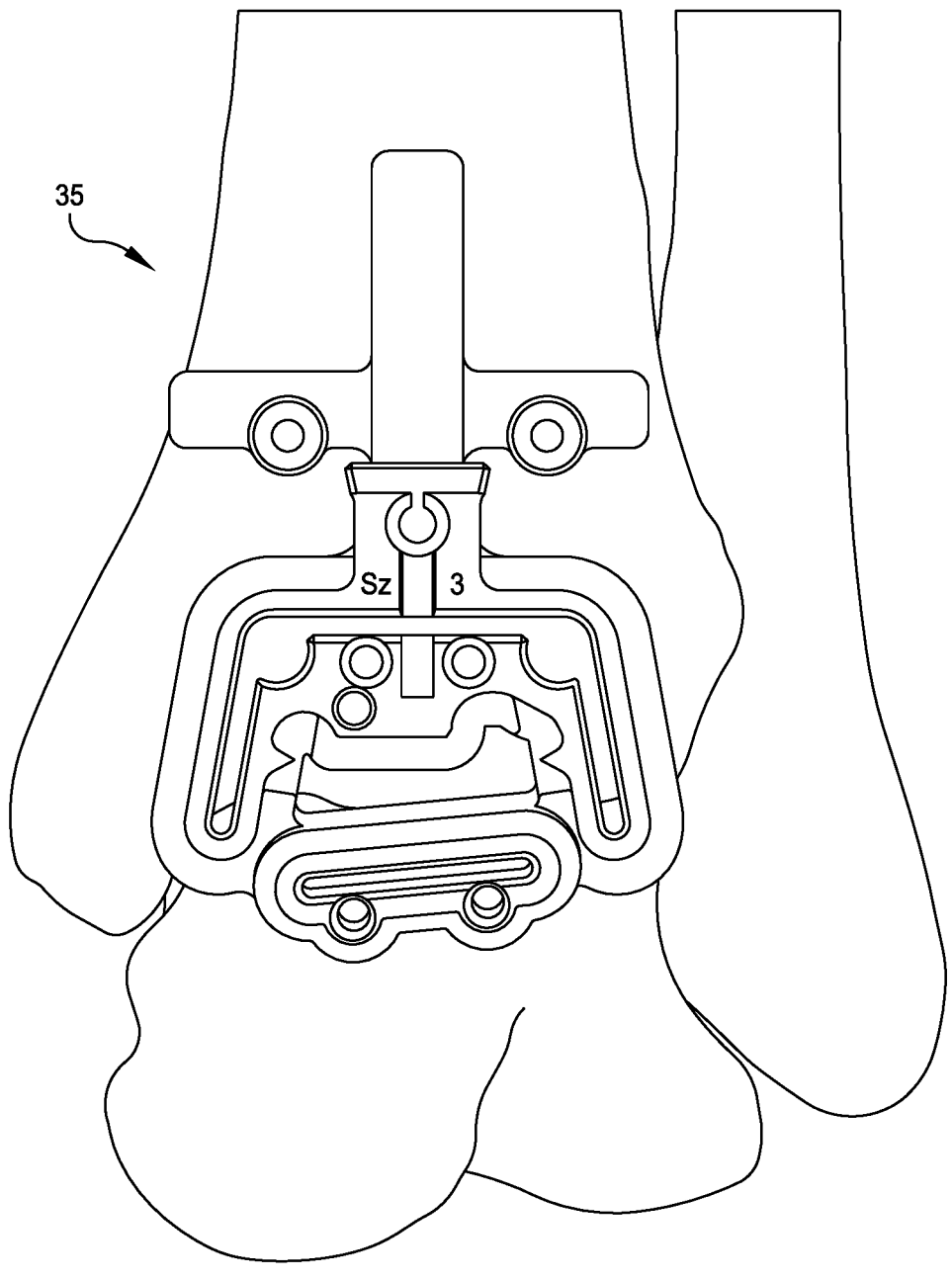
FIG. 2C depicts a front view of a medical device that includes a resection guide locator and a resection guide positioned on bones.
Figure 3B:
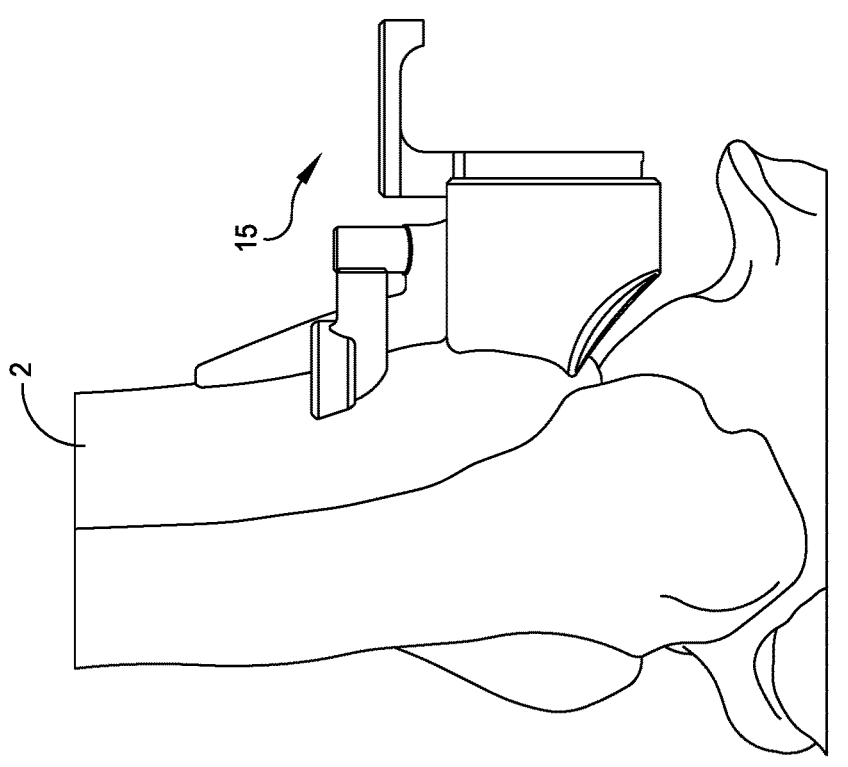
FIG. 3B depicts a side view of a medical device that includes a resection guide locator and a resection guide positioned on bones.
Figure 3A:
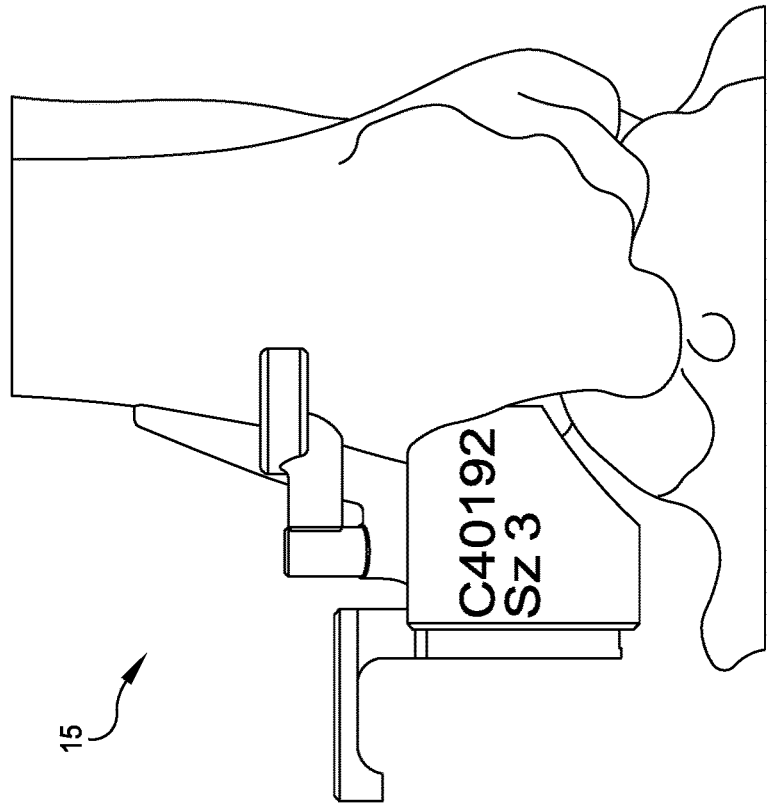
FIG. 3A depicts a side view of a medical device that includes a resection guide locator and a resection guide positioned on bones.

FIGS. 1C and 2C illustrate a medical device 35, according to a third embodiment. The medical device 25 includes a resection guide locator 36 according to another exemplary embodiment. The resection guide locator 36 is similar to the resection guide locators 10 and 26 and can be used in conjunction with the resection guide 12 or another similar resection guide. For example, the resection guide locator 36 may comprise a guide receptacle 38 for receiving the resection guide 12. The resection guide locator 36 may further include an extension 40 comprising a second guide receptacle 42 for receiving a second resection guide 44. According to some embodiments, the resection guide locator 36 may be applicable to a fusion take down procedure.

Figure 4:
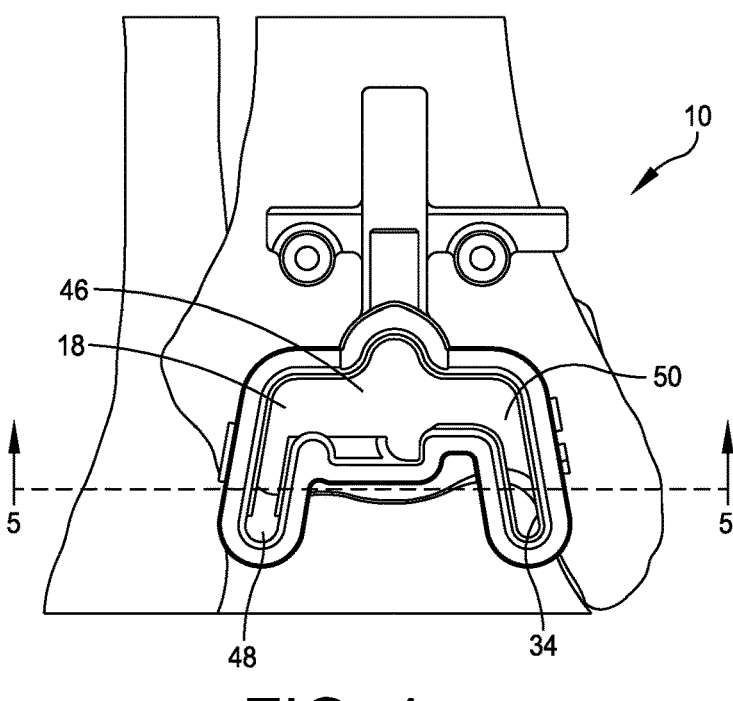
FIG. 4 depicts a front view of a medical device that includes a resection guide locator positioned on bones.

FIG. 4 illustrates the resection guide locator 10 and the guide receptacle 18 without the resection guide 12. The guide receptacle 18 can include a "U" or winged shape having a central portion 46 and a pair of side portions 48, 50. The side portions 48, 50 can extend downwardly away from the central portion 46 in at least some embodiments. The guide receptacle 18 can thus guide a similar "U" shaped tibial cuts using the slots formed by the central portion 46 and side portions 48, 50 as guides.

Figure 5:
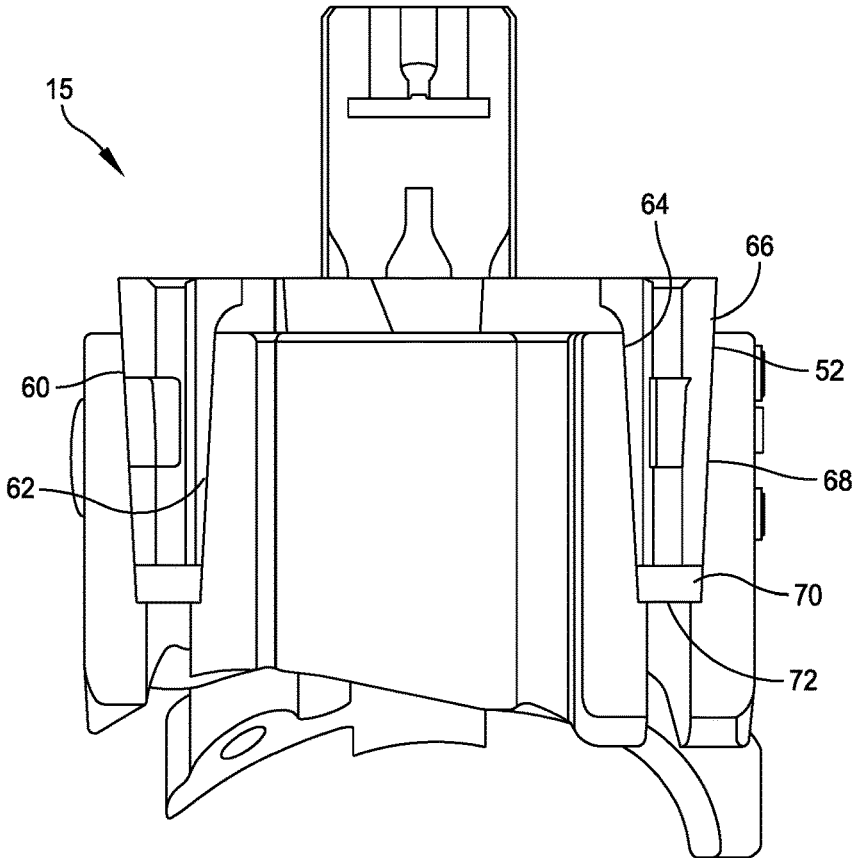
FIG. 5 depicts a top view of a medical device that includes a resection guide locator and a resection guide positioned therein.
Figure 6B:
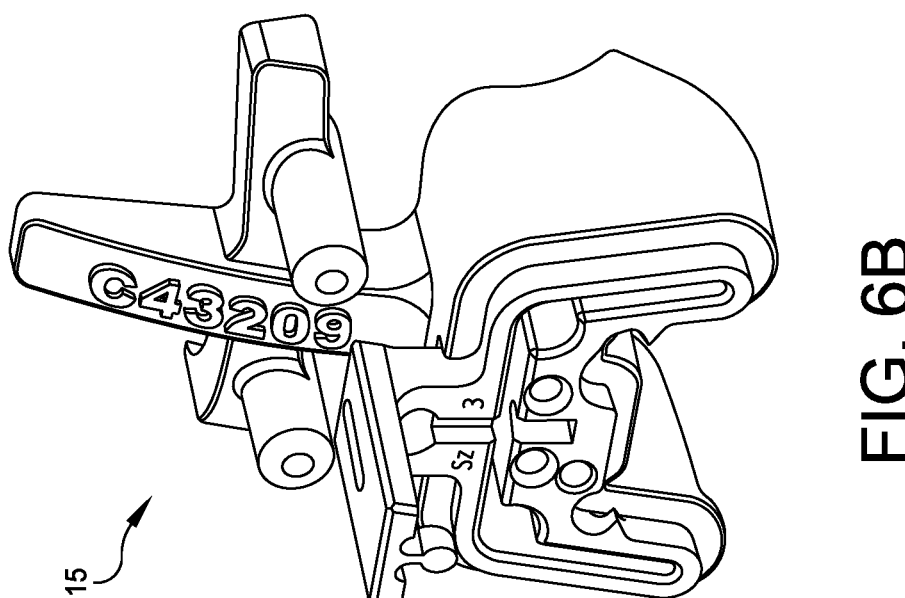
FIG. 6B depicts a perspective view of a medical device that includes a resection guide locator and a resection guide positioned therein.
Figure 6A:
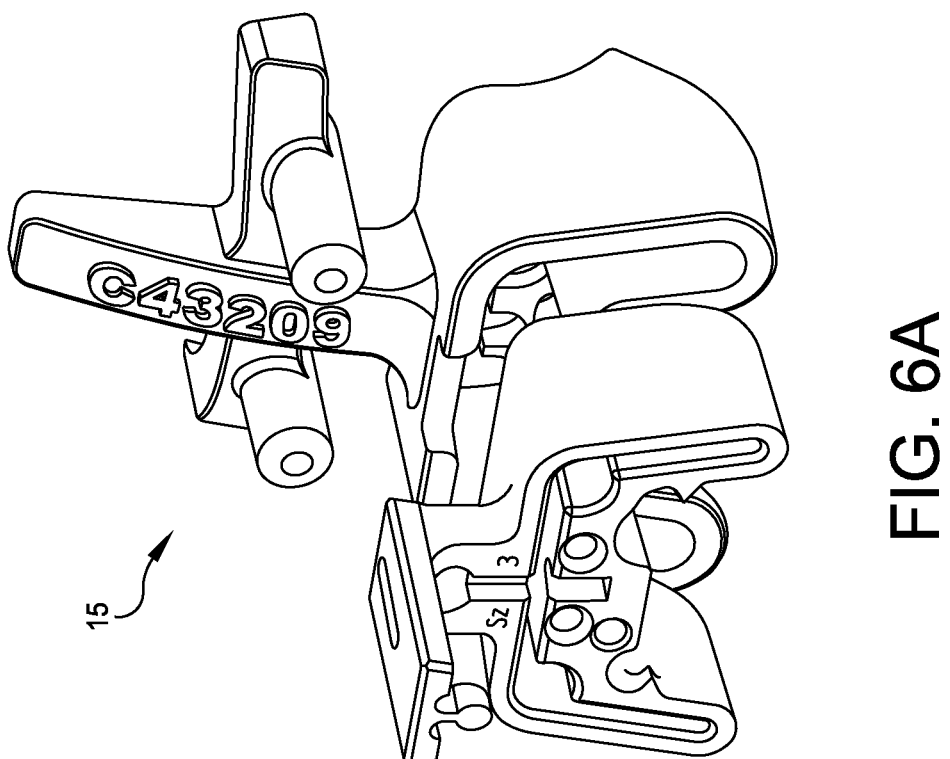
FIG. 6A depicts a perspective view of a medical device that includes a resection guide locator and a resection guide positioned prior to insertion.
Figure 6E:
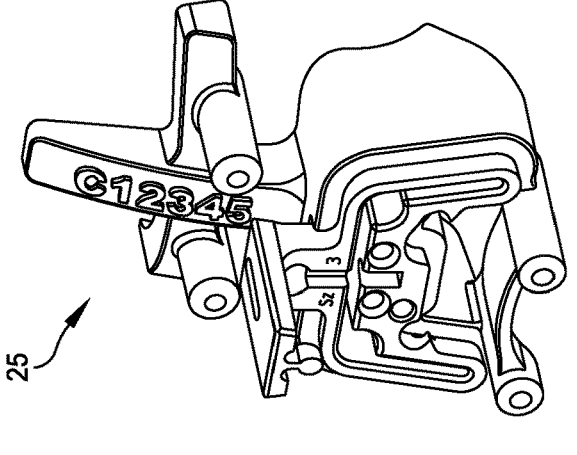
FIG. 6E depicts a perspective view of a medical device that includes a resection guide locator and a resection guide positioned therein.
Figure 6D:
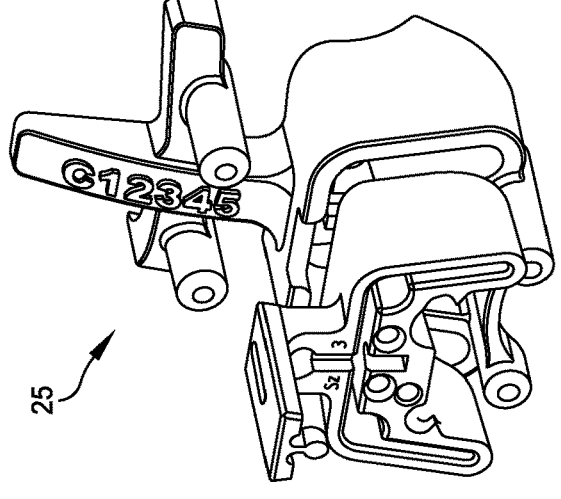
FIG. 6D depicts a perspective view of a medical device that includes a resection guide locator and a resection guide positioned prior to insertion.
Figure 6C:
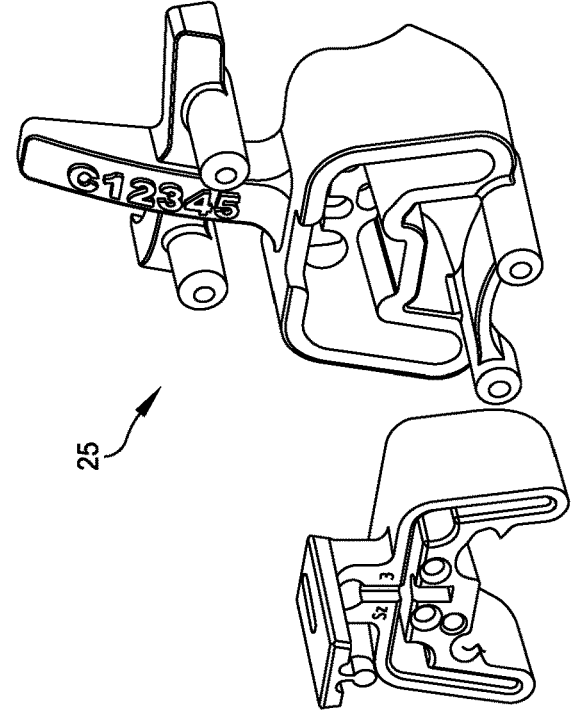
FIG. 6C depicts a perspective view of a medical device that includes a resection guide locator and a resection guide positioned prior to insertion.
Figures 6F, 6G:
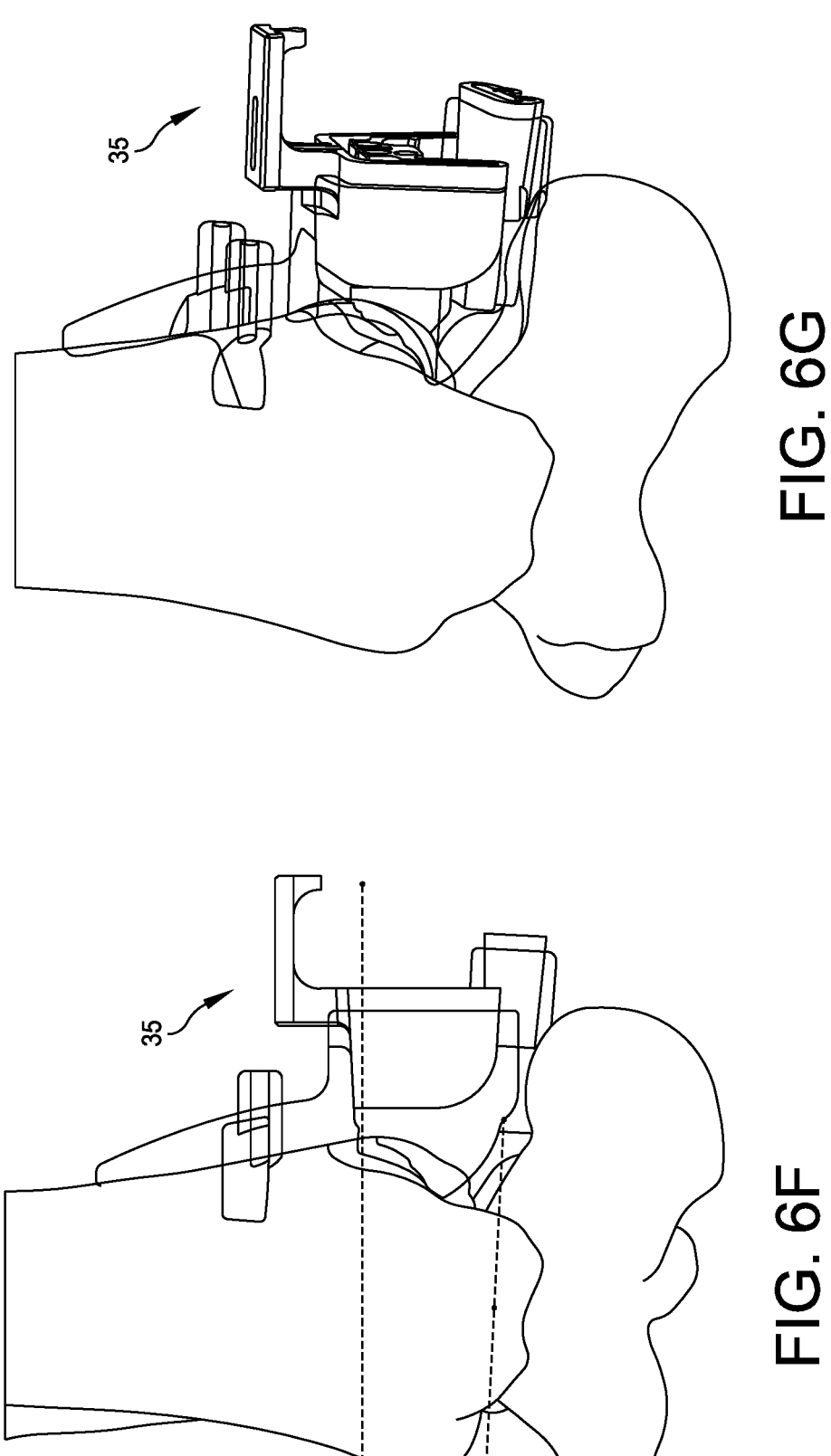
FIG. 6F depicts a perspective view of a medical device that includes a resection guide locator and a resection guide positioned on bone.
FIG. 6G depicts a perspective view of a medical device that includes a resection guide locator and a resection guide positioned on bone.
Figures 7, 8, 9:
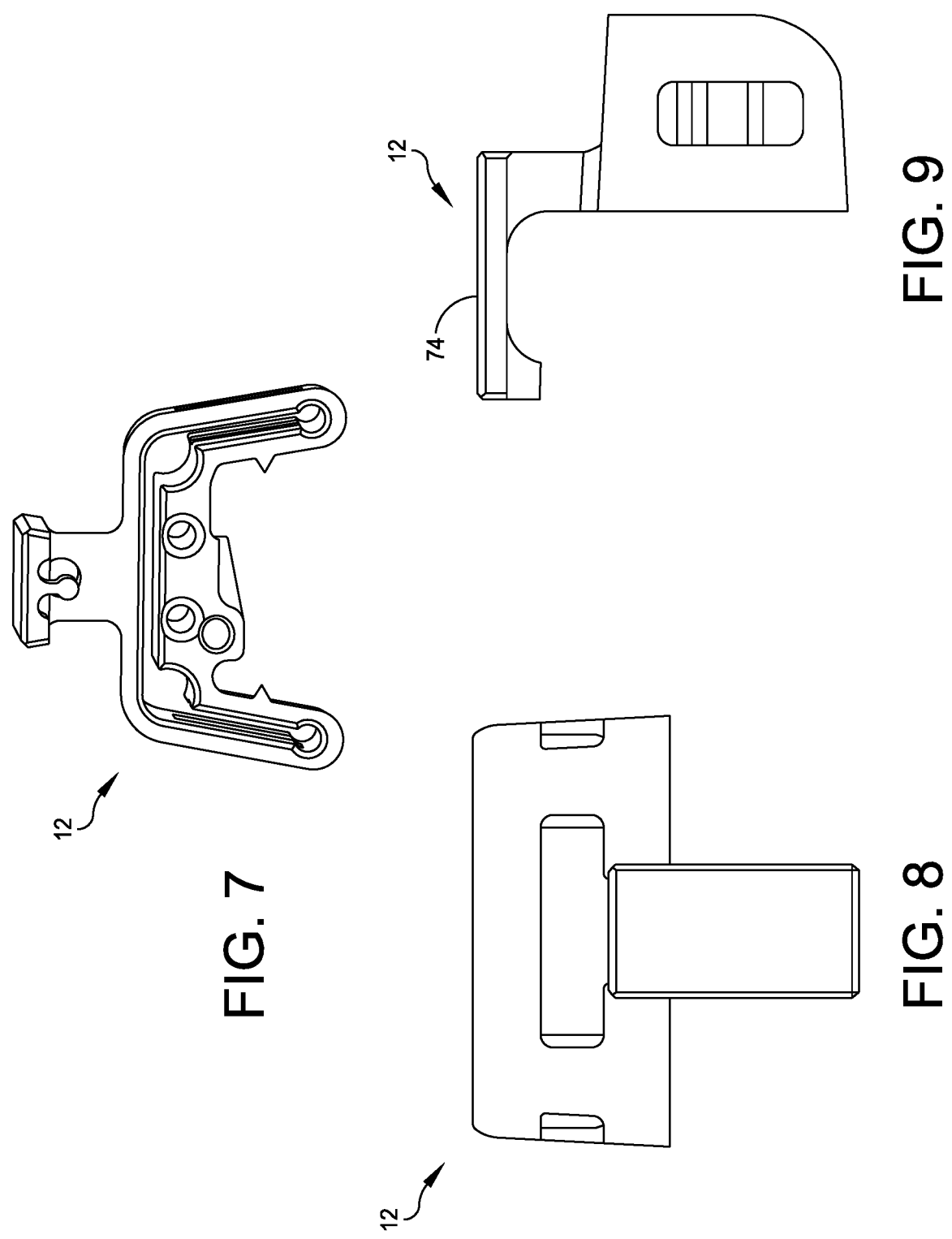
FIG. 7 depicts a front perspective view of a resection guide.
FIG. 8 depicts a top view of a resection guide.
FIG. 9 depicts a side view of a resection guide.
Figure 11:
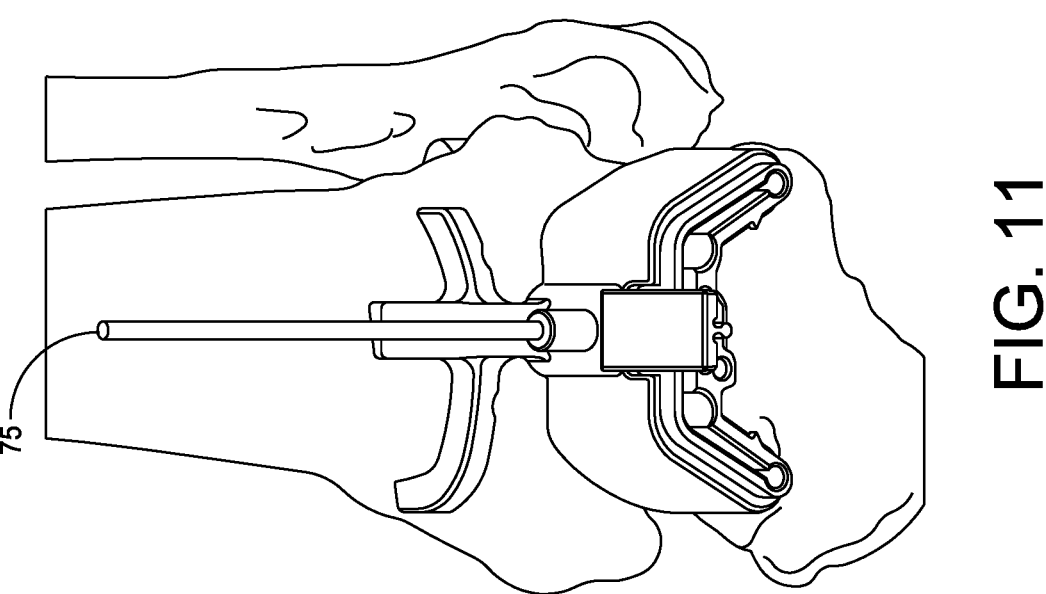
FIG. 11 depicts a top perspective view of a medical device that includes a resection guide locator and a resection guide positioned on bone.
Figure 10:
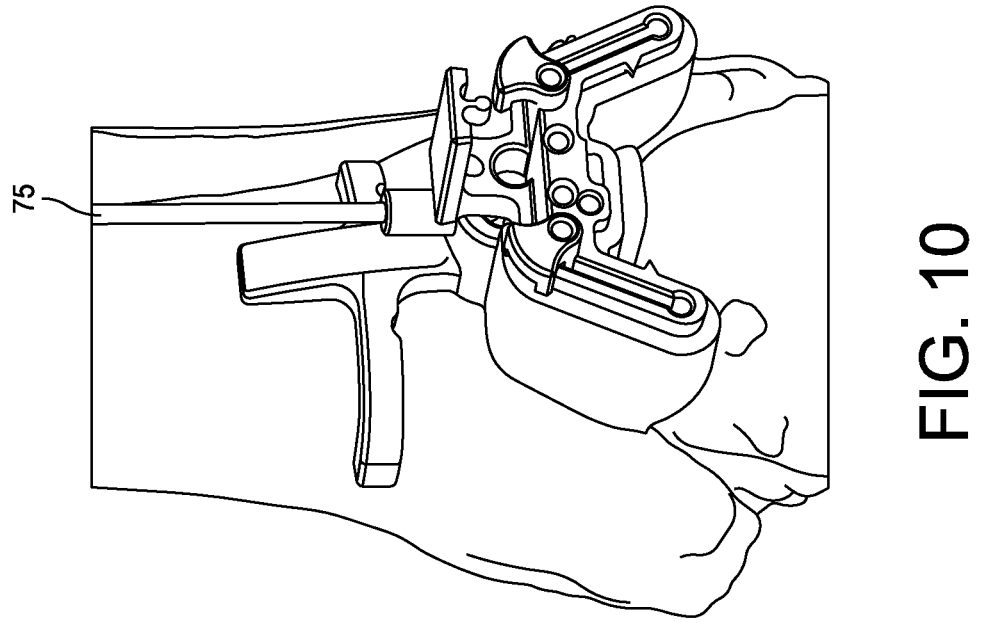
FIG. 10 depicts a side perspective view of a medical device that includes a resection guide locator and a resection guide positioned on bone.

FIGS. 5, 6A-6G, and 7-9 show an embodiment of the resection guide 12. The resection guide 12 can include a body 52 having a similar "U" or winged shape (to the guide receptacle 18) including a central portion 54 and a pair of side portions 56, 58 extending away (e.g., downwardly) from the central portion 54. The body 52 can be configured to fit within the guide receptacle 18 to connect the resection guide 12 to the resection guide locator 10. In an exemplary embodiment, the body 52 includes tapered side surfaces 60, 62 (FIG. 8) and tapered top and bottom surfaces 64, 66 (FIG. 9). The tapered surfaces 60-66 help to guide the body 52 into the guide receptacle 18.

FIG. 5 includes a cross-sectional view of the resection guide 12 inserted into the resection guide locator 10. As shown, the guide receptacle 18 can include tapered surfaces 68 that correspond to the tapered surfaces 60-66 of the body 52 of the resection guide 12, thereby providing a snug press-fit between the resection guide locator 10 and the resection guide 12. The taper may be formed as a narrow taper (e.g., 6 degrees of taper) and have the ability to secure the assembled components by friction as they are press-fit (e.g., like a Morse taper) while wider angles may be used to allow the components to release or be removed more easily.

FIGS. 6A-6B illustrate the resection guide 12 being inserted into the resection guide locator 10. FIGS. 6C-6E illustrate the resection guide 12 being inserted into the resection guide locator 26. FIGS. 6F-6G illustrate the resection guide 12 being inserted into the resection guide locator 36. In one or more of these embodiments, the resection guide 12 may be lightly-pressed to seat. According to some embodiments, the resection guide 12 is not flush with the resection guide locator 10, 26, 36 and may sit approximately 2-3 mm proud.

Further, the guide receptacle 18 can include a clearance 70 such that the resection guide 12 does not necessarily contact the resection guide locator 10 at a back edge 72. The clearance 70, in conjunction with the taper results in a built-in tolerance between the resection guide locator 10 and the resection guide 12 which accommodates manufacturing inaccuracies while consistently achieving a secure press-fit and easy assembly and possible disassembly of the components. Moreover, the taper distributes a load across a large surface area, thereby reducing local stress concentrations associated with many surgical procedures (e.g., impacts due to vibrating saws).

In surgical procedures involving the ankle, an additional talar cut is often performed. In exemplary embodiments, the medical devices 15, 25, 35 may further include features for enabling a corresponding talar cut to be performed. For instance, the medical device 35 having the second resection guide 44 provides an integral tool for performing a talar cut. The additional embodiments may also include features for placement of a talar cutting guide via the placement of one of the disclosed resection guide locators 10, 26, 36.

In one example, the resection guide 12 further comprises a plurality of cutouts, surfaces, and edges that enable the resection guide 12 to provide additional functionality. For instance, the resection guide 12 may include alignment features for ensuring the medical device 15, 25, 35 is correctly positioned relative to a patient. In another example, the resection guide 12 may include features to connect to one or more additional components and/or cutting guides (e.g., in addition to resection guide 12) for use in a surgical procedure, such as for providing pinning locations, alignment features, and/or for performing a talar resection.

Figure 12A:
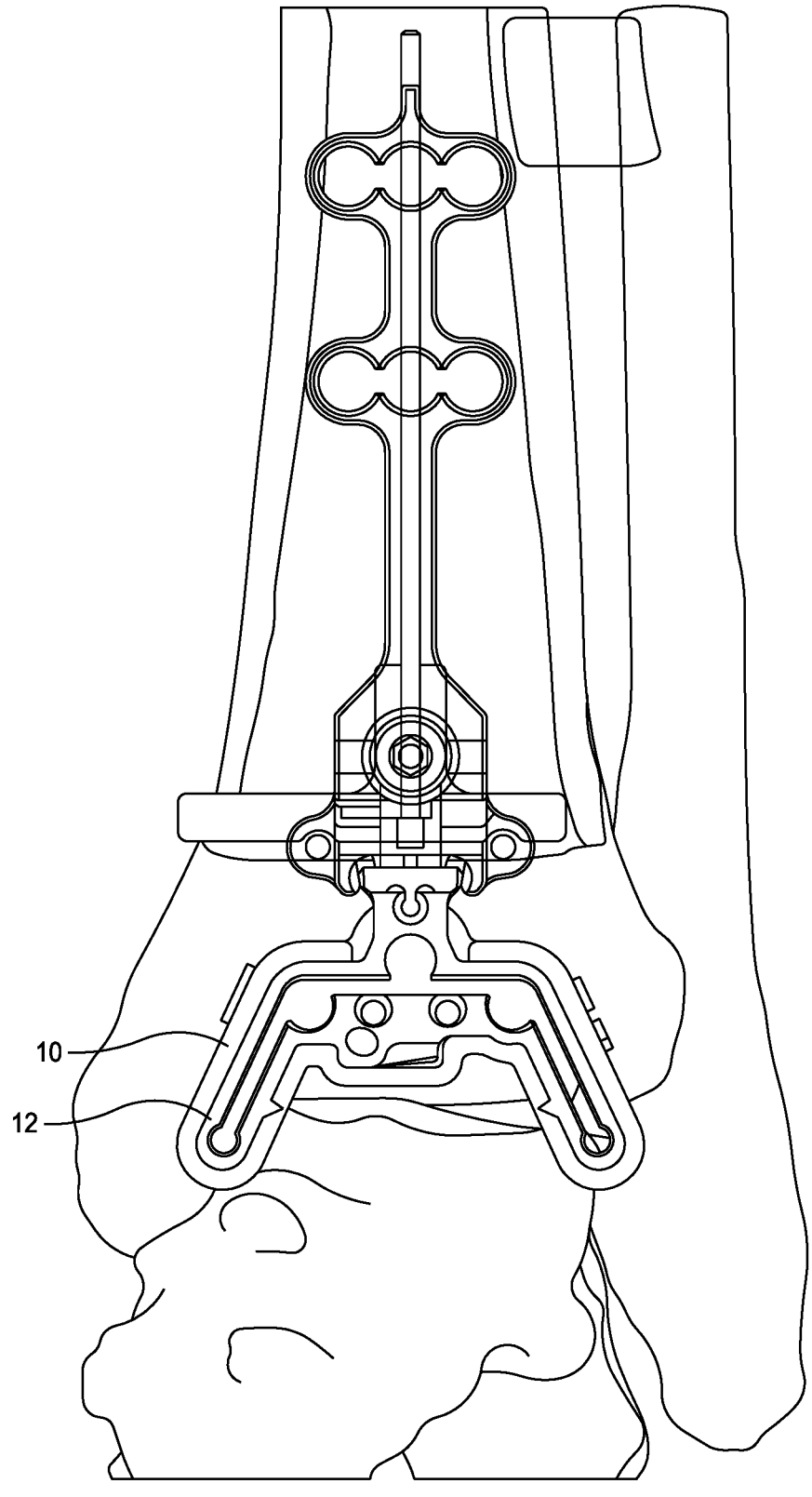
FIG. 12A depicts a front view of a medical device that includes a resection guide locator and a resection guide positioned on bone.
Figure 12B:
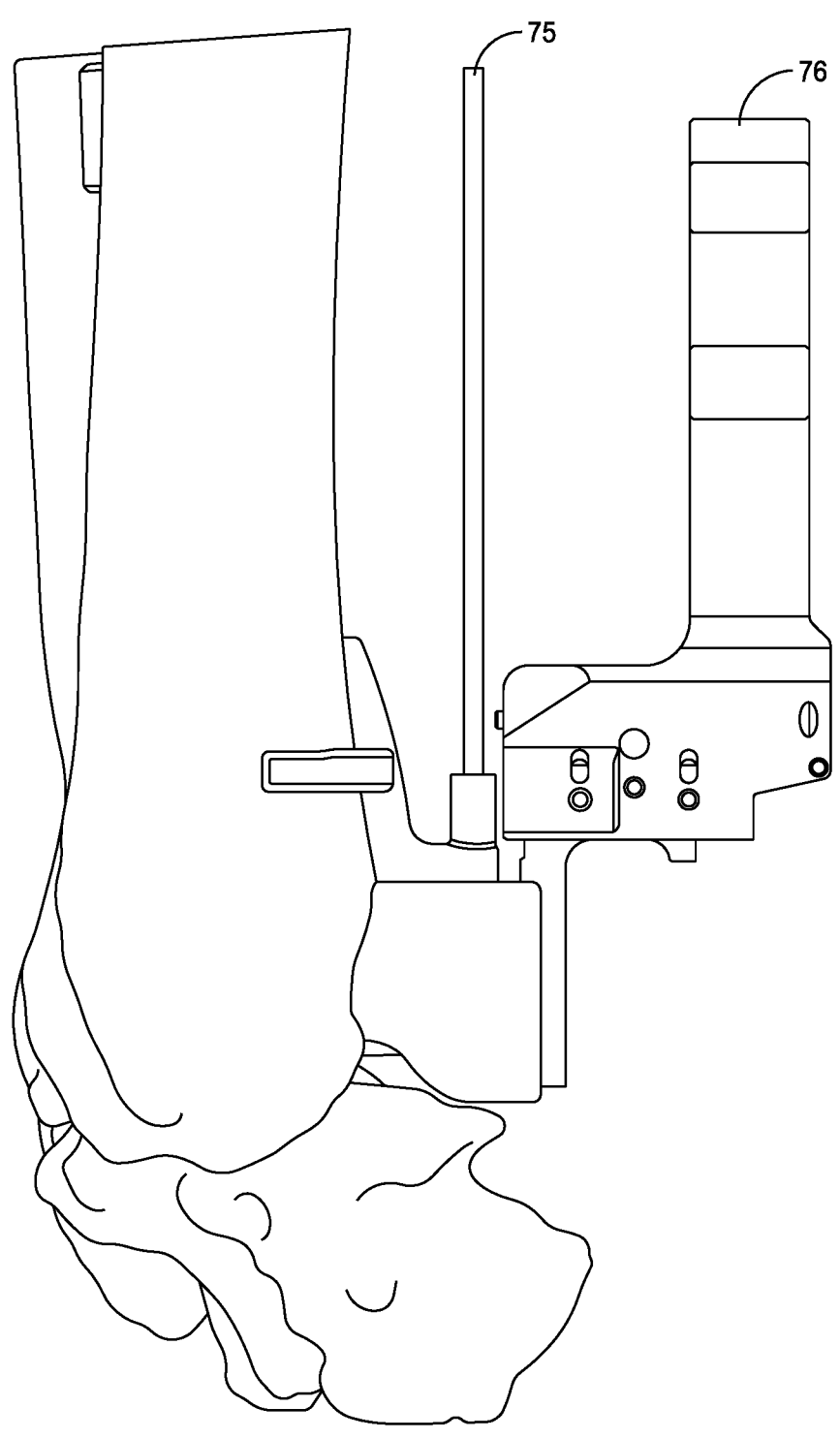
FIG. 12B depicts a side view of a medical device that includes a resection guide locator and a resection guide positioned on bone.
Figures 12C, 12D, 12E, 12F:
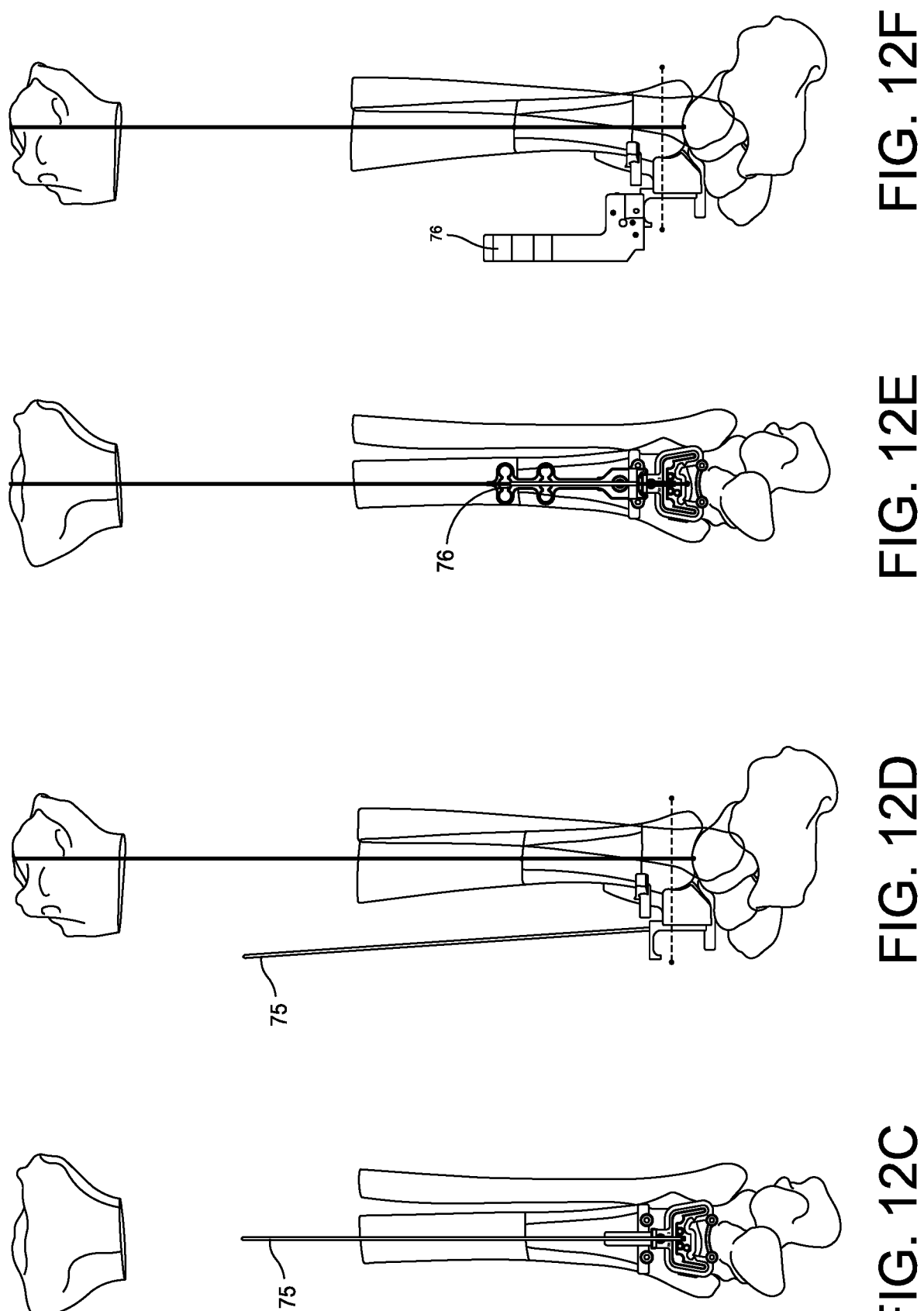
FIG. 12C depicts a front view of a medical device that includes a resection guide locator and a resection guide positioned on bone.
FIG. 12D depicts a side view of a medical device that includes a resection guide locator and a resection guide positioned on bone.
FIG. 12E depicts a front view of a medical device that includes a resection guide locator and a resection guide positioned on bone.
FIG. 12F depicts a side view of a medical device that includes a resection guide locator and a resection guide positioned on bone.
Figures 13A, 13B, 13C:
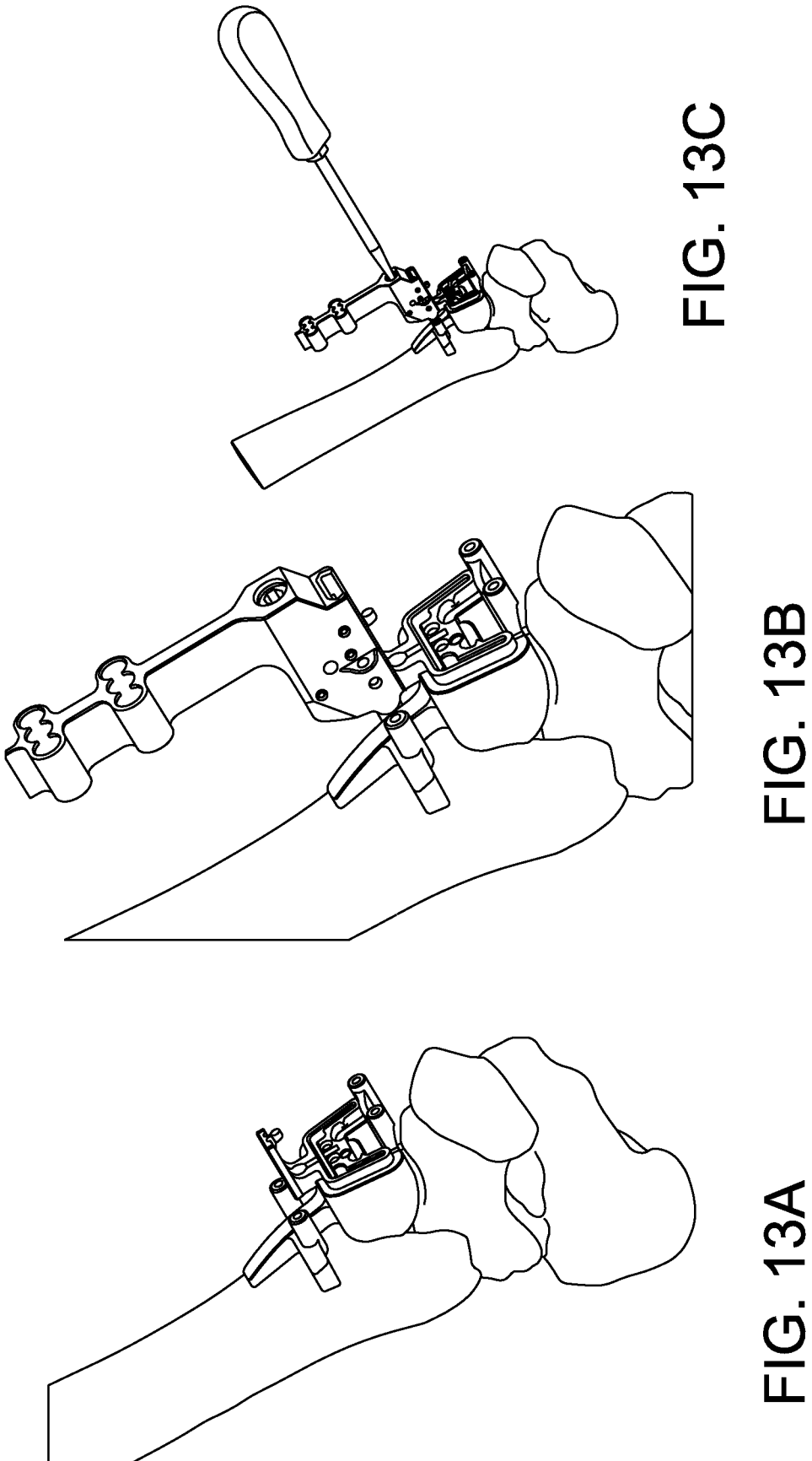
FIG. 13A depicts a side perspective view of an embodiment of a medical device that includes a resection guide locator and a resection guide positioned on bone.
FIG. 13B depicts a side perspective view of an embodiment of a medical device that includes a resection guide locator and a resection guide positioned on bone.
FIG. 13C depicts a side perspective view of an embodiment of a medical device that includes a resection guide locator and a resection guide positioned on bone and an instrument used to secure the components.
Figure 14B:
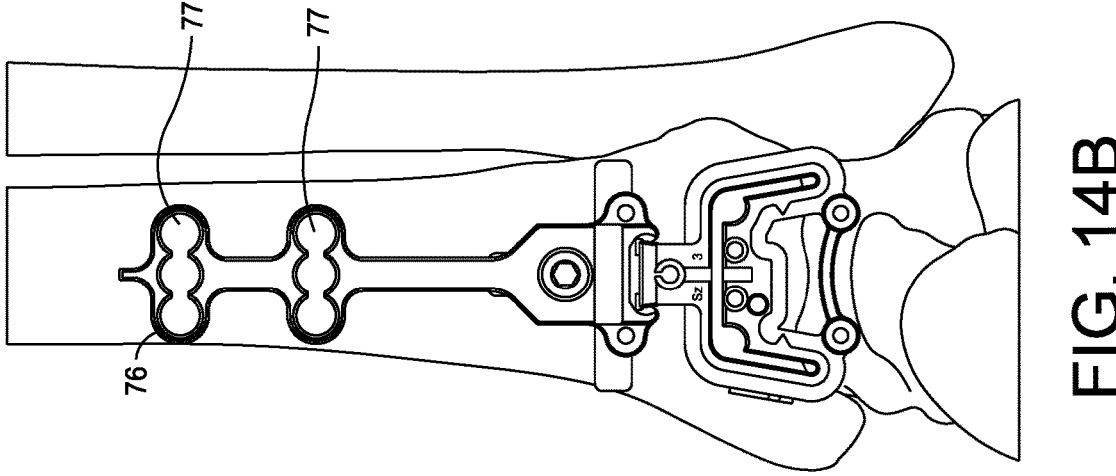
FIG. 14B depicts a front view of an embodiment of a medical device that includes a resection guide locator and a resection guide positioned on bone and an alignment reference component coupled to the resection guide.
Figure 14A:
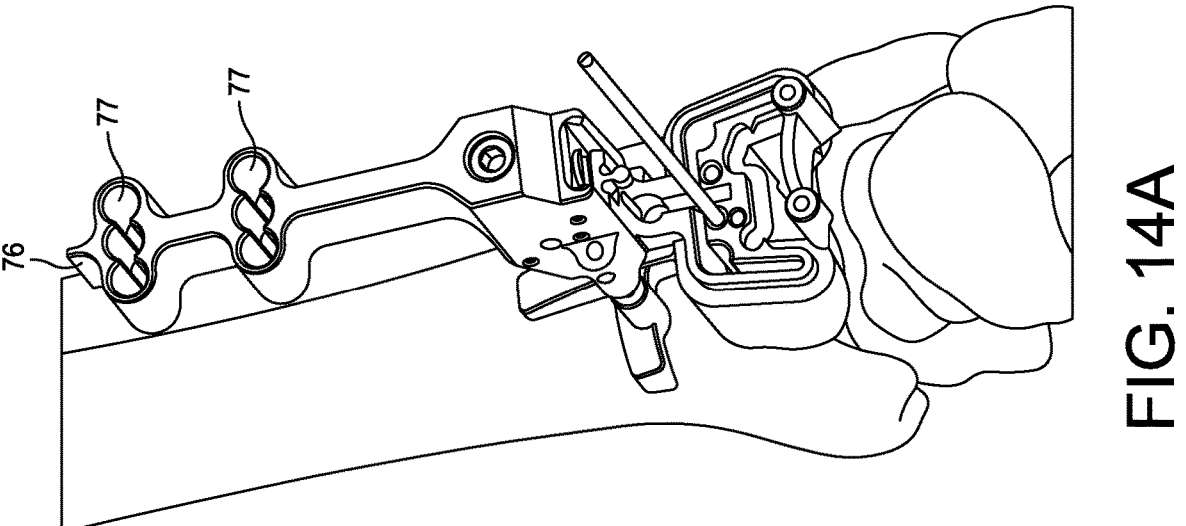
FIG. 14A depicts a perspective view of an embodiment of a medical device that includes a resection guide locator and a resection guide positioned on bone and an alignment reference component coupled to the resection guide.

In one example, the resection guide 12 can include a block 74 for connecting to an alignment reference, such as a component 76, as further shown in FIGS. 12A, 12B, 12E, and 12F, 13A-13C, and 14A-14B. The component 76 may be a conventional alignment reference having rings 77 for fluoroscopic alignment with boundaries of the tibia. FIGS. 13A-13C further illustrate an exemplary attachment process for securing the component 76 to the resection guide 12. The block 74 may include a dovetail connection or other connector for securing the resection guide 12 to the component 76 via a sliding, press-fit, and/or fastener connection.

Figure 15B:
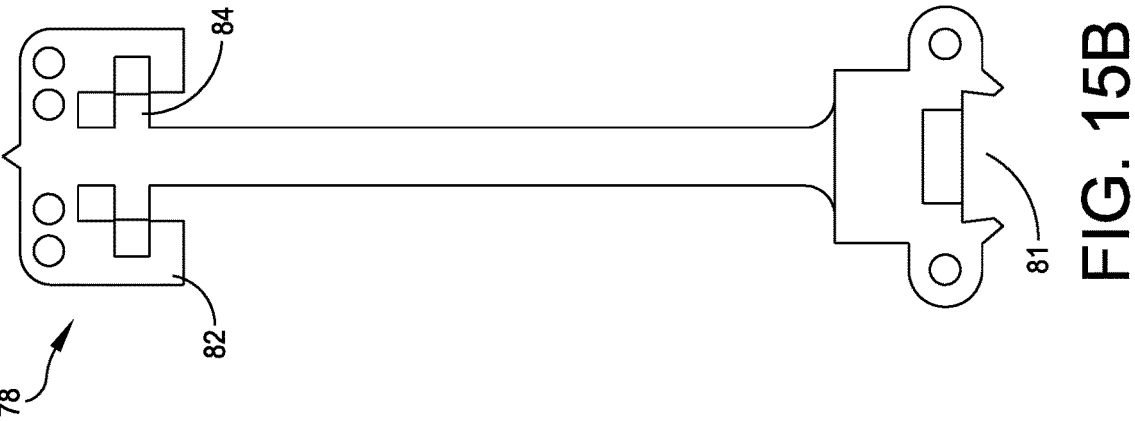
FIG. 15B depicts a front view of an alignment reference component.
Figure 15A:
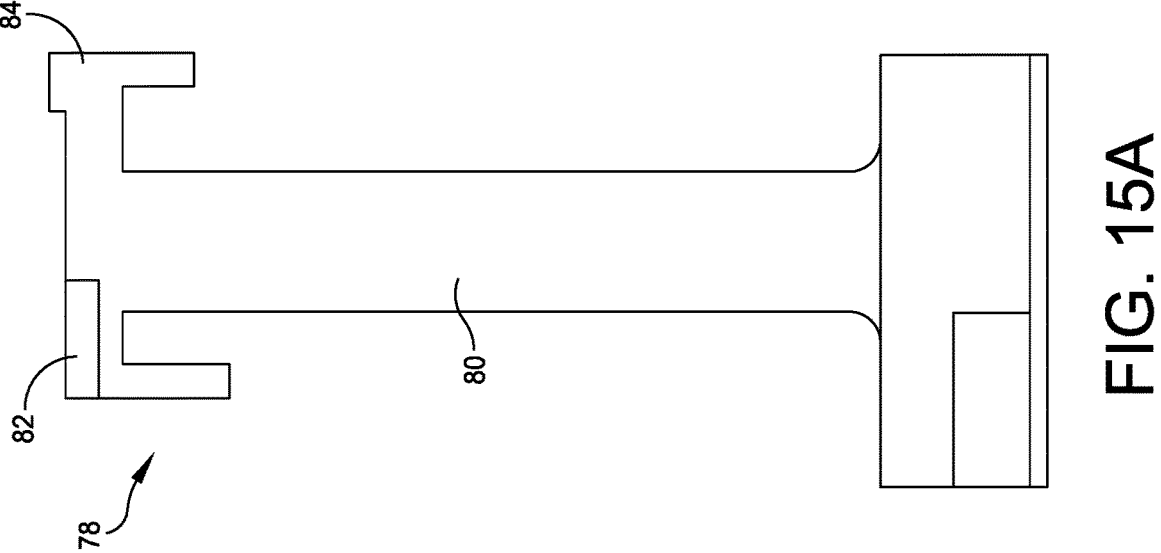
FIG. 15A depicts a side view of an embodiment of an alignment reference component.

FIGS. 15A and 15B illustrate another reference component 78 that may be attached to the block 74. The reference component 78 includes a main post 80, a rear portion 82 on a first side of the post 80 and a front portion 84 on a second, opposite side of the post 80. When viewed from a straight-on angle, the rear portion 82 and the front portion align to form the checkerboard pattern shown in FIG. 15B. In this way, the reference component 78 can provide an alignment check (e.g., fluoroscopically) in two dimensions (e.g., vertically via the post 80 and in the sagittal plane via alignment of the rear portion 82 and front portion 84 to match the pattern shown in FIG. 15B). The reference component 78 may also include a connection feature 81, such as a dovetail connector for securing to the block 74.

An alignment check may be used to determine a position and/or orientation of an element of a system, such as a medical device and/or components thereof, in multiple dimensions. In an embodiment, an alignment check may include a cluster of radio-opaque spheres which can be tracked in a cluster to indicate orientation and/or position of medical device and/or component with a computer aided system. For example, an alignment check may include a cluster of radio-opaque spheres positioned within a medical device for which the alignment is being determined. The radio-opaque spheres can be tracked as a cluster to indicate orientation and position of the device with a computer aided system. In particular, the relative position of the radio-opaque spheres to each other may indicate the positioning and/or orientation of the device when using a computer aided system.

In some embodiments, the medical device 15 includes an attachment mechanism for a vertical Kirchner wire ("k-wire") 75 or some other elongate straight slender rod to be used as a physical visual reference. For instance, FIGS. 10, 11 and 12A-12D illustrate an embodiment including the Kirchner wire 75 for aligning the resection guide locator 10 with respect to the patient and providing a visual check. FIGS. 10, 11, 12A, and 12B illustrate an embodiment in which the Kirchner wire 75 attaches to the resection guide locator 10 and FIGS. 12C and 12D illustrate an embodiment in which the Kirchner wire 75 attaches to the block 74 of the resection guide 12.

Figures 16A, 16B, 16C, 16D, 16E:
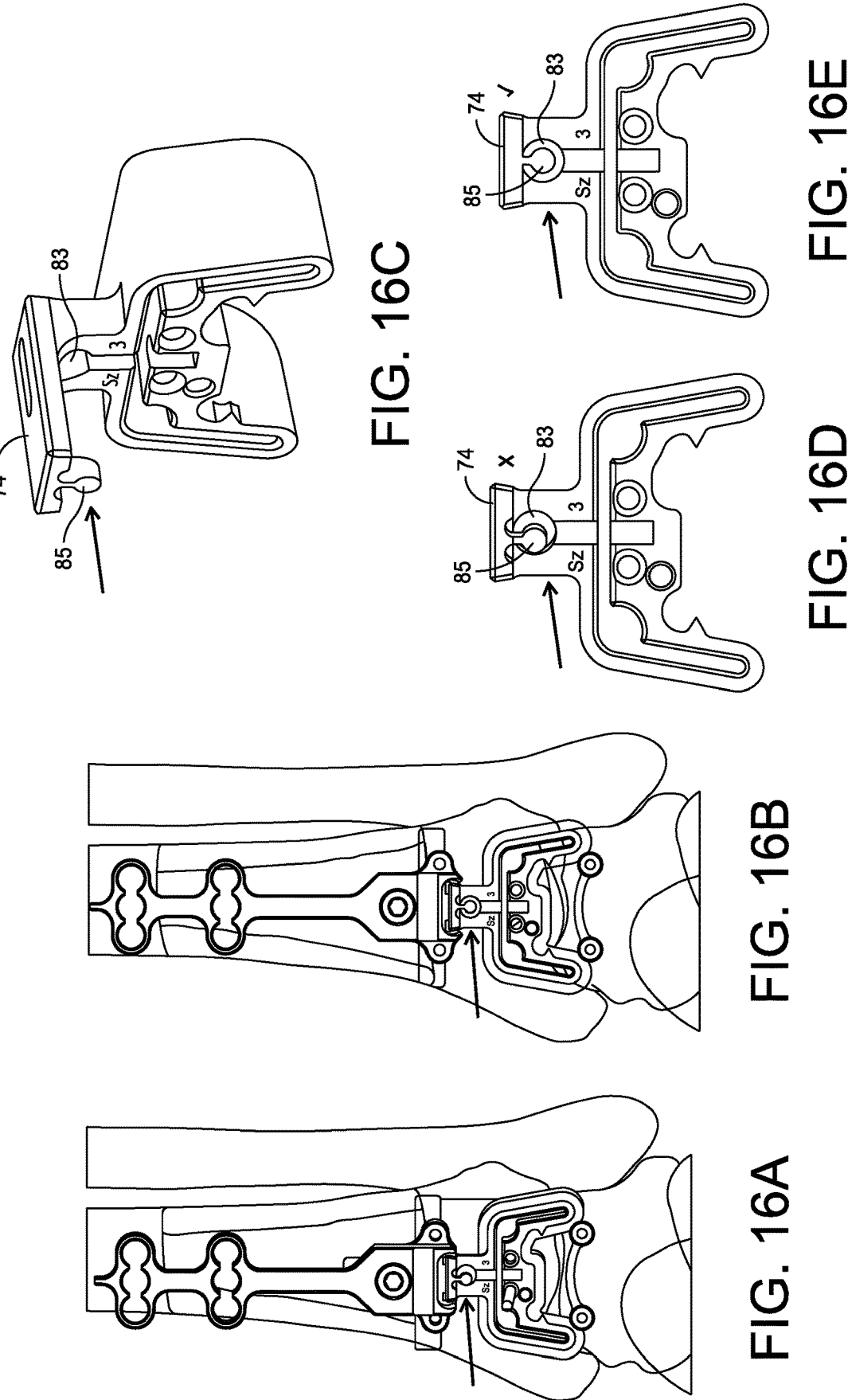
FIG. 16A depicts a front view of an embodiment of a medical device that includes a resection guide positioned on bone and an alignment reference component coupled to the resection guide.
FIG. 16B depicts a front view of an embodiment of a medical device that includes a resection guide positioned on bone and an alignment reference component coupled to the resection guide.
FIG. 16C depicts a side perspective view of an embodiment of a medical device that includes a resection guide.
FIG. 16D depicts a front perspective view of an embodiment of a medical device that includes a resection guide.
FIG. 16E depicts a front view of an embodiment of a medical device that includes a resection guide.

In some embodiments, the resection guide 12 includes one or more built-in or integral alignment features. FIGS. 16A-16E illustrate the block 74 may further include a cavity 83 at a first side of the block 74 and a projection 85 at a second side of the block 74. The cavity 83 and the projection 85 may include a similar shape and be positioned such that in a straight-on view, the projection 85 is aligned in a center of the cavity 83, as seen in FIGS. 16B and 16E. If the resection guide 12 is angled and not properly aligned, the projection 85 will not be centered with respect to the cavity 83, as shown in FIGS. 16A and 16D. The block 74 may thus provide a fluoroscopic and/or visual alignment feature for positioning the resection guide locator 10 (or 26 or 36) and resection guide 12.

Figure 17A:
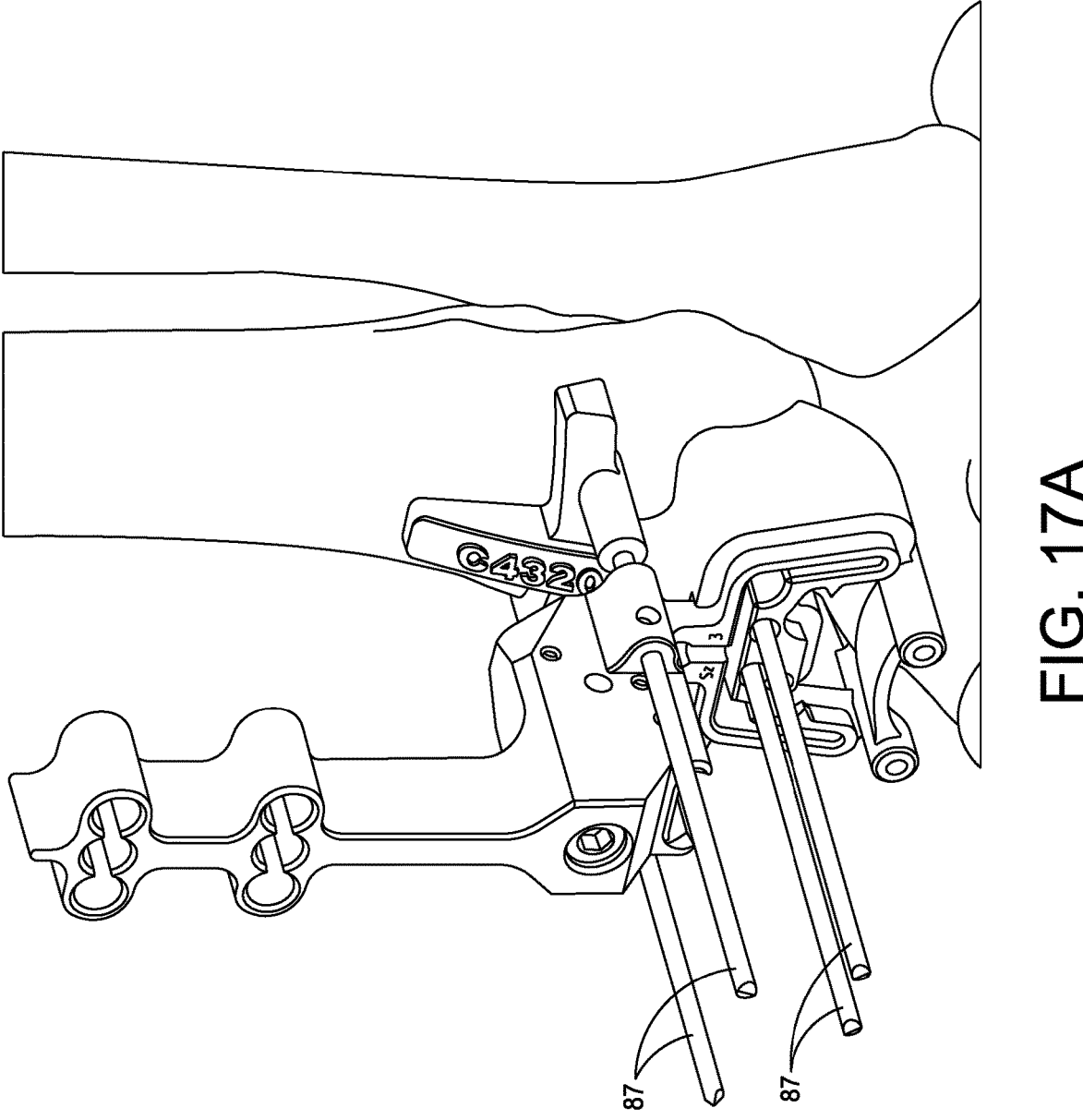
FIG. 17A depicts a side perspective view of an embodiment of a medical device that includes a resection guide locator and a resection guide positioned on bone and an alignment reference component coupled thereto.
Figure 17B:
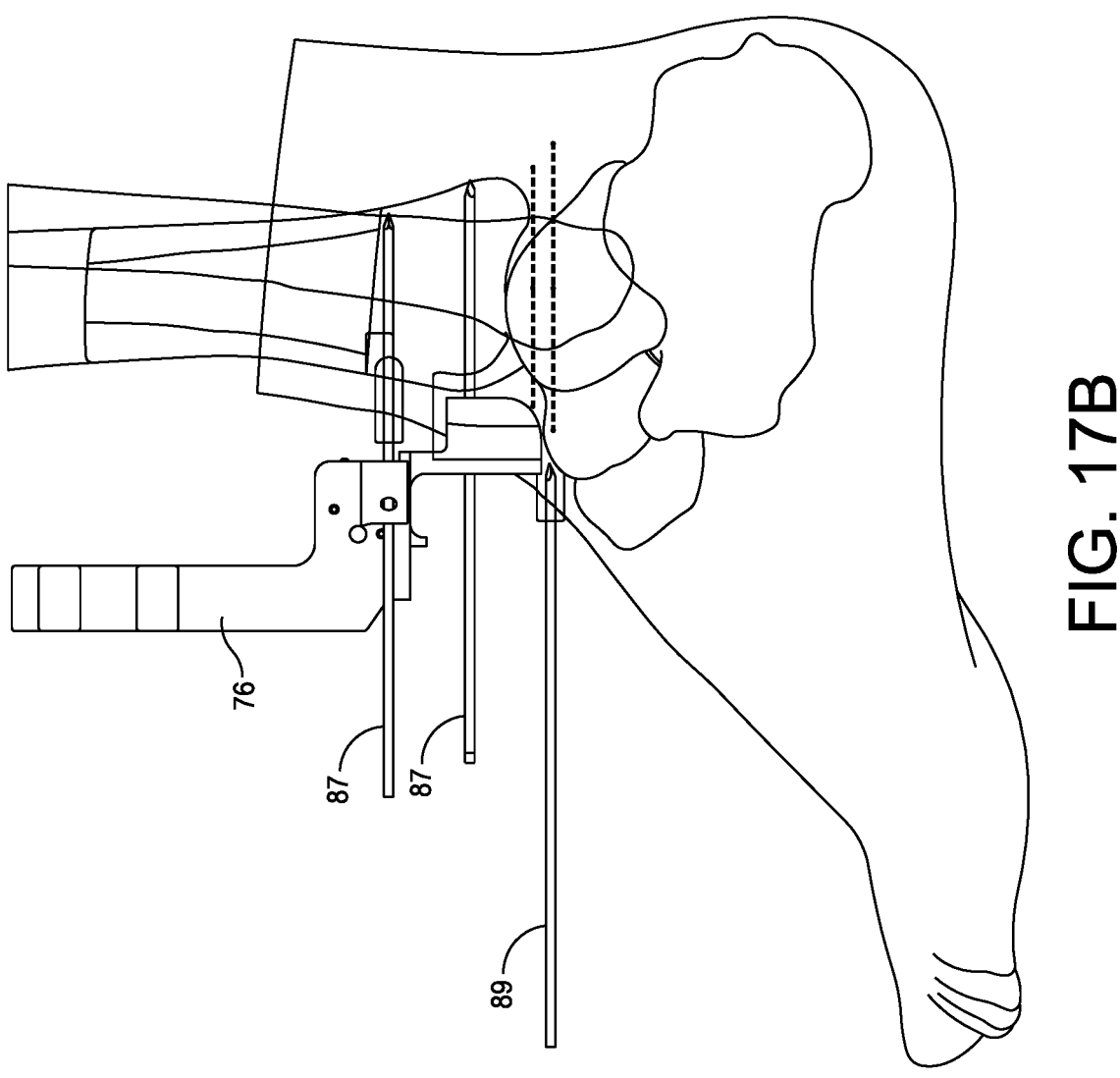
FIG. 17B depicts a side perspective view of an embodiment of a medical device that includes a resection guide locator and a resection guide positioned on bone and an alignment reference component coupled thereto.
Figures 17C, 17D, 17E:
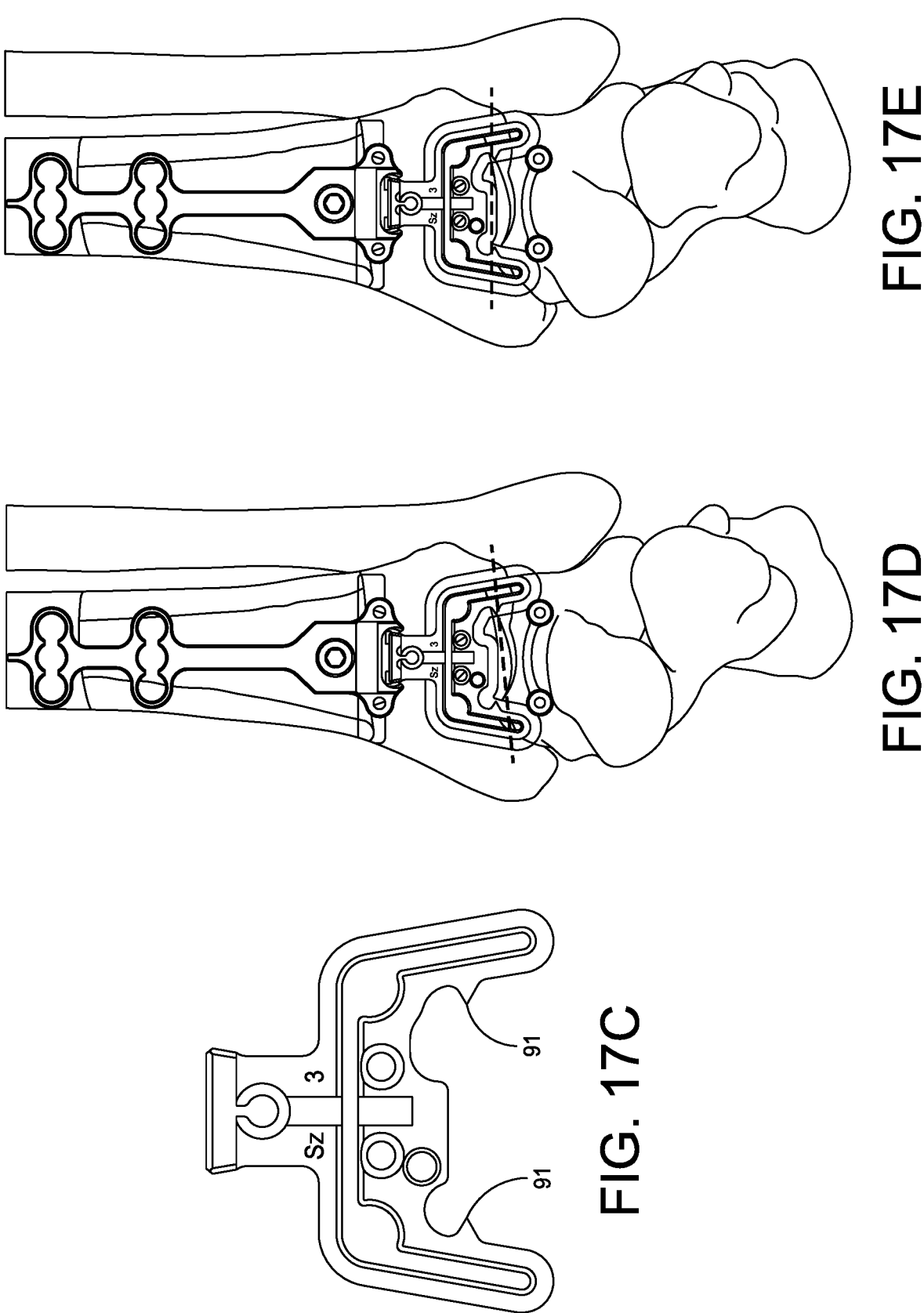
FIG. 17C depicts a front view of an embodiment of a medical device that includes a resection guide.
FIG. 17D depicts a front view of an embodiment of a medical device that includes a resection guide positioned on bone and an alignment reference component coupled thereto.
FIG. 17E depicts a front view of an embodiment of a medical device that includes a resection guide positioned on bone and an alignment reference component coupled thereto.
Figure 17G:
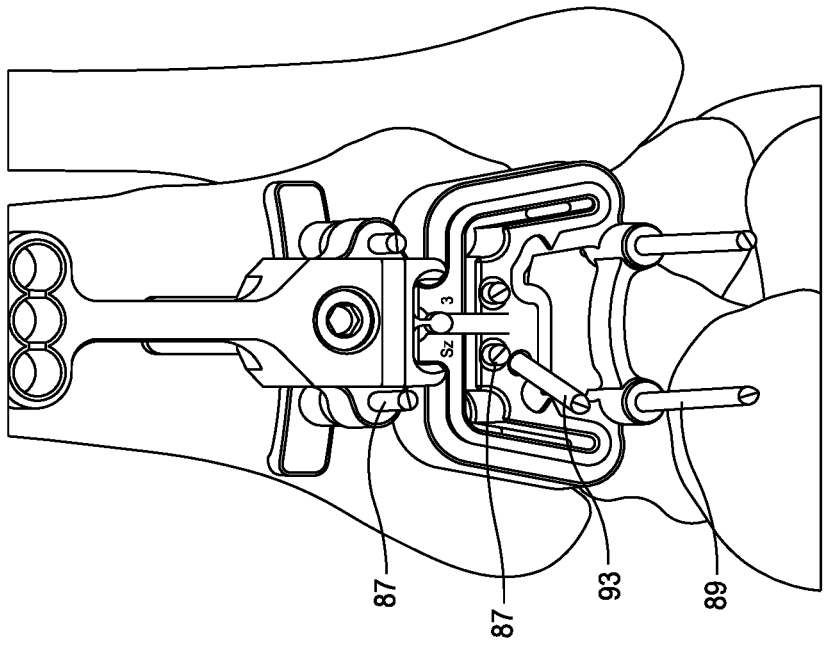
FIG. 17G depicts a front perspective view of an embodiment of a medical device that includes a resection guide locator and a resection guide positioned on bone and an alignment reference component coupled thereto.
Figure 17F:
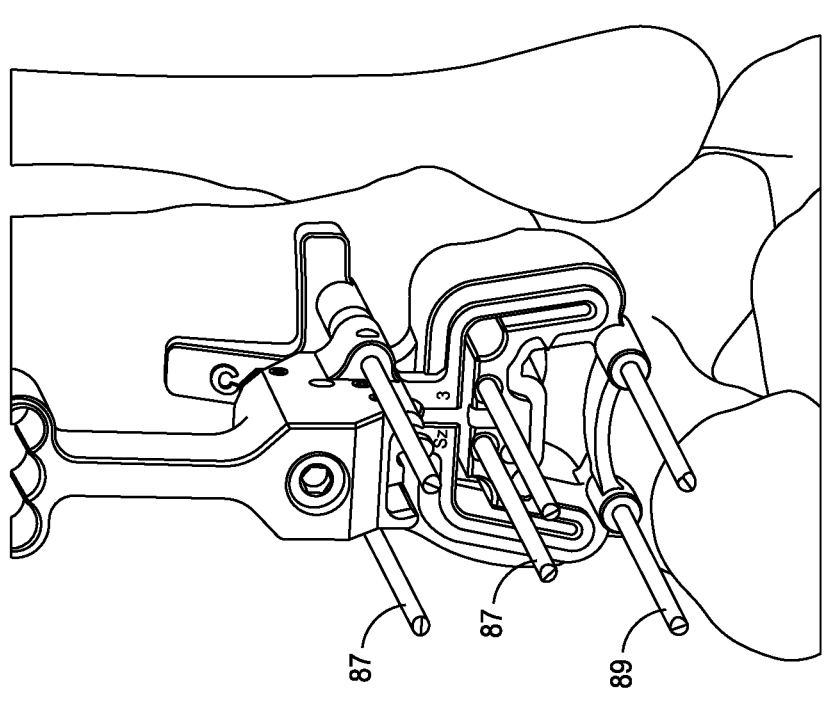
FIG. 17F depicts a side perspective view of an embodiment of a medical device that includes a resection guide locator and a resection guide positioned on bone and an alignment reference component coupled thereto.

The disclosed alignment features may be used separately or in combination to manually position the resection guide locator 10 (or 26 or 36) with respect to the patient. As shown in FIGS. 17A and 17B, the resection guide locator 26 (while 26 is shown, the same may equally apply to resection guide locators 10 and 36) can then be pinned to the patient using pins or wires 87 placed through corresponding holes in the resection guide locator 26 and/or resection guide 12. As shown in FIGS. 17C-17E the resection guide 12 may also include joint line reference cues 91 for aligning the patient's talus with the resection guide locator 26 to enable pins to be inserted into talar pin guides 32, 34 and into a proper location of the talus. For example, a surgeon may position the talus in the desired flexion angle, and with the desired varus-valgus alignment of the joint line relative to the reference cues 91, before placing the talus pins 89. FIGS. 17F and 17G include additional illustrations showing pins or wires 87 inserted into the tibia and wires into the talus 89. FIG. 17G further illustrates an angled pin 93 for further securing the resection guide 12.

Figures 18A, 18B:
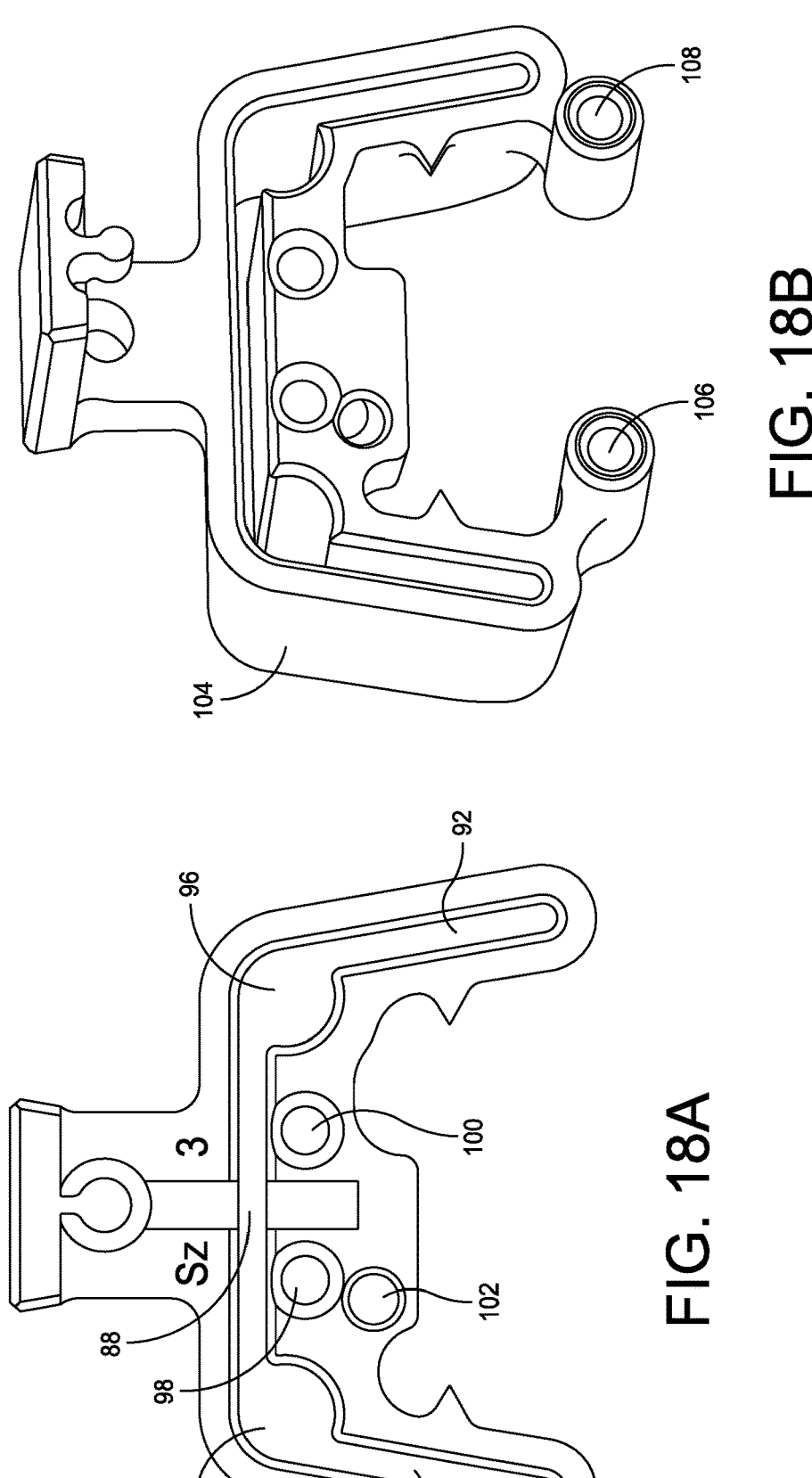
FIG. 18A depicts a front view of an embodiment of a medical device that includes a resection guide.
FIG. 18B depicts a perspective view of an embodiment of a medical device that includes a resection guide.

FIG. 18A shows an embodiment of the resection guide 12. The resection guide 12 includes a receptacle 86 for receiving one or more additional components of a surgical system. According to some embodiments, the receptacle 86 can also serve a surgical function in that it can be a resection slot for receiving a tool (e.g., a saw) during an operation. The receptacle 86 can thus be configured as a multi-purpose feature for providing a functional slot for use in the operation and for providing attachment features for connecting other components used during the operation.

The receptacle 86 can comprise a "U" or winged shape generally following a shape of the body 52. For example, the receptacle 86 can comprise a central portion 88 and a pair of side portions 90, 92. The receptacle 86 can include one or more openings holes 94, 96, 98, 100, 102 for providing a drilling location, pinning location, attachment location, etc. For instance, the receptacle 86 can include a pair of holes 94, 96 at a junction portion between the central portion 88 and side portions 90, 92 for drilling holes at the junction of two resection cuts. The resection guide 12 may also include holes 98, 100, 102 for receiving pins or wires 84, including angled hole 102 for receiving the angled pin 93.

FIG. 18B is another embodiment of a resection guide 104 having a pair of talar pin guides 106, 108 formed in solid extension portions of the body 52 (e.g., instead of the talar pin guides 32, 34 in the resection guide locator 26). The resection guide 104 may include similar features to the resection guide 12.

Figures 18C, 18D:
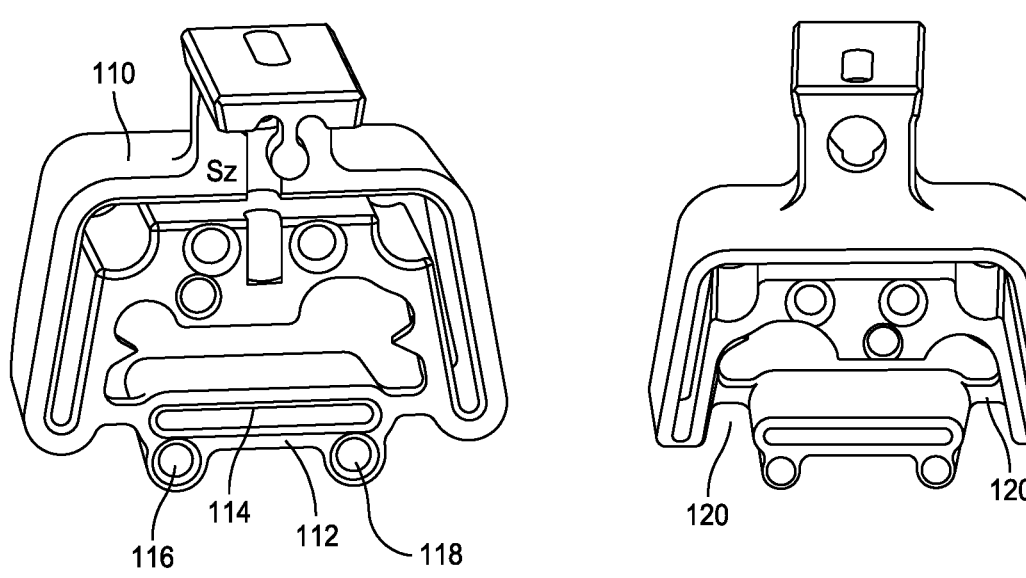
FIG. 18C depicts a perspective view of an embodiment of a medical device that includes a resection guide.
FIG. 18D depicts a perspective 4view of an embodiment of a medical device that includes a resection guide.
Figure 18E:
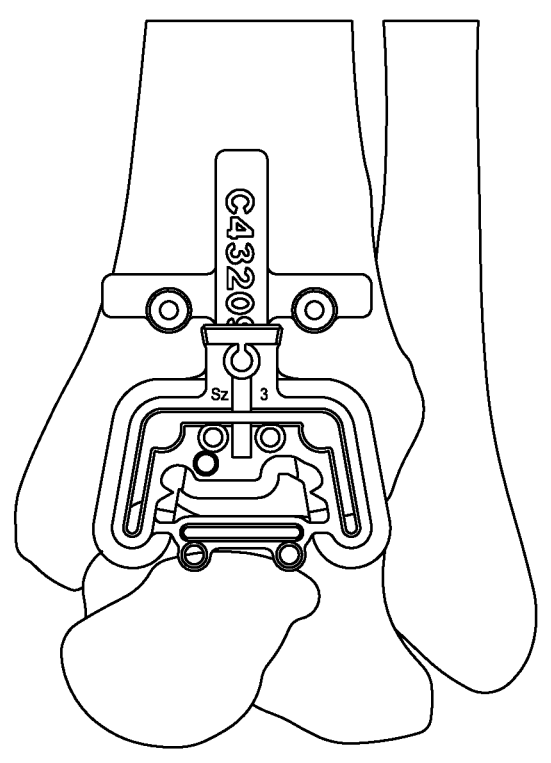
FIG. 18E depicts a front view of an embodiment of a medical device that includes a resection guide locator and a resection guide positioned on bone.

FIGS. 18C-18E is another embodiment of a resection guide 110. The resection guide 110 is similar to the resection guide 12 and further includes an extension 112 including a talar cut slot 114. The extension 112 may also include one or more talar pin guides 116, 118. The resection guide 110 thus provides a combined resection guide for cutting the tibia and the talus using one guide. FIG. 18D shows a rear view of the resection guide 110, further including a pair of cutouts 120 for accommodating a portion of the resection guide 10 such that only a portion of the resection guide 110 is inserted into the guide receptacle 18 of the resection guide locator 10.

Figures 19A, 19B:
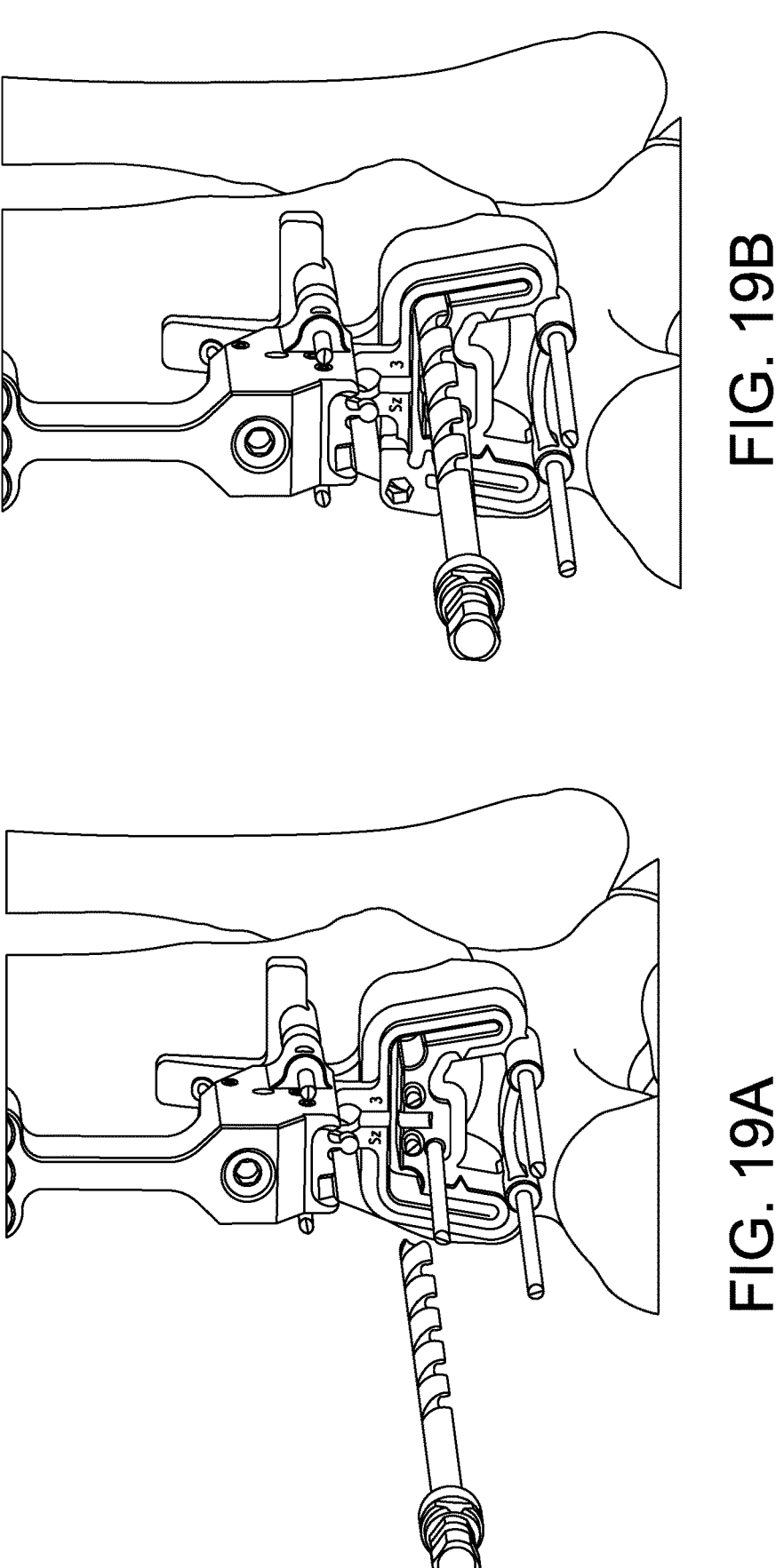
FIG. 19A depicts a side perspective view of an embodiment of a medical device that includes a resection guide locator and a resection guide positioned on bone and an alignment reference component coupled thereto and an instrument used to drill holes in bones through the resection guide.
FIG. 19B depicts a side perspective view of an embodiment of a medical device that includes a resection guide locator and a resection guide positioned on bone and an alignment reference component coupled thereto and an instrument used to drill holes in bones through the resection guide.

After a selected resection guide locator 10, 26, 36 and resection guide 12, 104, 110 is selected and pinned to the patient, a surgical procedure may include cutting and/or drilling to perform resection cuts. For instance, the surgeon may drill into the holes 94, 96, as shown in FIGS. 19A and 19B and subsequently perform resection cuts following the slots adjacent to the holes 94, 96. In some embodiments, the disclosed devices may further include corner protectors 122, 124 that are inserted into the drilled-out holes corresponding to the holes 94, 96. The corner protectors 122, 124 may help to limit resection cuts to entering the drilled-out holes but not going further into the bone.

Figure 20A:
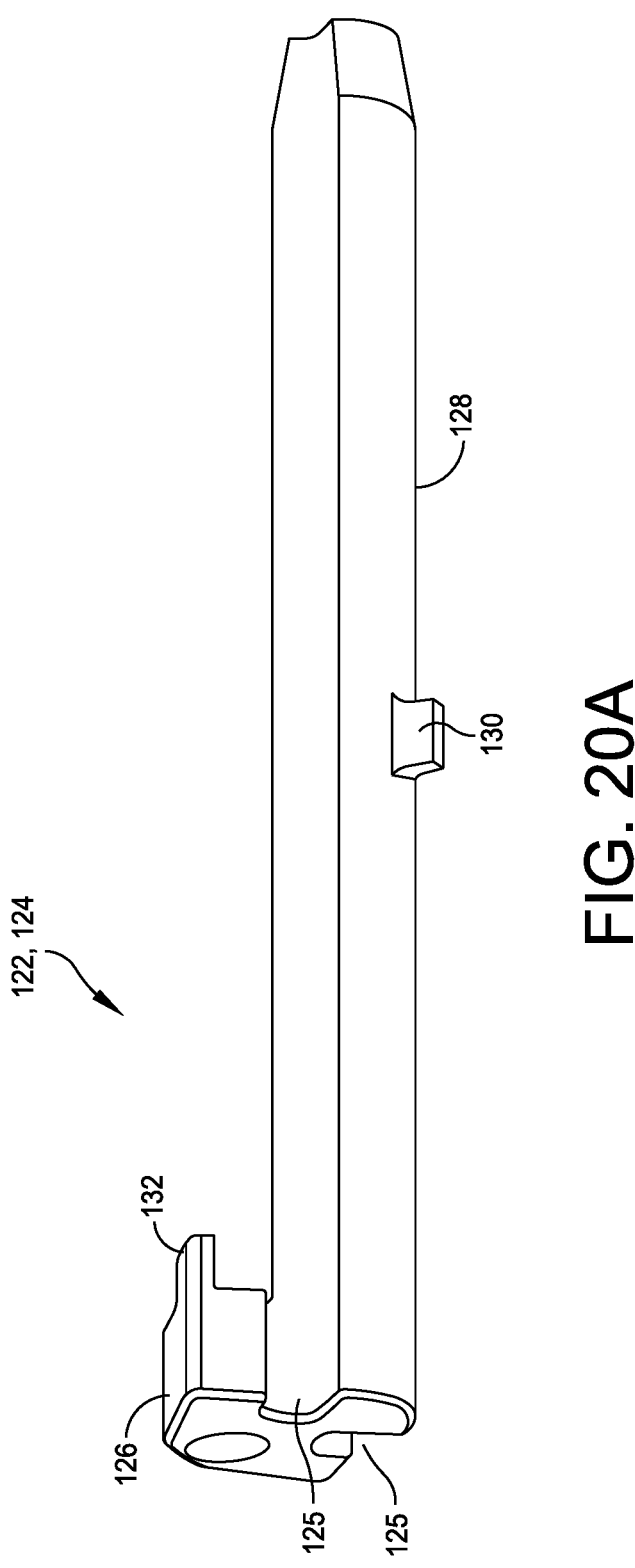
FIG. 20A depicts a side perspective view of an embodiment of a corner protector configured to be connected to a resection guide.
Figures 20B, 20C, 20D:
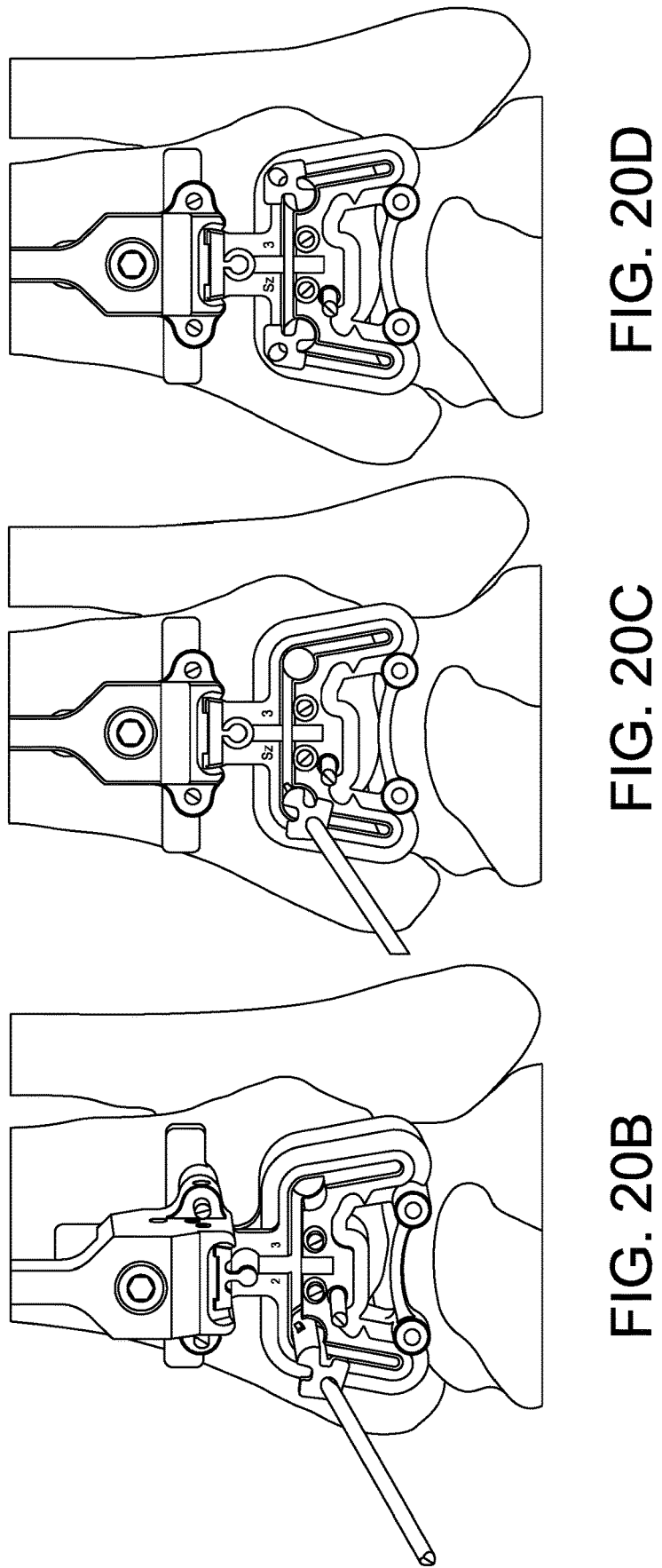
FIG. 20B depicts a perspective view of an embodiment of a medical device that includes a resection guide locator, a resection guide, and an alignment reference component coupled to bone and a corner protector positioned in the resection guide.
FIG. 20C depicts a front perspective view of an embodiment of a medical device that includes a resection guide locator, a resection guide, and an alignment reference component coupled to bone and a corner protector positioned in the resection guide.
FIG. 20D depicts a front view of an embodiment of a medical device that includes a resection guide locator, a resection guide, and an alignment reference component coupled to bone.
Figure 20F:
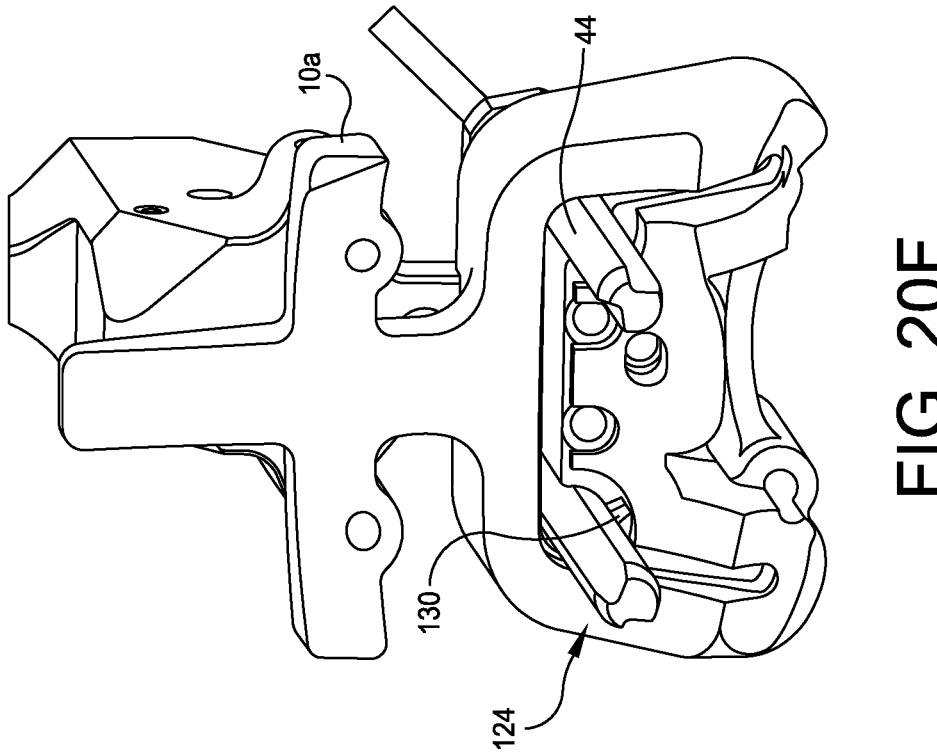
FIG. 20F depicts a back perspective view of an embodiment of a medical device that includes a resection guide locator, a resection guide, and an alignment reference component coupled to each other and a corner protector positioned in the resection guide.
Figure 20E:
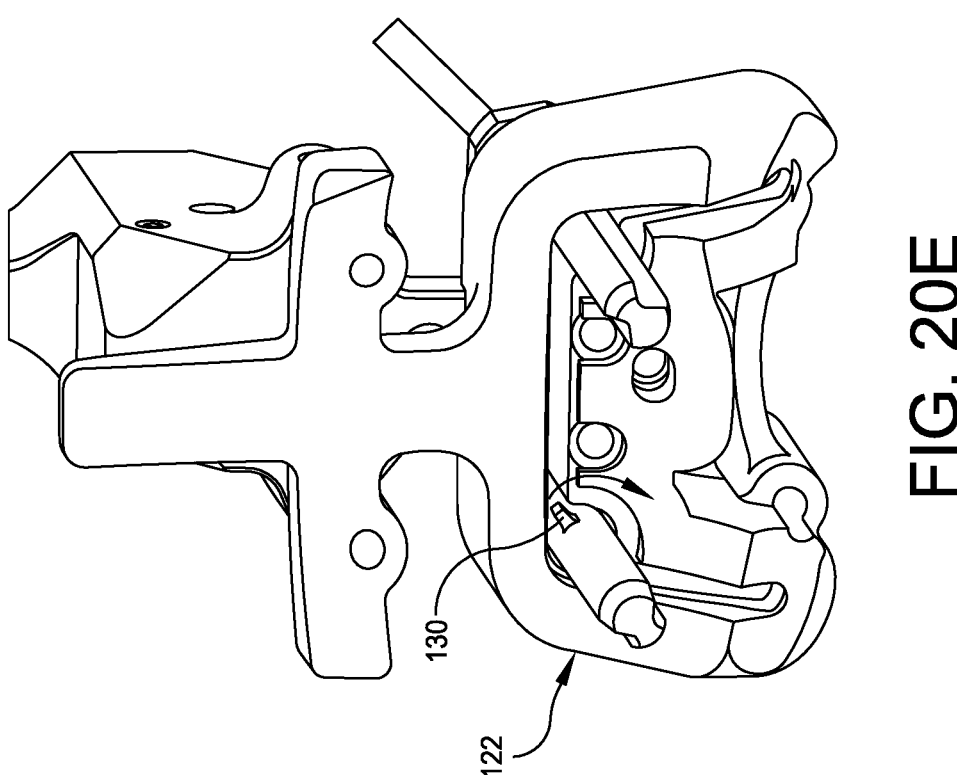
FIG. 20E depicts a back perspective view of an embodiment of a medical device that includes a resection guide locator, a resection guide, and an alignment reference component coupled to each other and a corner protector positioned in the resection guide.
Figures 21A, 21B:
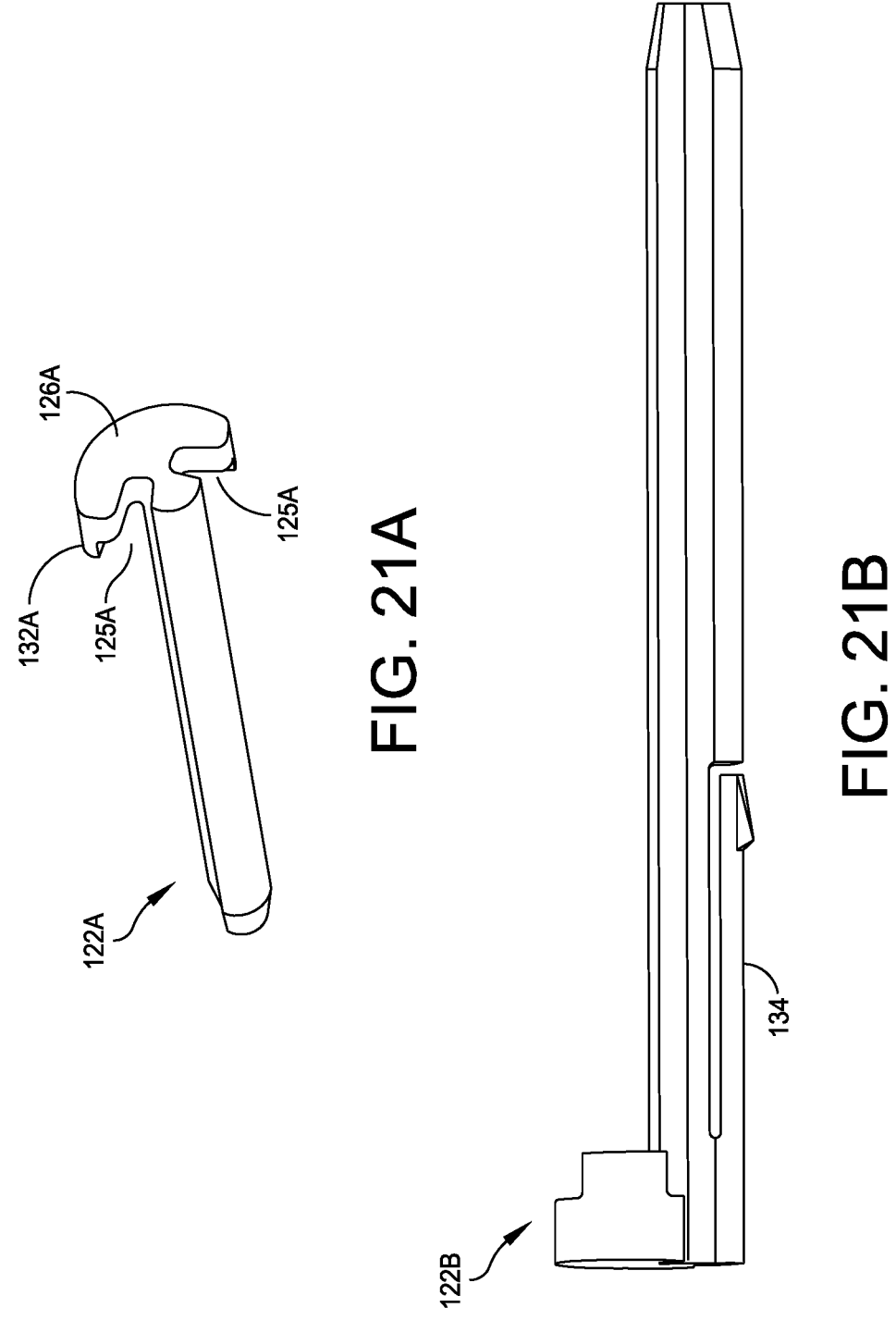
FIG. 21A depicts a side perspective view of an embodiment of a corner protector.
FIG. 21B depicts a side view of an embodiment of a corner protector.
Figure 21C:
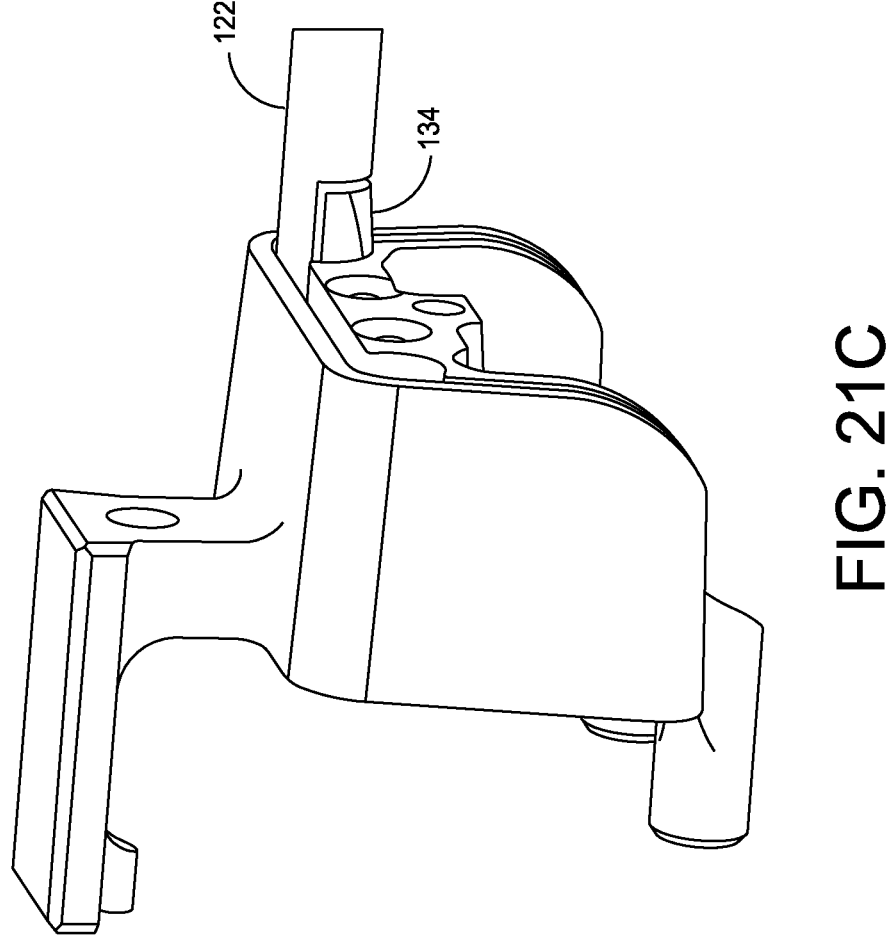
FIG. 21C depicts a side perspective view of an embodiment of a resection guide with a corner protector positioned therethrough.

FIGS. 20A-20F illustrate a first embodiment of corner protectors 122, 124 (also referred to as corner protector pegs) configured to be connected to the resection guide 12 (or other disclosed resection guide). In an exemplary embodiment, the corner protectors 122, 124 block saw excursion deeper into the bone during a surgical procedure. For example, the corner protectors 122, 124 can include notches or grooves 125 along the shaft 128 of the corner protectors 122, 124 so that sawing can go all the way up to a tangent on the drilled out corner of the resection guide 12, but not further. The corner protectors 122, 124 can be configured to lock in place through insertion into a portion of the receptacle 86. For instance the corner protectors 122, 124 can include an elongated stem 128 with a locking feature configured to lock against a surface of the resection guide 12 after insertion. In some embodiments, the locking feature includes a bayonet tab 130 configured to be rotated into place and thereby prevent removal of the corner protector 122, 124 after insertion into the resection guide 12 (FIGS. 20E-20F). In some embodiments, the locking feature may further comprise a shoulder tab 132 which inhibit the peg from rotating by hooking over the shoulder of the saw guide. The shoulder tabs 132 thus help to align the grooves 125 with the slots 90, 88, 92 of the resection guide 12. FIGS. 21A-21C show additional embodiments of a corner protector. In FIG. 21A, the corner protector 122A includes a head 126A with grooves 125A and a shoulder tab 132A. In FIGS. 21B and 21C, the corner protector 122B additionally includes a locking feature in the form of a spring tab 134.

FIGS. 22A-22B illustrate an embodiment of cannulated corner protectors 136, 138. The cannulated corner protectors 136, 138 include a tubular opening 140, 142, respectively, to receive a pin. The cannulated corner protectors 136, 138 can be received in the receptacle 86 of the resection guide 12 (e.g., similar to the corner protectors 122, 124 and thereby provide corner protection and an adjacent connection point via the openings 140, 142, as shown in FIG. 22B. FIG. 22C illustrates another connector 144 having openings 146, 148 and configured to be inserted into the receptacle 86 of the resection guide 12 to place the openings 146, 148 for connection to pins and other components. For instance, the connector 144 can be inserted into a central portion 150 shown in an embodiment of the resection guide 12 shown in FIG. 22B.

Figure 23:
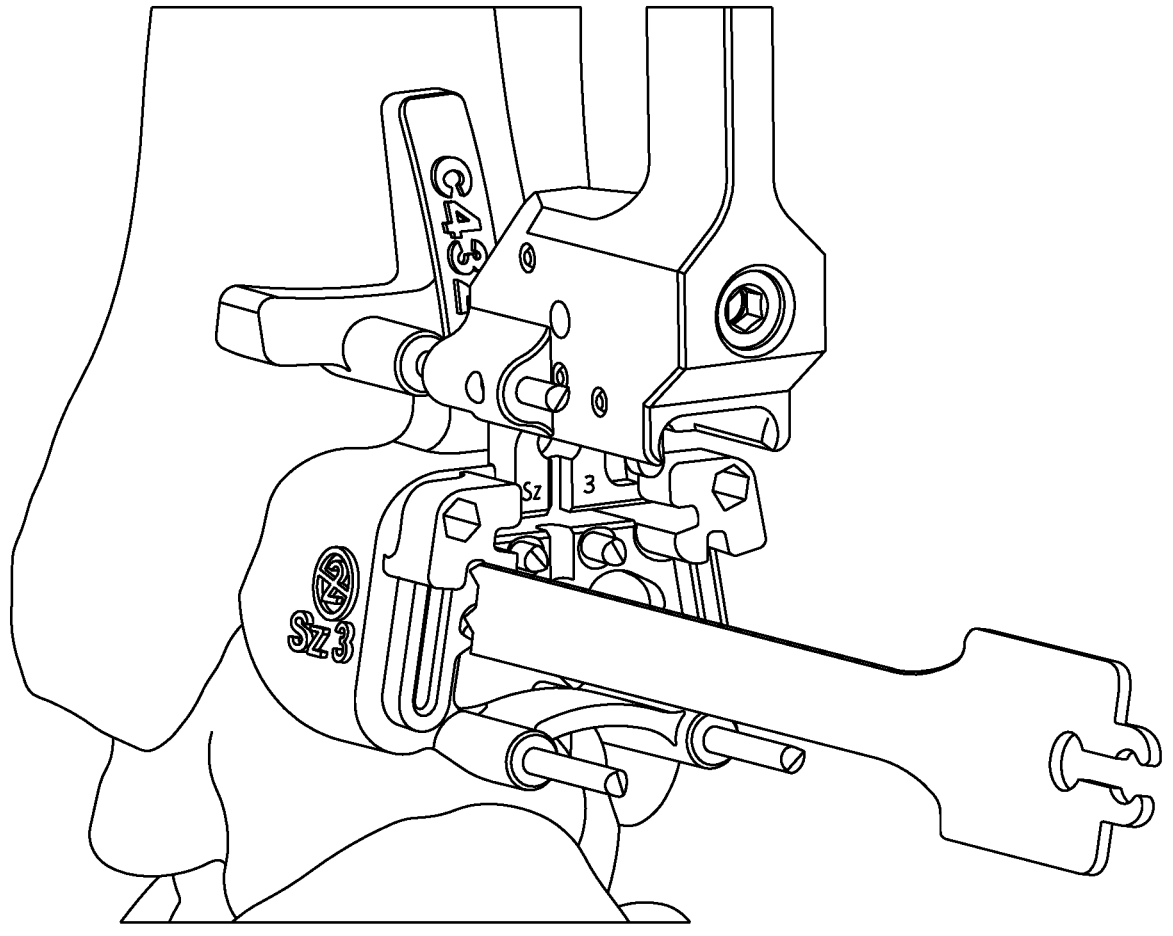
FIG. 23 depicts a perspective view of an embodiment of an embodiment of a medical device coupled to bone that includes a resection guide locator, a resection guide, an alignment reference component, and a modular resection guide with a cutting tool positioned proximate the medical device.
Figure 24A:
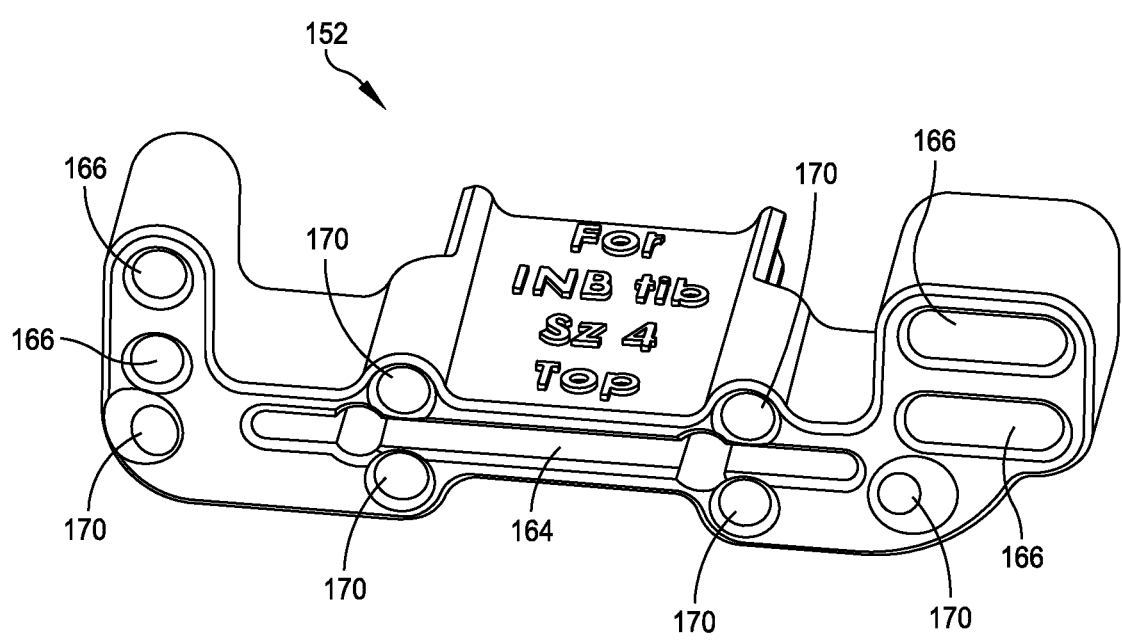
FIG. 24A depicts a top perspective view of an embodiment of a resection guide.
Figure 24B:
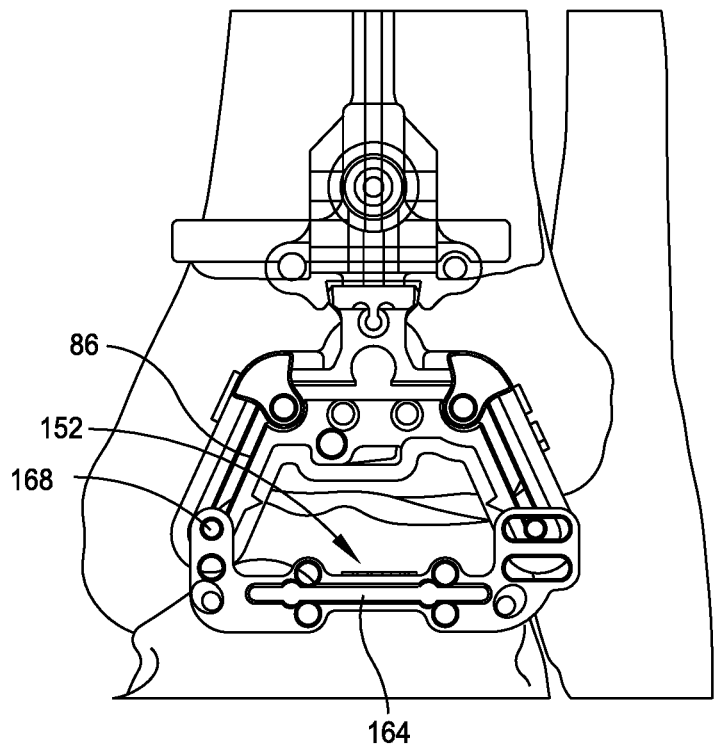
FIG. 24B depicts a side perspective view of an embodiment of a medical device coupled to bone that includes a resection guide locator, a resection guide, an alignment reference component and openings in the resection guide that allow access to bone.
Figure 25B:
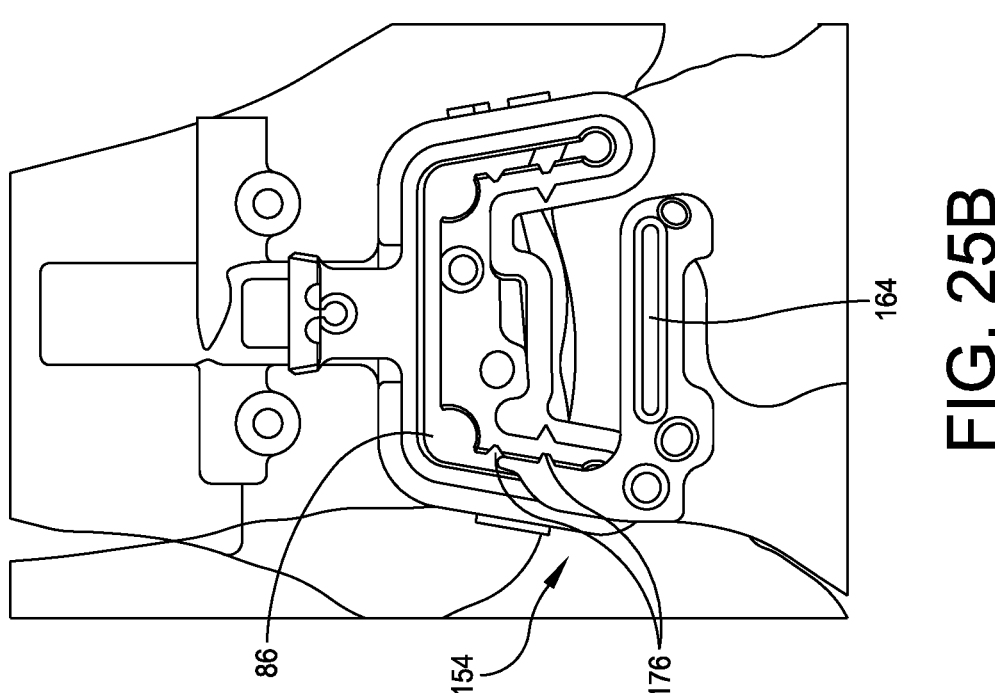
FIG. 25B depicts a front view of an embodiment of a medical device coupled to bone that includes a resection guide locator, a resection guide, and a modular resection guide.
Figure 25A:
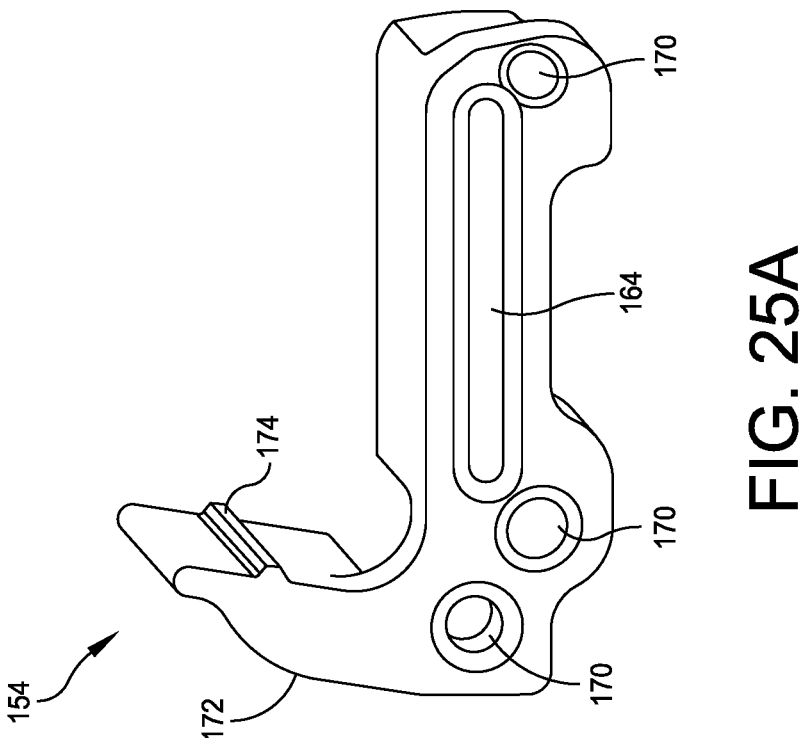
FIG. 25A depicts a perspective view of an embodiment of a modular resection guide.
Figure 26B:
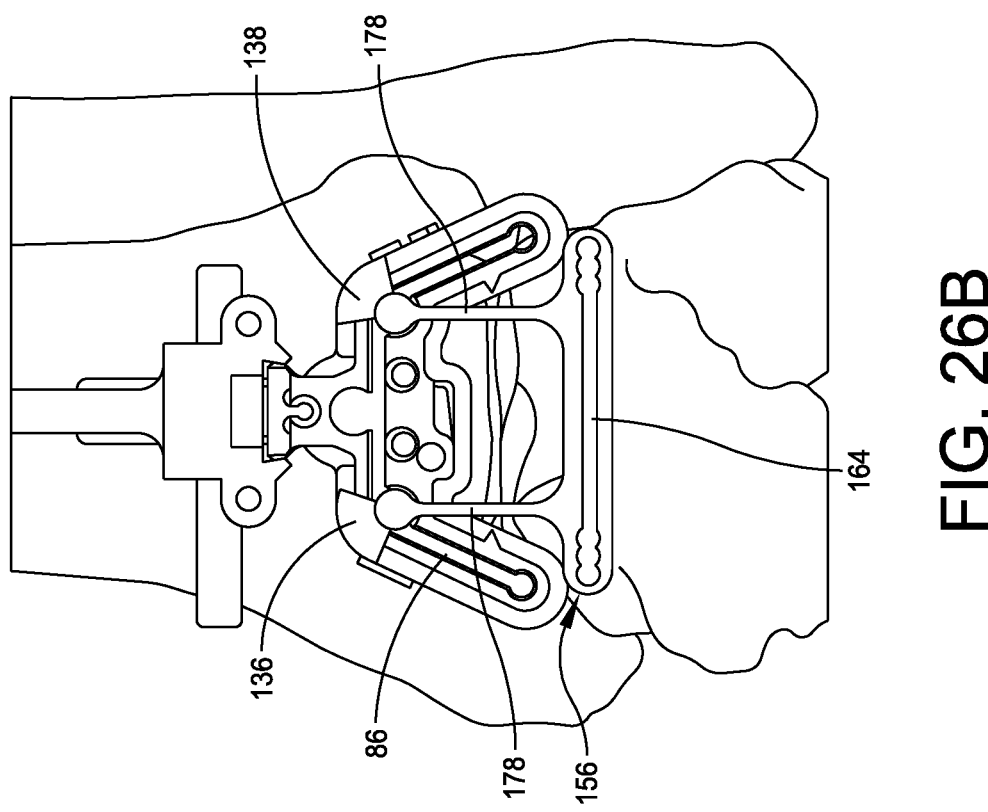
FIG. 26B depicts a front view of an embodiment of a medical device coupled to bone that includes a resection guide locator, a resection guide, an alignment reference component, and a modular resection guide.
Figure 26A:
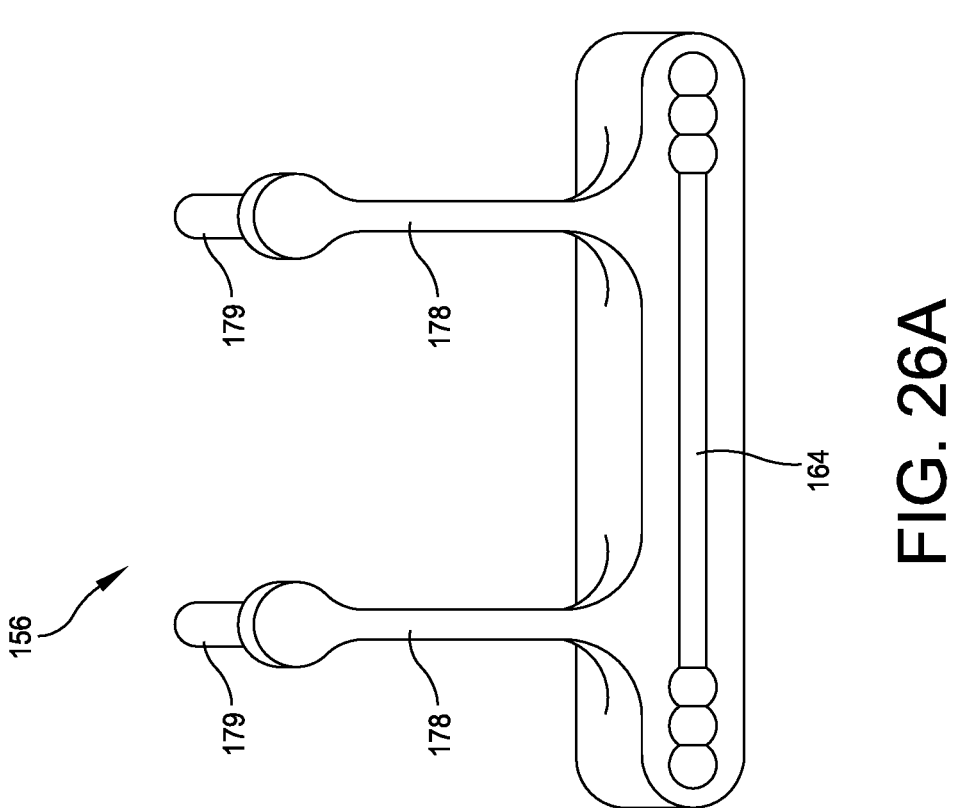
FIG. 26A depicts a perspective view of an embodiment of a modular resection guide.
Figure 27B:
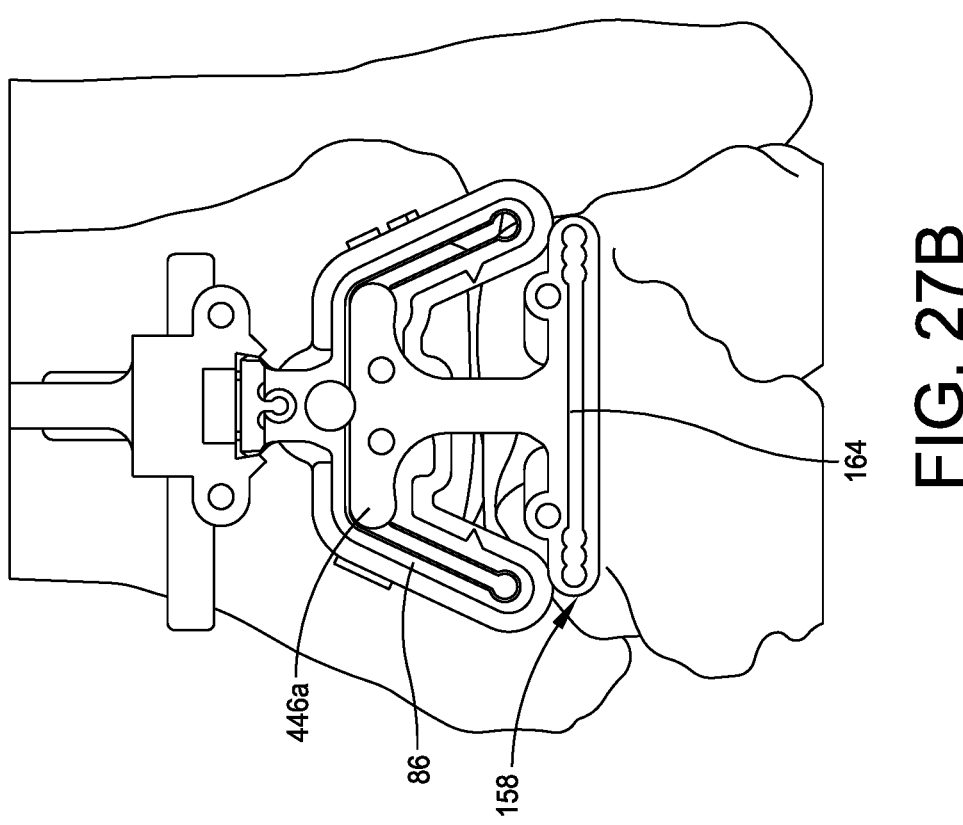
FIG. 27B depicts a front view of an embodiment of a medical device coupled to bone that includes a resection guide locator, a resection guide, an alignment reference component, and a modular resection guide.
Figure 27A:
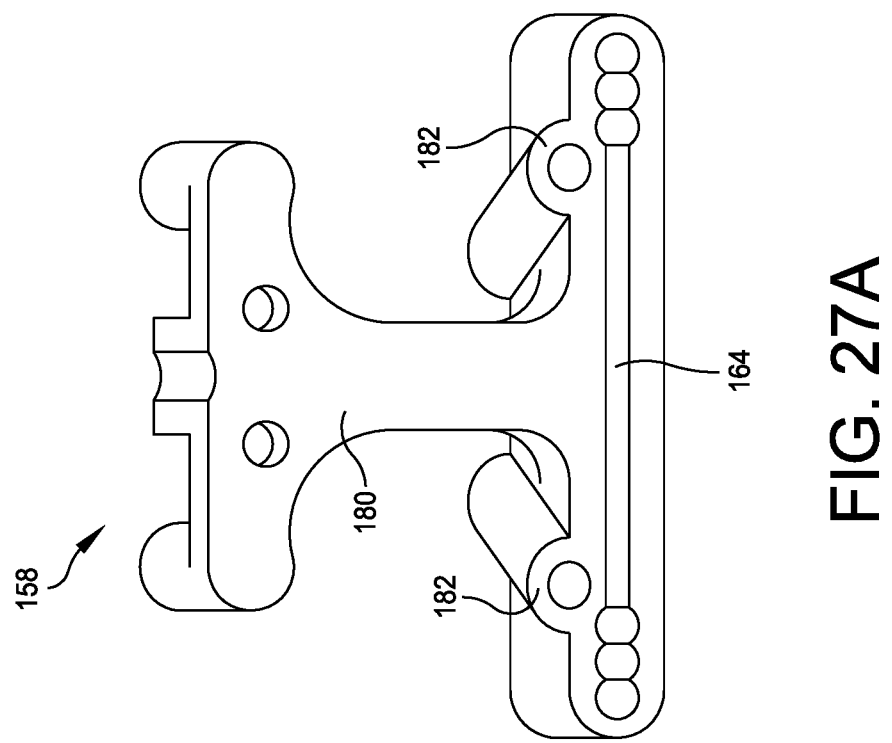
FIG. 27A depicts a perspective view of an embodiment of a modular resection guide.
Figure 28:
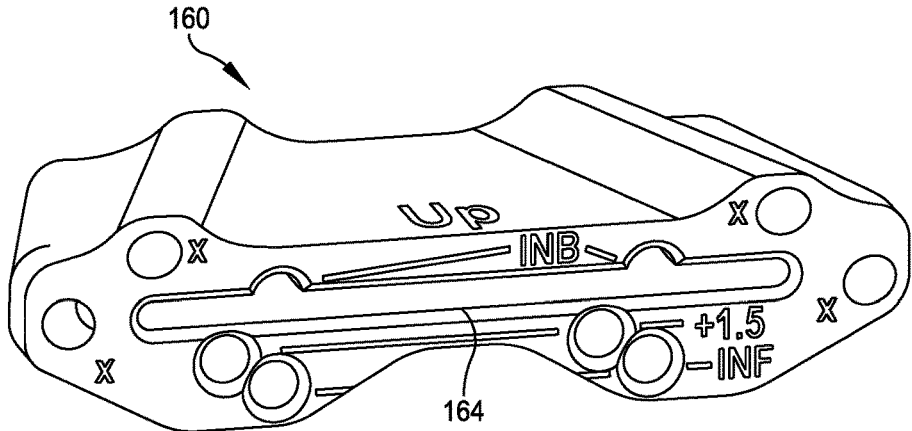
FIG. 28 depicts a perspective view of an embodiment of a modular resection guide.

As described herein, the resection guide 12 includes features for guiding resection cuts of the tibia, as further shown in FIG. 23. As also described herein, the resection guide locator 10 (and other disclosed embodiments) and/or the resection guide 12 (and other disclosed embodiments) include features for also enabling a talar resectioning cut to be made during a surgical procedure. For example, the system may further include a modular resection guide configured to be attached to the resection guide.

In one example, the resection guide 12, as described herein, is further configured to connect to one or more modular resection guides 152, 154, 156, 158, 160, 162 as shown in FIGS. 24A-24B, 25A-25B, 26A-26B, 27A-27B, 28, and 29A-29C, respectively. Each of the modular resection guides 152, 154, 156, 158, 160, 162 may include a resectioning slot 164 for performing a talar resection or other operation (e.g., the use of tools such as planar, non-planar, burr, saw, series of adjacent drilling holes to cut or sculpt the bone, etc.). The modular resection guides 152, 154, 156, 158, 160, 162 may include features for connecting and/or aligning with respect to the cutting guide 12 such that a talar resection may be made in a proper location with respect to tibial resection cuts.

It should be understood that while tibial and talar resectioning operations are described, more generally, the disclosed embodiments apply to performing an operation at a joint having a first bone and a second bone. According to some embodiments, a resection guide provides access to a first bone of the joint and the modular resection guide provides access to a second bone of the joint.

The modular resection guide 152 includes attachment apertures 166 for connecting to Kirchner wires or pins 168 placed in the receptacle 86 of the resection guide 12. The attachment apertures 166 may include multiple aperture rows and may be formed as slots to provide tolerance and different size options. The talar cutting guide 152 may additionally include apertures 170 for pinning the talar resection guide 152 in place relative to the talus.

The modular resection guide 154 comprises an extension 172 configured to be inserted into the receptacle 86 of the resection guide 12. The extension 172 may comprise a projection 174 configured to be inserted into a corresponding notch 176 in the receptacle 86 of the resection guide 12. The resection guide 12 may include a plurality of notches 176 for adjusting a positioning of the modular resection guide 154.

The modular resection guide 156 comprises a pair of connectors 178 including corresponding posts 179 for inserting into mating openings in the resection guide 12 or the openings 140, 142 of cannulated corner protectors 136, 138 inserted into the resection guide 12. The modular resection guide 158 similarly includes a connector 180 configured to be inserted into the resection guide 12. For example, the connector 180 may be configured to be inserted into the enlarged openings and the connector slot of the receptacle 86. The modular resection guide 158 may further include a pair of pin guides 182 configured to provide pinning locations for the talus.

The modular resection guides 160, 162 are examples of guides having a plurality of positions, depending on pinning locations (e.g., reversible guides). For example, the modular resection guides 160, 162 may be configured to be invertible such that a resection depth can be easily changed by repositioning the guide. This minimizes the size of the guide (e.g., by requiring fewer pin holes) and utilizes pinning locations that are configured for a thin cut talus where the pins have to be below the resection for stability or a deeper cut talus where the pins are above the cut.

Figure 29A:
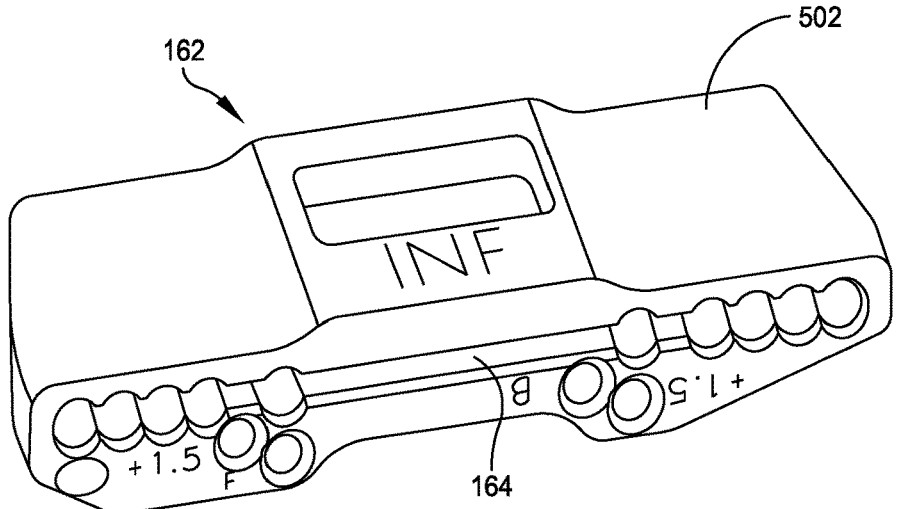
FIG. 29A depicts a perspective view of an embodiment of a modular resection guide.
Figure 29B:
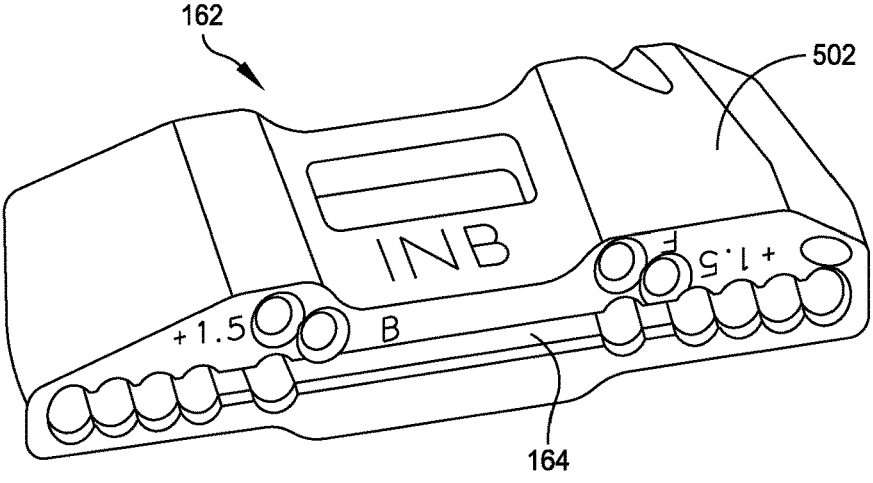
FIG. 29B depicts a perspective view of an embodiment of a modular resection guide.
Figure 29C:
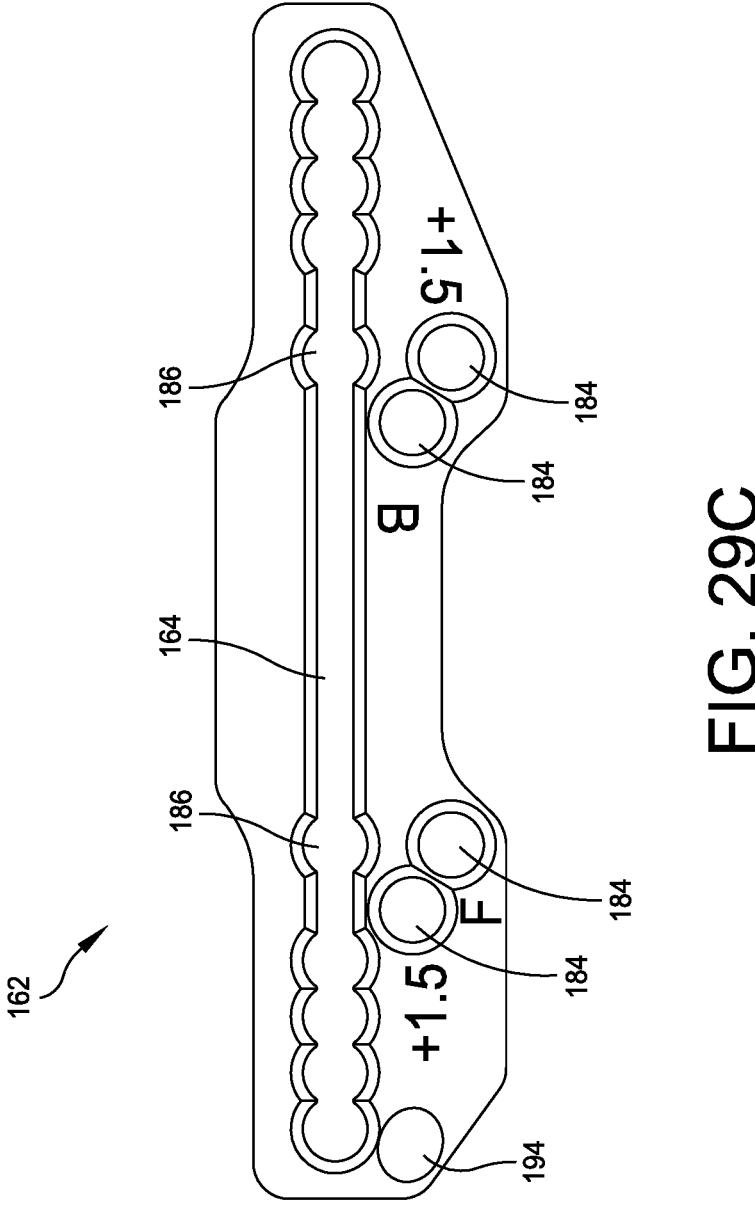
FIG. 29C depicts a perspective view of an embodiment of a modular resection guide.
Figures 40, 41:
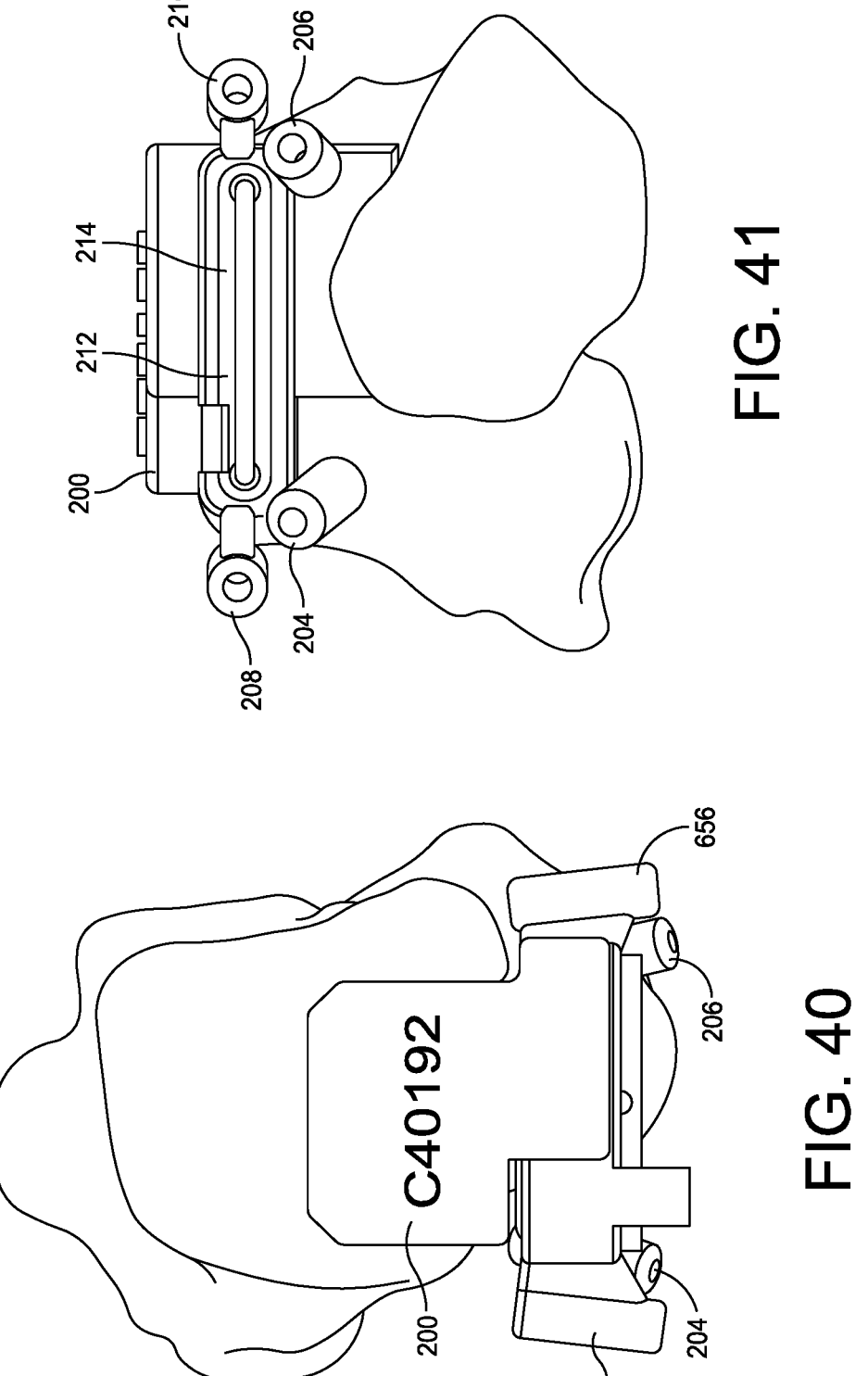
FIG. 40 depicts a top view an embodiment of a resection guide locator coupled to bone and through-bores providing access to bone through the resection guide locator.
FIG. 41 depicts a front view an embodiment of a resection guide locator coupled to bone and through-bores providing access to bone through the resection guide locator.
Figure 42:
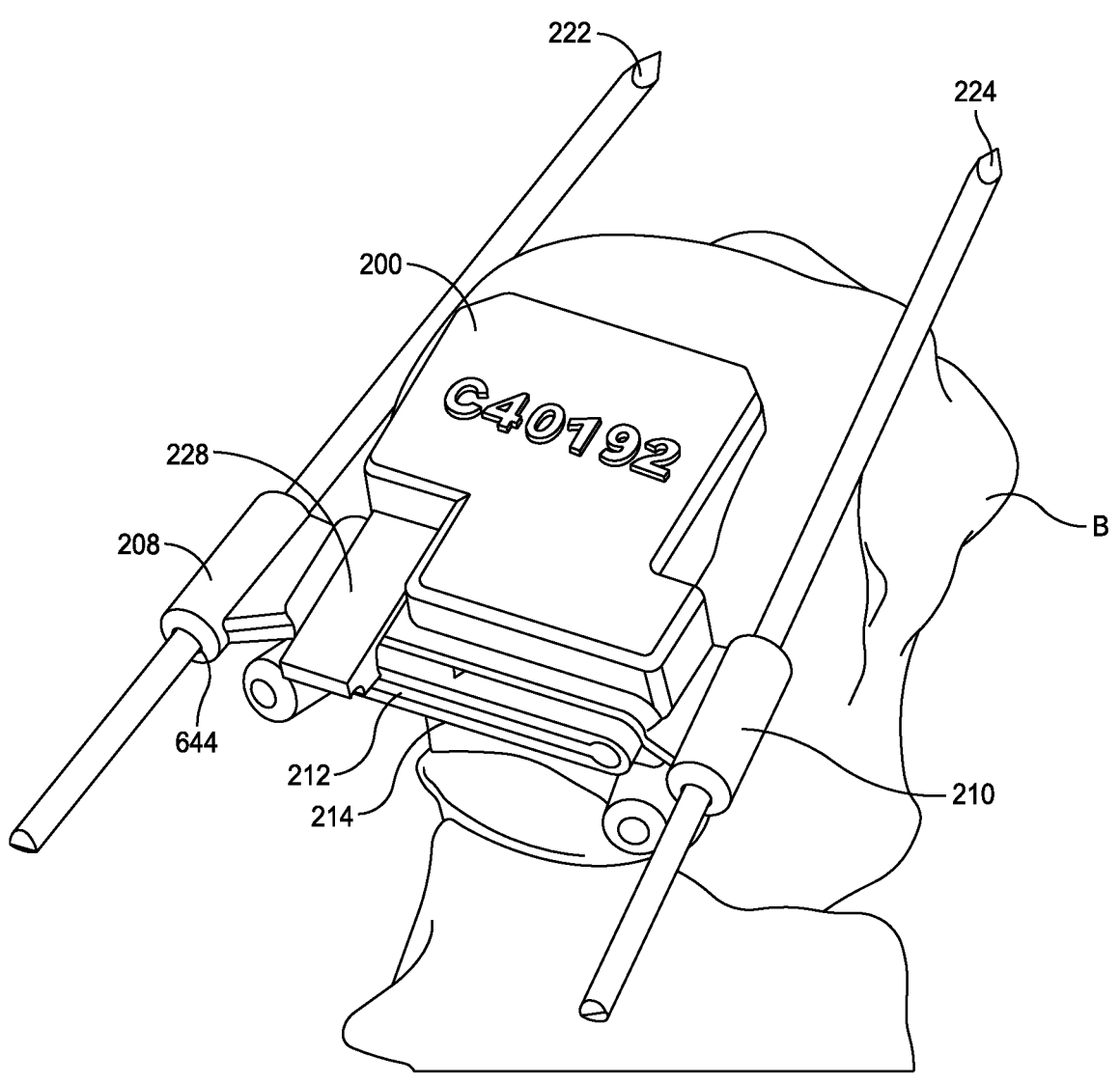
FIG. 42 depicts a top perspective view of an embodiment of a resection guide locator coupled to bone and through-bores in the resection guide locator having pins positioned therein.
Figures 43, 44:
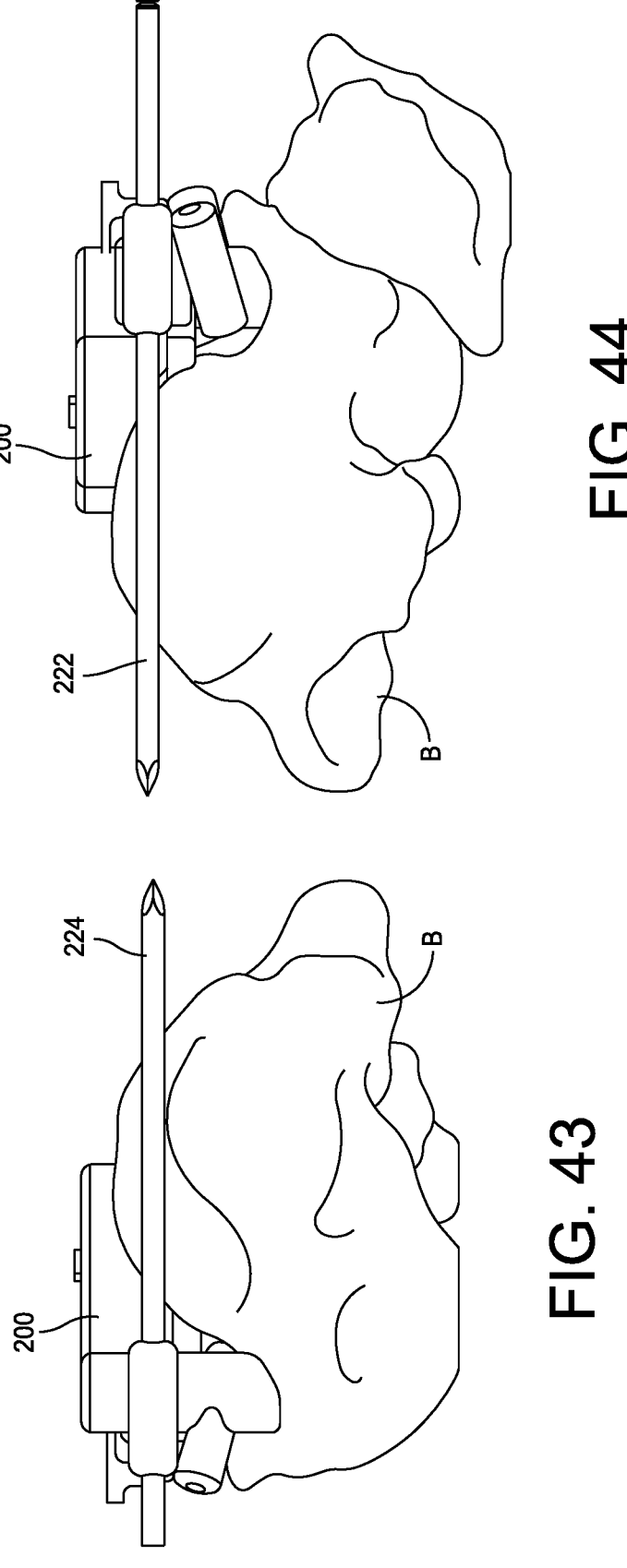
FIG. 43 depicts a side view of an embodiment of a resection guide locator coupled to bone and through-bores in the resection guide locator having pins positioned therein.
FIG. 44 depicts a side view of an embodiment of a resection guide locator coupled to bone and through-bores in the resection guide locator having pins positioned therein.
Figure 45:
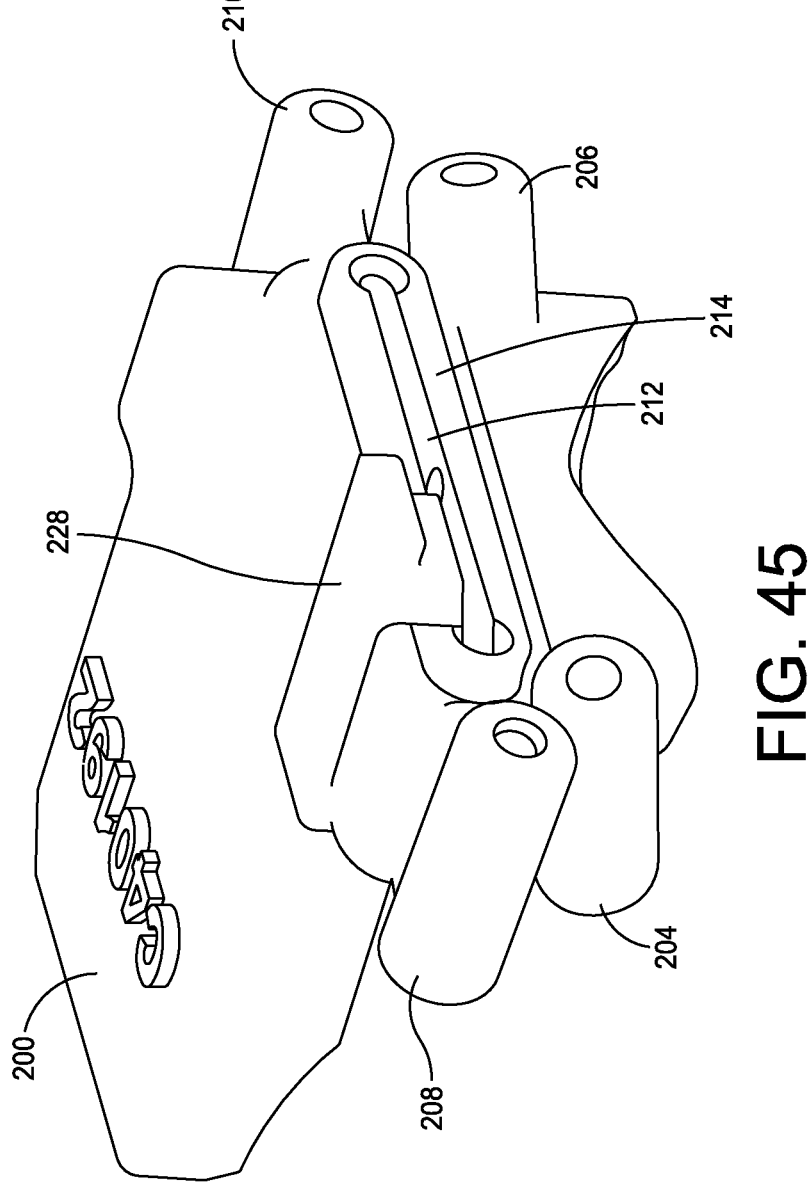
FIG. 45 depicts a side perspective view of an embodiment of a resection guide locator having through-bores.
Figure 46:
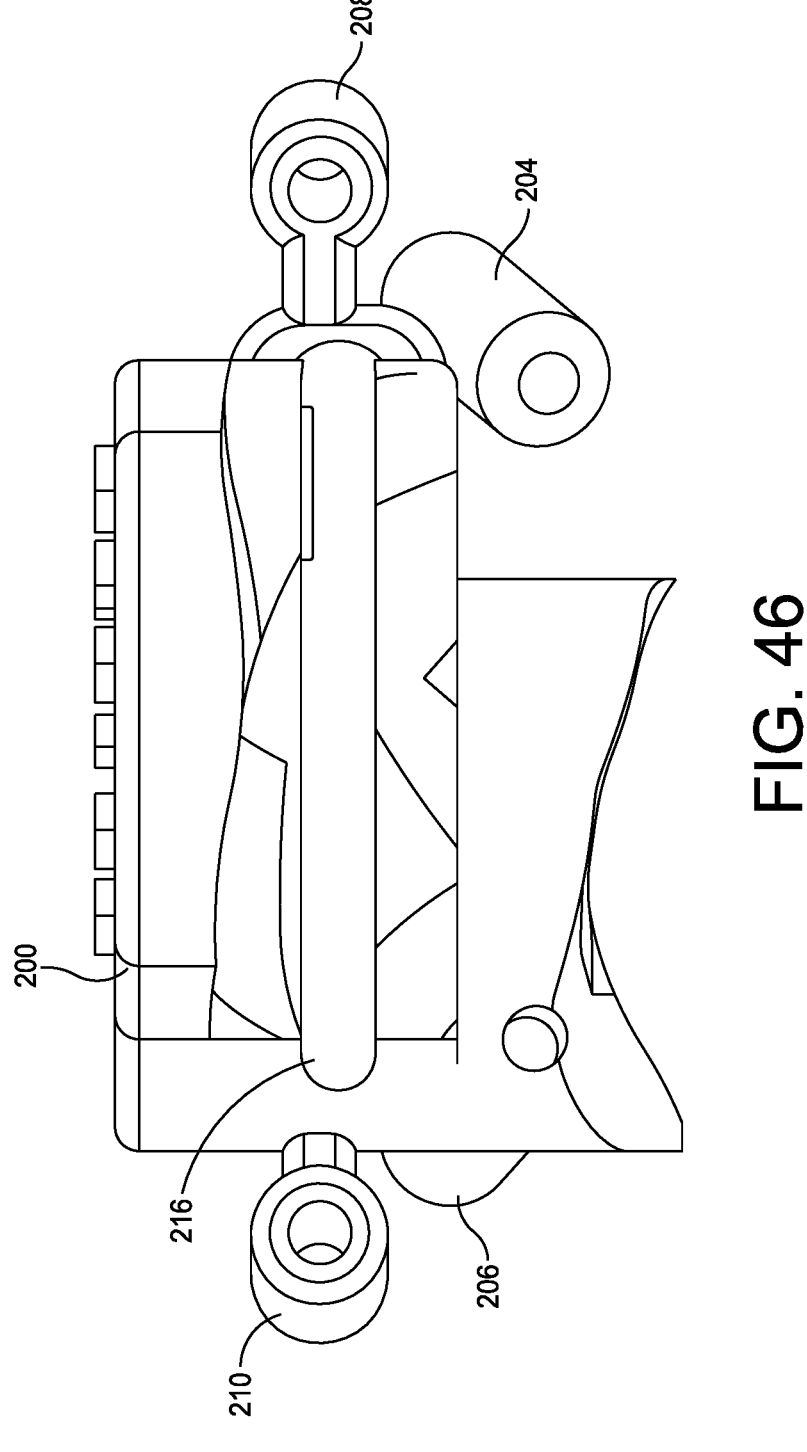
FIG. 46 depicts a front view of an embodiment of a resection guide locator having through-bores.

FIG. 29C includes a front view of the resection guide 162, showing a plurality of pin holes 184 in a first section of the resection guide 162 opposite the slot 164. The pin holes 184 may include multiple pairs of pin holes offset by a selected dimension. The slot 164 may include integral pin holes 186 that are spaced by a dimension equal to a spacing between respective pairs of pin holes 184.

FIGS. 30A-30D illustrate an exemplary process for positioning the resection guide 162 with respect to a joint. In one example, talar pins 188 have been previously inserted into the talus, such as through talar pin guides in one of the disclosed embodiments of the resection guide locator or resection guide. With other components removed, the resection guide 162 may then be placed onto the pins 188, such as by placing the pins in a selected pair of the pin holes 184. The slot 164 may then be in position for a talar resection cut. Additional pins 190 may be inserted into the slot 164 to provide end-stop points for the cut. An angled pin 192 may be placed through a corresponding angled pin hole 194 in the resection guide 162 to further secure the resection guide 162 in place.

FIGS. 31A-31D illustrate a first process flow of switching the modular resection guide 162 from a first position to a second position. In the first position, the slot 164 is positioned above pinning locations (FIG. 31A) and in the second position, the slot 164 is positioned below the pinning locations (FIG. 31D). The resection guide 162 may include a first section with the plurality of pin holes 184 and a second section with the slot 164. The slot 164 may include integral pin holes 186 providing additional pinning locations. The pin holes 186 may correspond to pinning locations for the pin holes 184 when inverting the resection guide 162. For example, in FIG. 31A, pins 188 are inserted into the pin holes 184. The resection guide is then removed and flipped such that the pins 188 extend through the pin holes 186. New pins 196 are thereafter inserted into the pin holes 184 and into the bone. The pins 188 in the pin holes 186 are removed and the slot 164 is ready and accessible for use in operation.

FIGS. 32A-32D are reversed to illustrate an opposite procedure for converting from the second position (FIG. 32A) to the first position (FIG. 32D). Talar pins 188 may be inserted into a first pair of the pin holes 184. The resection guide 162 may be removed and inverted, with the talar pins 188 being inserted into the other pair of the pin holes 184. New pins 190 may be inserted into the bone through the open pin holes 184 and the pins 188 may be removed. The resection guide 162 may then be removed and the pins 190 inserted into the pin holes 186 in the slot 164. Additional pinning may be inserted into the pin holes 184 to free the slot 164 and thus the resection guide 162 is returned to the first position (e.g., of FIG. 31A).

The embodiments of FIGS. 1-32 generally relate to a tibial resection guide locator for an ankle procedure, but it should be understood that the concepts can be applied to other resection guide locators, such as talar resection guide locators for other parts of the ankle procedure and/or femoral resection guide locators for knee procedures. FIGS. 33-48 illustrate an embodiment of a resection guide locator 200, according to some disclosed embodiments. The resection guide locator 200 can be, for example, a talar resection guide locator for an ankle procedure.

The resection guide locator 200 can be formed from a resilient polymer material of the type that is suitable for use in connection with stereo lithography, selective laser sintering, or the like manufacturing equipment, e.g., a polyamide powder repaid prototype material is suitable for use in connection with selective laser sintering. Resection guide locator 200 can also include a conformal bone engaging surface that is complementary to the contours of a corresponding portion of the patient's upper talus. Through the previously discussed imaging operations, the conformal bone engaging surface of resection guide locator 200 can configured for complementary matching with anatomical surface features of a selected region of the patient's natural bone (e.g., upper surfaces of the patient's talus).

Resection guide locator 200 can include a unitary block structure that defines a central guide receptacle 202 and a plurality of through-bores 204, 206, 208, 210. The guide receptacle 202 can be formed as an elongated slot that is sized and shaped to allow a typical surgical saw, of the type often used for bone resection, to pass through from a correspondingly positioned and sized slot 212 in a talar resection guide 214. An annular wall 216, having a shape that is complementary to the outer profile of talar resection guide 214 defines a shape of the guide receptacle 202.

The resection guide locator 200 can include features for enabling secure mounting of the resection guide locator 200 to patient bones, including the through bores 204, 206, 208, and 210. In an exemplary embodiment, the through-bores 204, 206 are arranged adjacent to the guide receptacle 202 and are configured to receive pins 218, 220 that are inserted into the bone B of the patient. The through-bores 208, 210 are arranged adjacent to the guide receptacle 202 and are largely in-plane with the resection slot and are directed to provide a path for pins 222, 224 that are inserted into the space adjacent to bone B. In an ankle these spaces adjacent to the talus (bone B) and the fibula and the medial malleolus of the tibia are referred to as the ankle gutters. Pins 222, 224 placed here into the gutters in-plane with the talus resection prevent the excursion of the saw into surrounding anatomical structures that are not intended to be resected (the tibia, fibula and soft-tissues). In manufacturing the resection guide locator 200 to be a patient-specific tool, the through-bores 208, 210 can be configured with an alignment that matches a path to a location of the gutters of the patient's bone, thereby providing assurance that the stationary through-bores 208, 210 will be positioned to direct the pins 222, 224 to the gutters.

Figures 47, 48:
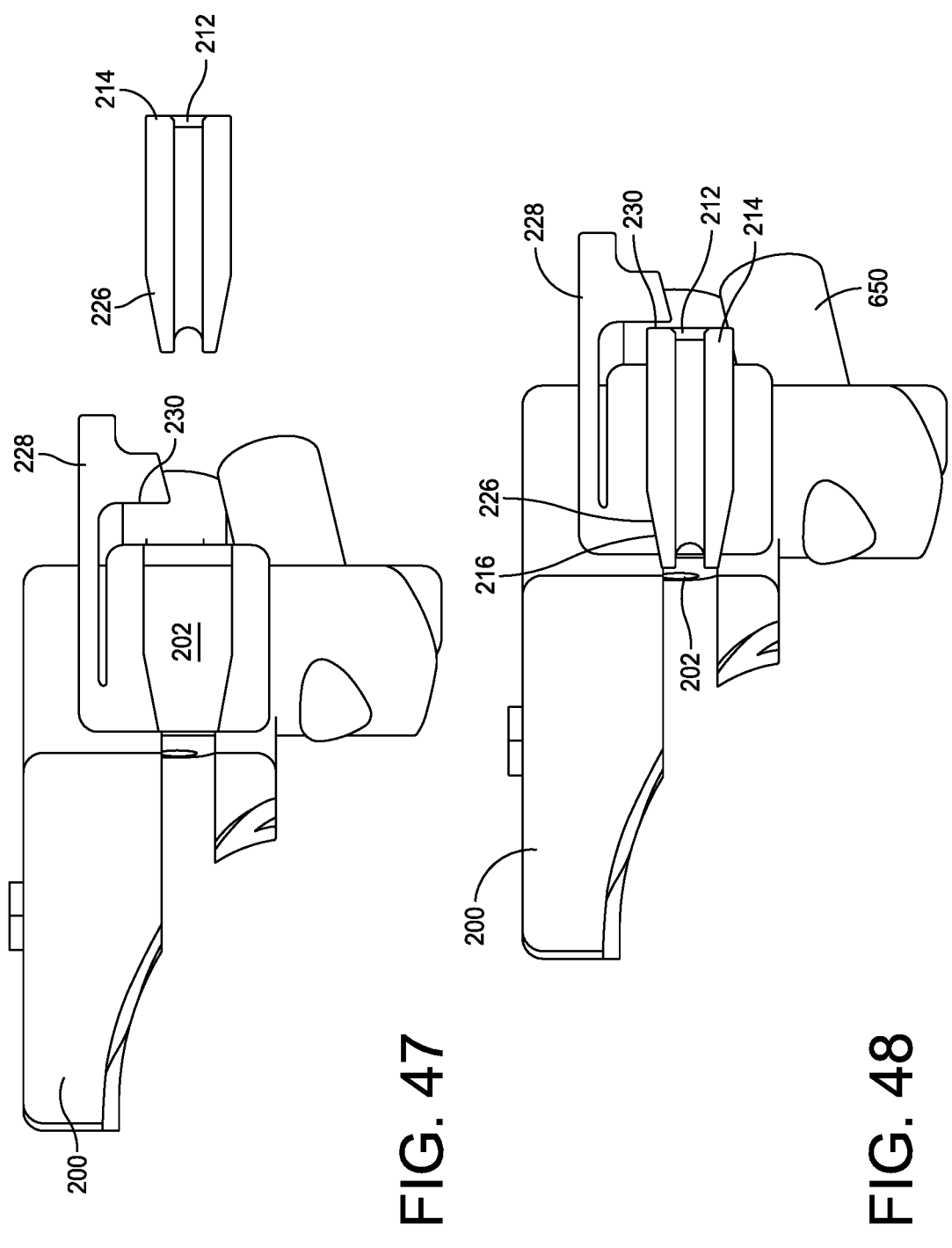
FIG. 47 depicts a side cross-sectional view of an embodiment of a device having a resection guide locator and a talar resection guide.
FIG. 48 depicts a side cross-sectional view of an embodiment of a device having a resection guide locator and a talar resection guide coupled to the resection guide locators.

The resection guide locator 200 and resection guide 214 can include additional features for providing a secure attachment between the modular components. For example, as shown in FIGS. 47 and 48, the annular wall 216 and a proximal portion 226 of the guide 214 can include tapered surfaces to help guide the resection guide 214 into the guide receptacle 202. Further, the resection guide locator 200 can include a built-in spring clip 228 including a retaining surface 230 that is biased into a position to inhibit removal of the resection guide 214 (FIG. 48).

Figure 49:
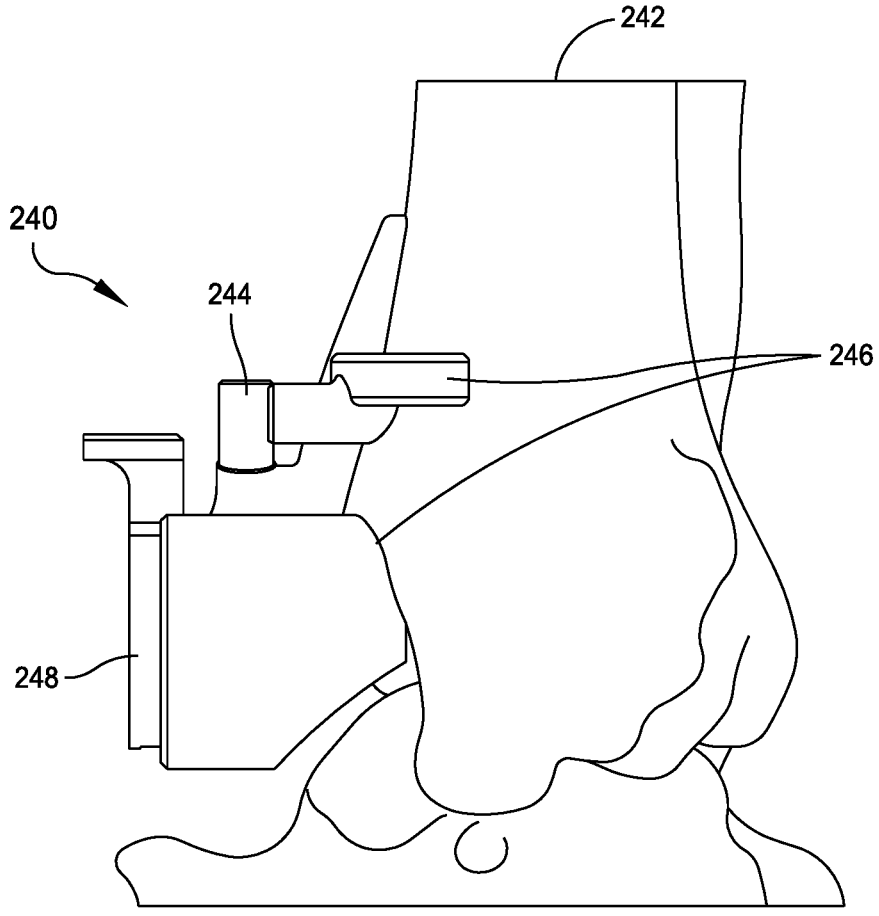
FIG. 49 depicts a side view of an embodiment of a device having a resection guide locator and a resection guide coupled to bone.

FIG. 49 depicts a side view of medical device 240 coupled to bone 242 that includes a resection guide locator 244 shaped to conform to sections of bone 246 to which it is coupled during use and a resection guide 248 positioned therein. In particular, resection guide locator 240 as shown is a tibial resection guide locator. Devices such as resection guides and/or resection guide locators may be formed from polymer materials, for example, resilient polymer materials. Polymer materials for use in devices such as resection guides and/or resection guide locators may be selected based on desired properties of the polymer materials and/or suitability for use in manufacturing methods such as molding, 3D printing, for example, stereolithography, selective laser sintering, or the like.

Figure 50:
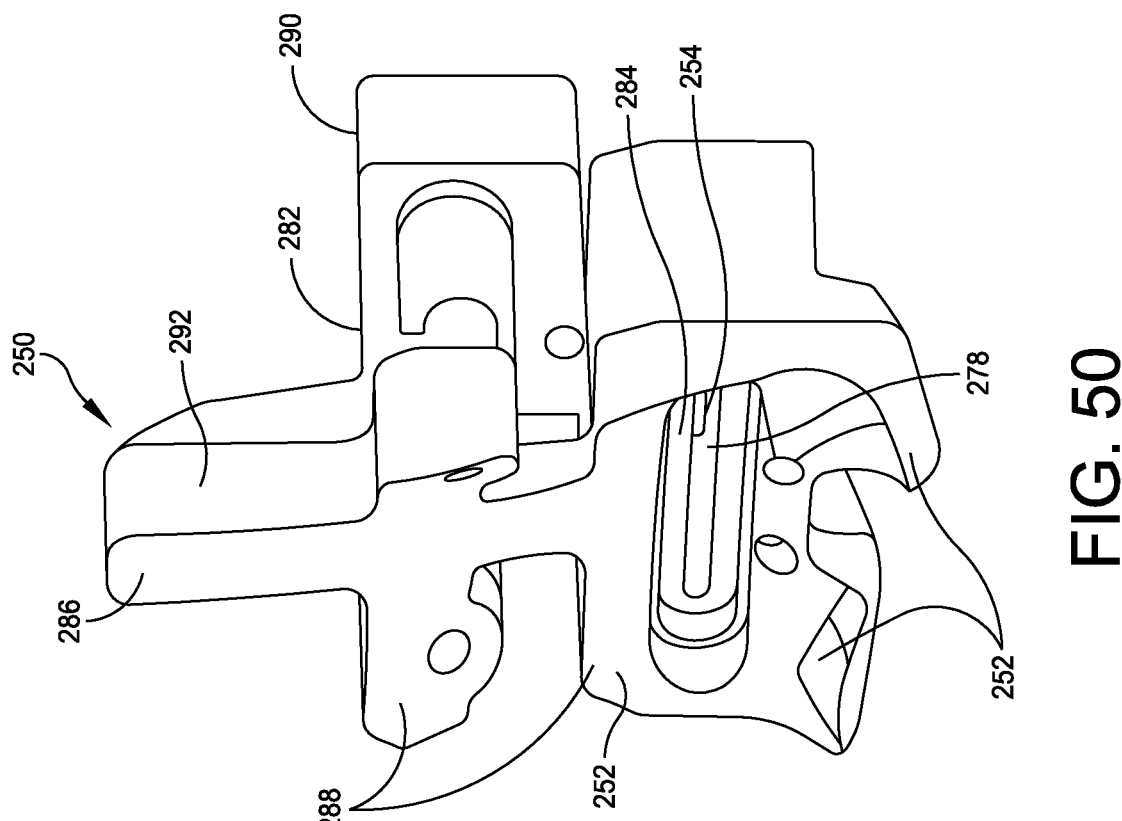
FIG. 50 depicts a perspective view showing the bone engaging side of an embodiment of a device for use as a resection guide.

In some embodiments, multiple materials may be used in different sections to form a device having a patient-specific surface. As shown in FIG. 50, resection guide 250 may be a block structure with bone engaging features 252 configured to match anatomical surface features of a selected region of the patient's natural bone (e.g., a portion of the tibia). Resection guide 250 includes cutting guide 254 for guiding an instrument including, but not limited to a saw, drill, or tool known in the art during a surgical procedure. In some instances, resection guide 250 may include features that allow additional components to be connected to the resection guide, as will be further described.

Figure 51:
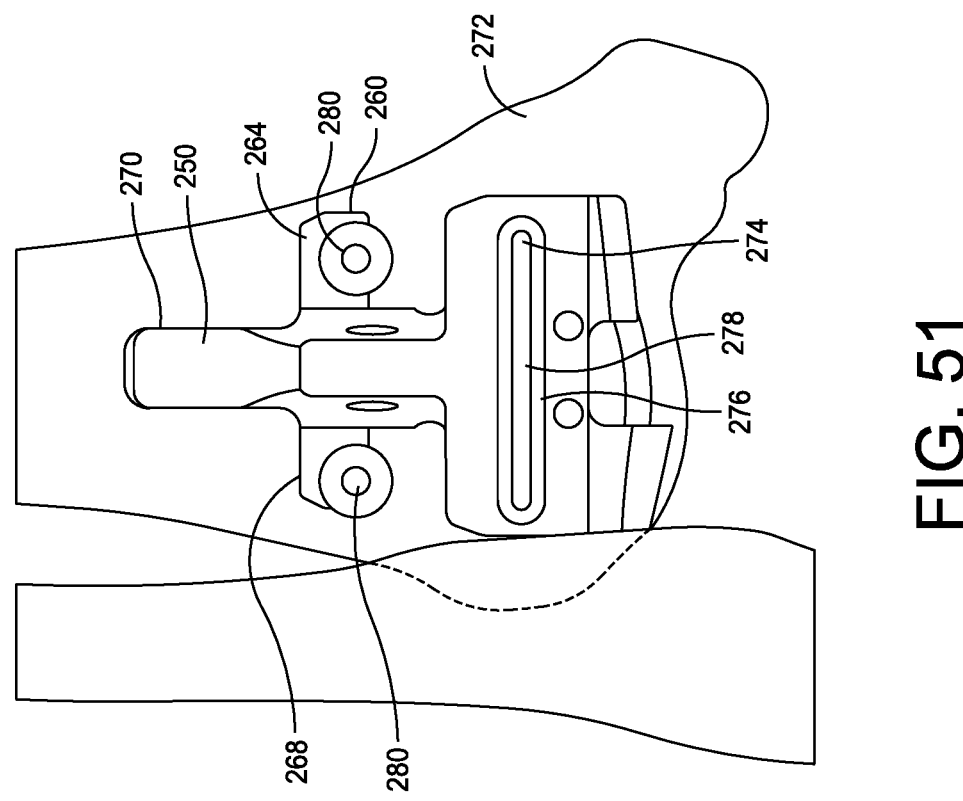
FIG. 51 depicts a front view of an embodiment of a resection guide coupled to bone.

In some embodiments, resection guide 250 may include a cruciform tibial yoke 264. Cruciform tibial yoke 264 can include a pair of spaced apart arms 266, 268 that project outwardly from a central post 270. Sections of the device such as the arms and central post may each include one or more patient-specific surfaces, for example, a conforming bone-engaging surface that is complementary to the contours of a target area of the patient's bone. The bone-engaging surfaces may match anatomical surface features of a target area of the patient's natural bone using patient-specific data derived from images of the patient. For example, as shown in FIG. 51, a patient-engaging surface 252 (similar to patient-engaging surfaces 246 shown in FIG. 50) may be complementary to the contours of a patient's lower tibia 272 to allow for coupling to the tibia as shown.

Resection guide 250 may include features that enable instruments to access the patient's tissue, such as bone. For example, instruments (e.g., capable of cutting) may access tissue, such as bone, through opening 274. In order to reduce and/or inhibit damage to the resection guide and thus debris formation during use, the openings may be lined with composite materials, ceramics, plastics, and/or metals. For example, openings may be lined with metal liners. It may be desired to select a material for the linings based on the requirements during use. For example, it may be desirable to use a material having a particular hardness such as a hardness greater than about 80 Brinell. As shown in FIGS. 50-51, openings include liners such as sleeves 276. Configurations of openings may vary depending on the needs and/or step required for a specific surgical procedure. For example, in FIGS. 50-51 openings are shaped as slot 278 and includes sleeve 276. As shown in FIG. 51, slot may be used to access bone to enable cutting of the bone. Openings may have any geometry to allow instruments of varying geometries to access bone. Apertures 280 in devices may also be present to engage a bone surface and/or another component.

As shown in FIG. 50 device 250 includes injection molded portion 282 having metal component 284 positioned within it. This may be accomplished using injection molding techniques known in the art such as insert molding and/or over molding. Patient-specific engaging section 252 includes patient-specific surface 286 having patient-specific contours 288 on one side and an instrument-engaging surface 290 on an opposite side. Portions of the patient-specific engaging section may be molded and/or formed using 3D printing methods. For example, a patient-specific section may be 3D printed using selective laser sintering (SLS) to create the patient specific contours. Using 3D printing may allow for customization of the patient-specific engaging section, for example, by including patient-specific indicators on surface of a patient-specific surface. Indicator 292 is shown on patient-specific section 252.

Figure 52:
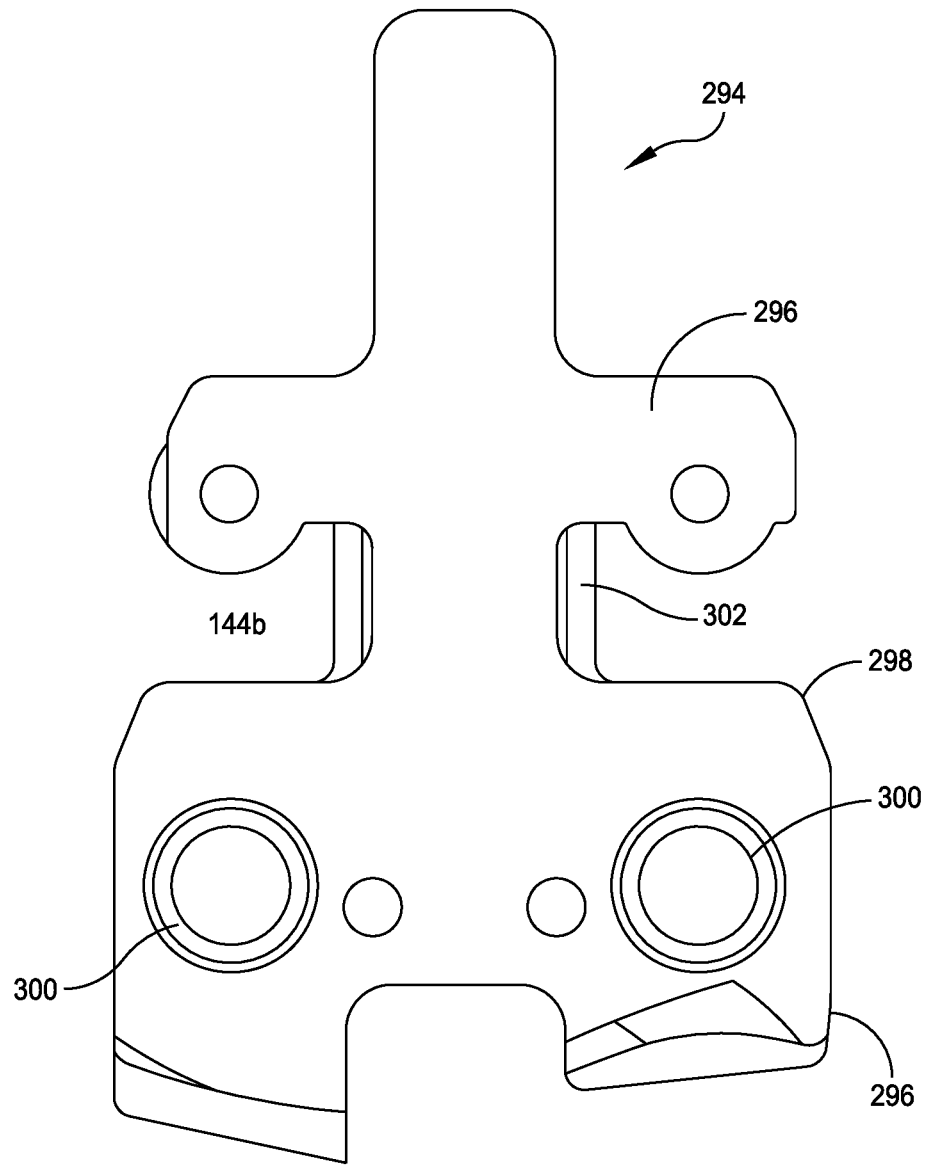
FIG. 52 depicts a back view of an embodiment of a device for use in orthopedic surgery having a patient-specific surface, a standard section and inserts.

An example of a device, such as resection device 294 having patient-specific surfaces 296 on patient-specific section 298 is shown in FIG. 52. As can be seen patient-specific surface 296 of body section 298 may be shaped to conform to one or surfaces of bone of a patient. Sleeves 300 extend through patient-specific section 298 and instrument-engaging section 302 to allow access to the bone through resection device 294. As shown resection guide 294 includes two body sections 298, 302 and sleeves 300 that extend through both body sections.

In some instances, body sections 298, 302 may be injection molded and/or 3D printed to form a unitary device or may be subsequently coupled after manufacturing to form the device. Materials for the body sections may include radiolucent materials. Body sections may include composites, thermoplastics including, but not limited to polycarbonate (PC), polyethylene (PE), methyl methacrylate (MMA), polymethyl methacrylate (PMMA), polyether ether ketone (PEEK), poly ether ketone ketone (PEKK), acrylonitrile butadiene styrene (ABS), polylactic acid (PLA), polyamide, such as nylon, other plastics known in the art, and combinations thereof. In particular, materials may be selected that are capable of being used in additive manufacturing such as 3D printing, selective laser sintering (SLS), and/or injection molding, for example polyamides such as nylon or ceramics. In some embodiments, materials used in a device may be selected for specific properties desired in a particular device or location in the device such as magnetism, surface roughness, reflectivity, refractivity, radiolucency, radiopacity, strength, compatibility with in vivo placement, etc.

Devices described herein may include indicators such as labels on one or more surfaces (e.g., patient specific labels and/or use labels, reference points, measuring members, provided on surfaces of devices and/or elements thereof) and/or embedded therein. These indicators on elements of a device may be used to identify parts during manufacturing and/or surgery. For example, during use in a surgical method an implant may be positioned (e.g., implanted) in a patient. Patient specific devices, implants, and/or instruments may include indicators to communicate information during use, for example, to communicate information to a surgical team. In some instances, patients may be assigned a patient indicator which may be used to mark elements of a device and/or instruments. This may allow users such as members of a surgical team to confirm that the device and/or instrument is being used for the right patient. Thus, after an image of a target surface of the patient is made a device having a patient specific surface may be formed and the corresponding patient specific indicator is placed on a surface. Thus, during surgery the identity of a patient, the predetermined location of an element of the device or instrument, or other identifying markings may be used to confirm the identity of the patient or other patient or procedure specific information.

Figure 53:
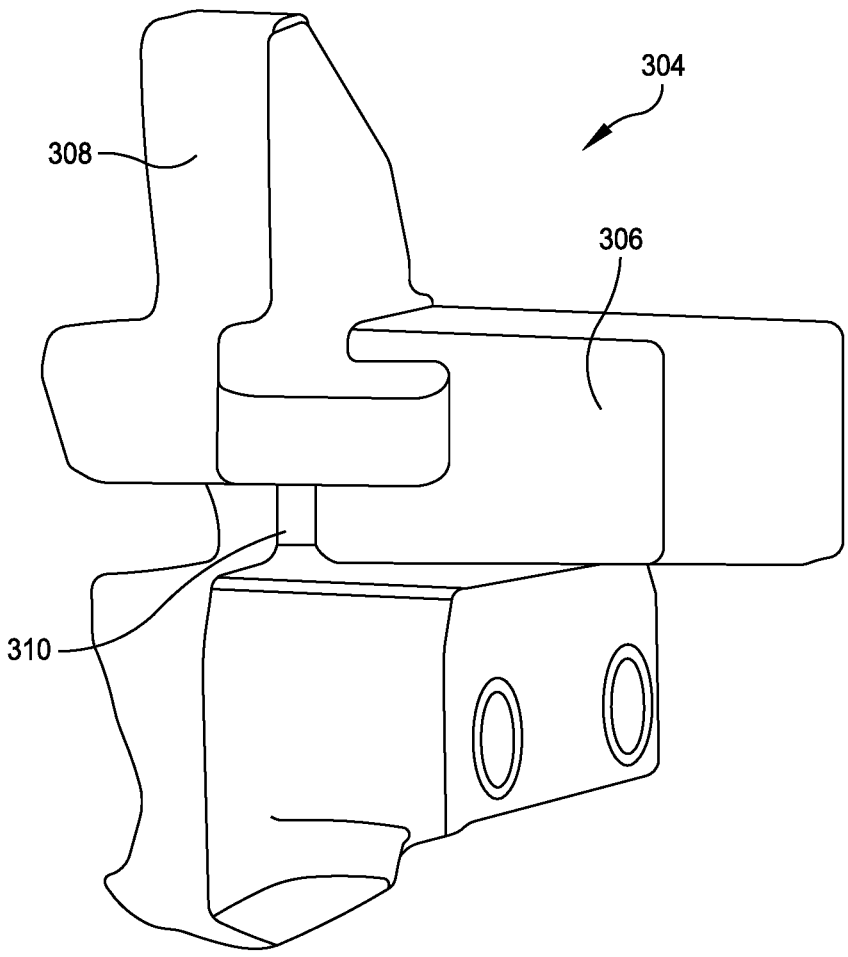
FIG. 53 depicts a side perspective view of an embodiment of a device for use in orthopedic surgery having a patient-specific surface, a standard section and inserts.

FIG. 53 depicts device 304 that includes indicators 306, 308. Indicator 308 may include identifiers that are patient specific. Patient specific indicators may allow a team prepping and/or performing surgery to confirm that the device is the correct one. Further, FIG. 53 depicts positioning element 310. Positioning elements may be formed from materials, such as radiopaque materials, for example metals such as medical grade stainless steel and/or titanium that can be seen on imaging such as x-rays.

Figure 54:
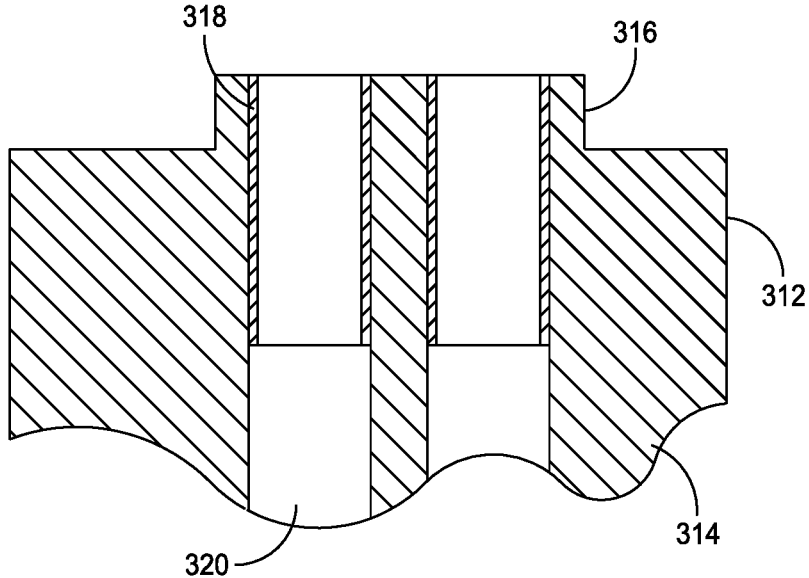
FIG. 54 depicts a cross-sectional view of an embodiment of a device for use in orthopedic surgery having a patient-specific surface, a device engaging surface, and inserts positioned therein.

FIG. 54 shows a cross-sectional side view of device 312 having patient-specific surface 314, instrument engaging surface 316, and sleeves 318. Openings 320 proximate the patient-specific surface 314 may have a larger diameter than sleeves 318 to ensure clearance of instruments during use. This may inhibit and/or prevent generation of debris during use.

Figure 55:
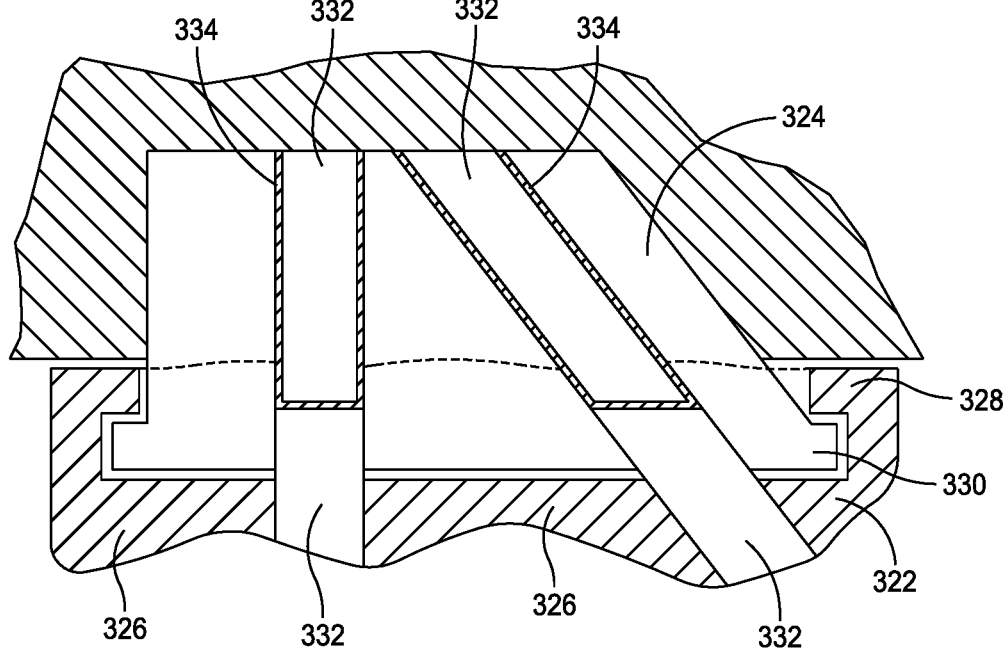
FIG. 55 depicts a cross-sectional top view of an embodiment of a device for use in orthopedic surgery having a patient-specific surface, a standard section and inserts.
Figure 56:
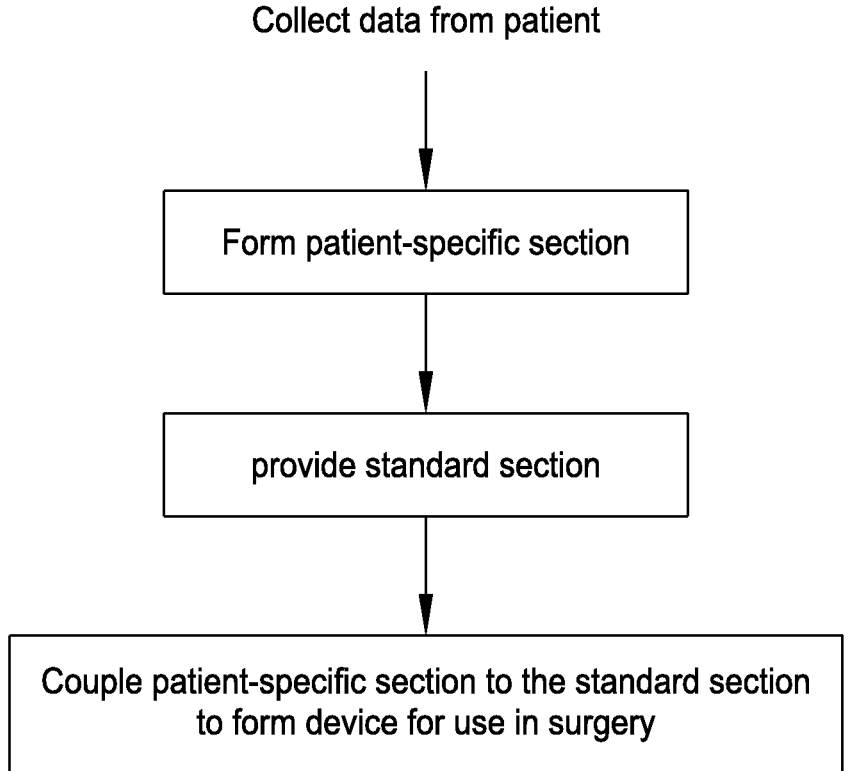
FIG. 56 depicts a flow-chart depicting steps involved in forming a device for use in orthopedic surgery having a patient-specific surface.

Devices may include multiple body sections, liners, connectors, and/or inserts. For example, FIG. 55 patient-specific section 326 having a patient-specific surface 322 and standard section 324. Standard section 324 may be configured to engage one or more instruments. As shown in FIG. 55 patient-specific section 326 may be configured to couple with standard section 324. In many instances, patient specific section 326 and standard section 324 are formed separately and coupled together prior to use as outlined in FIG. 56.

Sections of a device may be coupled together using any method known in the art including, but not limited to friction fits such as joints, for example, dado joints, tongue and groove joints, rabbit joints, mortise and tenon joints, box joints, biscuit joints, dovetail joints, etc., fasteners such as screws, staples, pins (e.g., cross-hair pins), plates, adhesives such as glue, and/or combinations thereof. For example, as shown in FIG. 55 patient-specific section 326 is coupled to standard section 324 using joint elements 328, 330.

Openings 332 may extend through both standard section 324 and patient-specific section 326. Sleeves 334 may be positioned in at least a section of openings 332. As shown in FIG. 55, sleeves 334 are positioned in section of openings 332 corresponding to standard section 324.

Devices may be constructed such that during use devices may perform multiple functions including, for example, alignment and/or resection. In particular, an alignment section may be combined with a resection guide.

Figure 57:
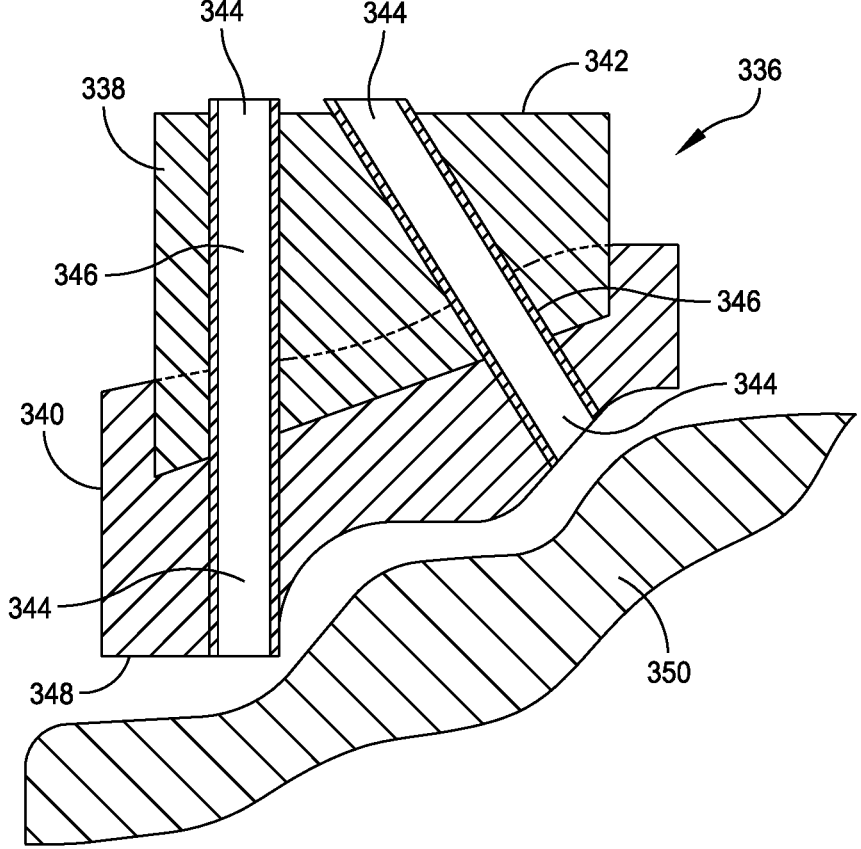
FIG. 57 depicts a cross-sectional side view of an embodiment of a device for use in orthopedic surgery having a patient-specific surface, a standard section and inserts.

Device 336 as depicted in FIG. 57 includes multiple sections 338, 340 where instrument-engaging section 342 is coupled to patient-specific section 340. Patient-specific section may be 3D printed or molded (e.g., overmolded) onto a standard section, such as an tool-engaging section and/or instrument-engaging section. In some instances, openings may extend through both standard section and patient-specific section. As shown in FIG. 57, openings 344 extend through both standard section 338 and patient-specific section 340 and are lined with metal inserts 346. Metal inserts 346 extend from an instrument-engaging surface through to bone engaging surface 348. Bone engaging surface 349 is formed to conform with a target location on bone 350 on a patient.

Figure 58:
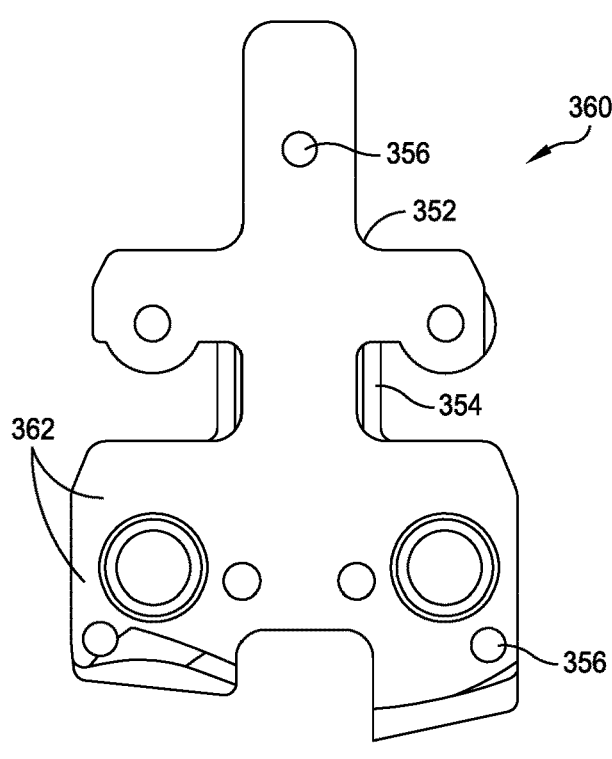
FIG. 58 depicts a back view of an embodiment of a device for use in orthopedic surgery having a patient-specific surface, a standard section and inserts.
Figure 59:
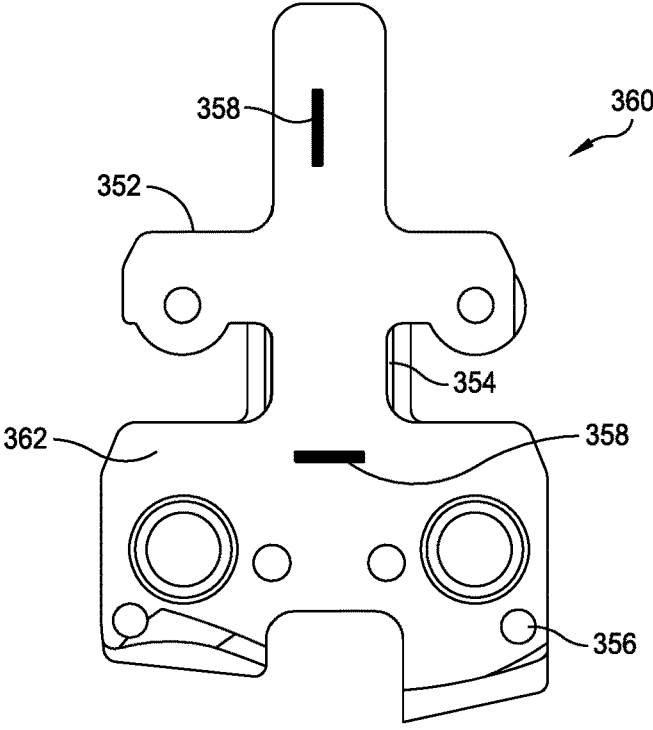
FIG. 59 depicts a back view of an embodiment of a device for use in orthopedic surgery having a patient-specific surface, a standard section and inserts.

FIGS. 58-59 depict embodiments of devices having differing configurations. Sections 352, 354 are coupled together using a friction fit using pins 356 (FIG. 58) or staples 358 (FIG. 59). In some instances, pins and/or staples may be made from radiolucent materials so that the pins and/or staples may be used as position elements during imaging. Further, FIGS. 58-59 show devices 360 having surfaces corresponding to a patient's bone region of interest as patient-specific surface 362.

Figure 60:
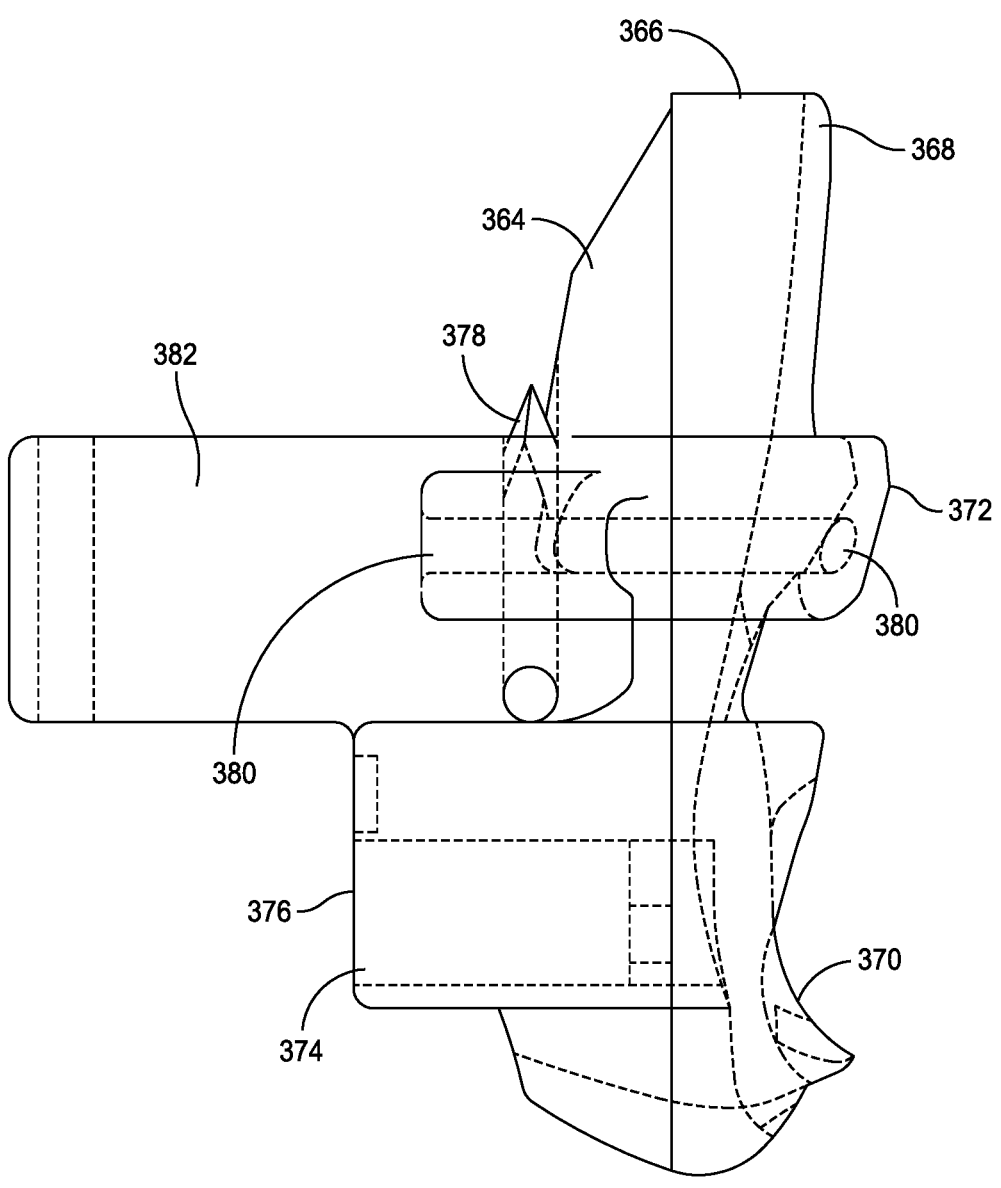

Schematics of a cross-sectional side view of devices are illustrated in FIGS. 60-63 and depict standard section 364 and patient-specific section 366 coupled together and having patient-specific surfaces 368, 370, 372. As shown in FIG. 60 sleeve 374 is positioned in standard section 364 with opening 376 extending from standard section 364 into patient-specific section 366. Metal locator 378 is positioned such that it may be used as a reference during use, for example during imaging. In some instances, metal locators may include pins and/or wires (e.g., k-wires) that are positioned in the device during a surgical procedure. Tunnels 380 in sections 364, 366 are present to position pins during use. For example, tunnel 380 may be used to access bone with pins and/or instruments.

Figure 61:
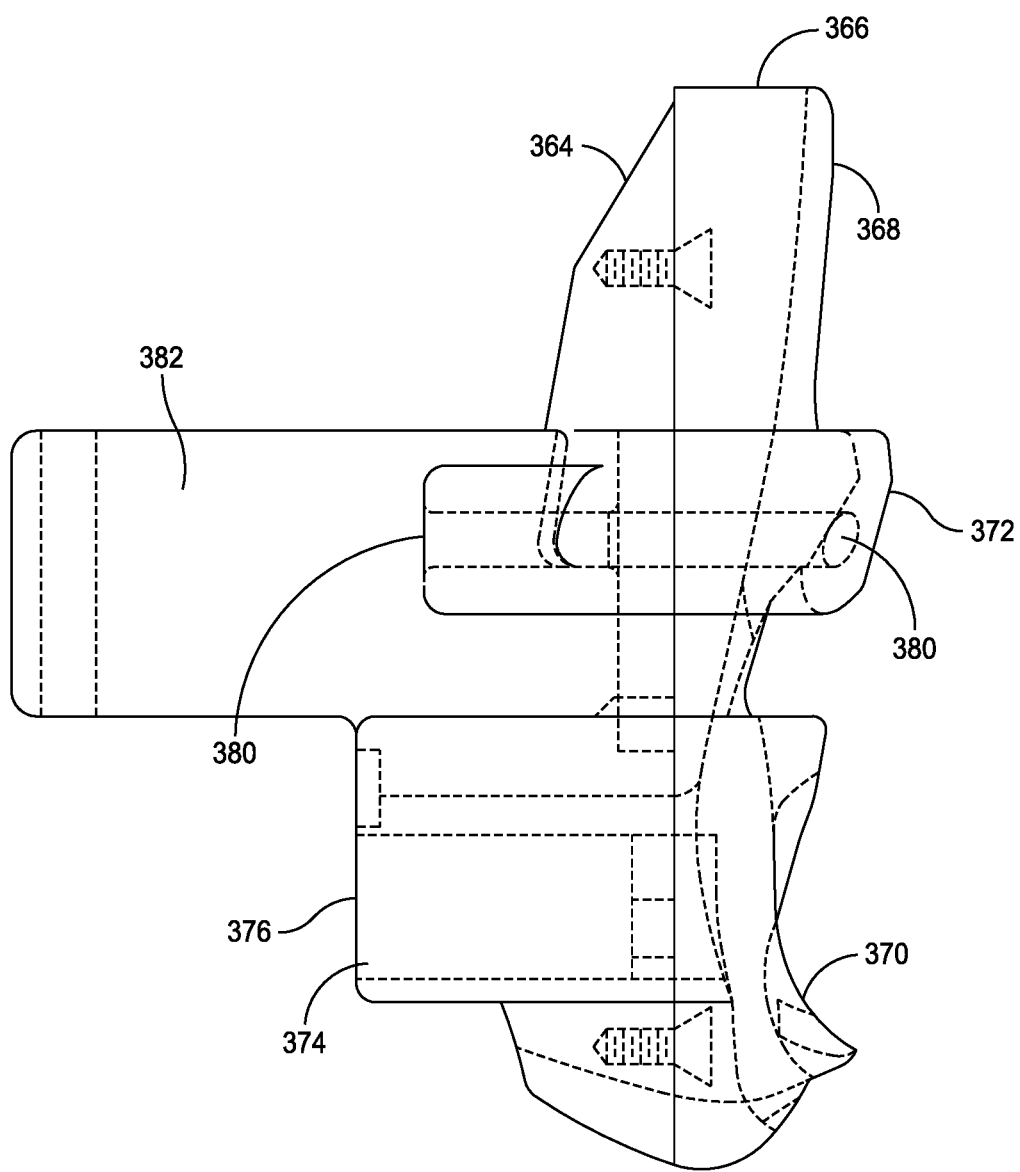
Figure 62:
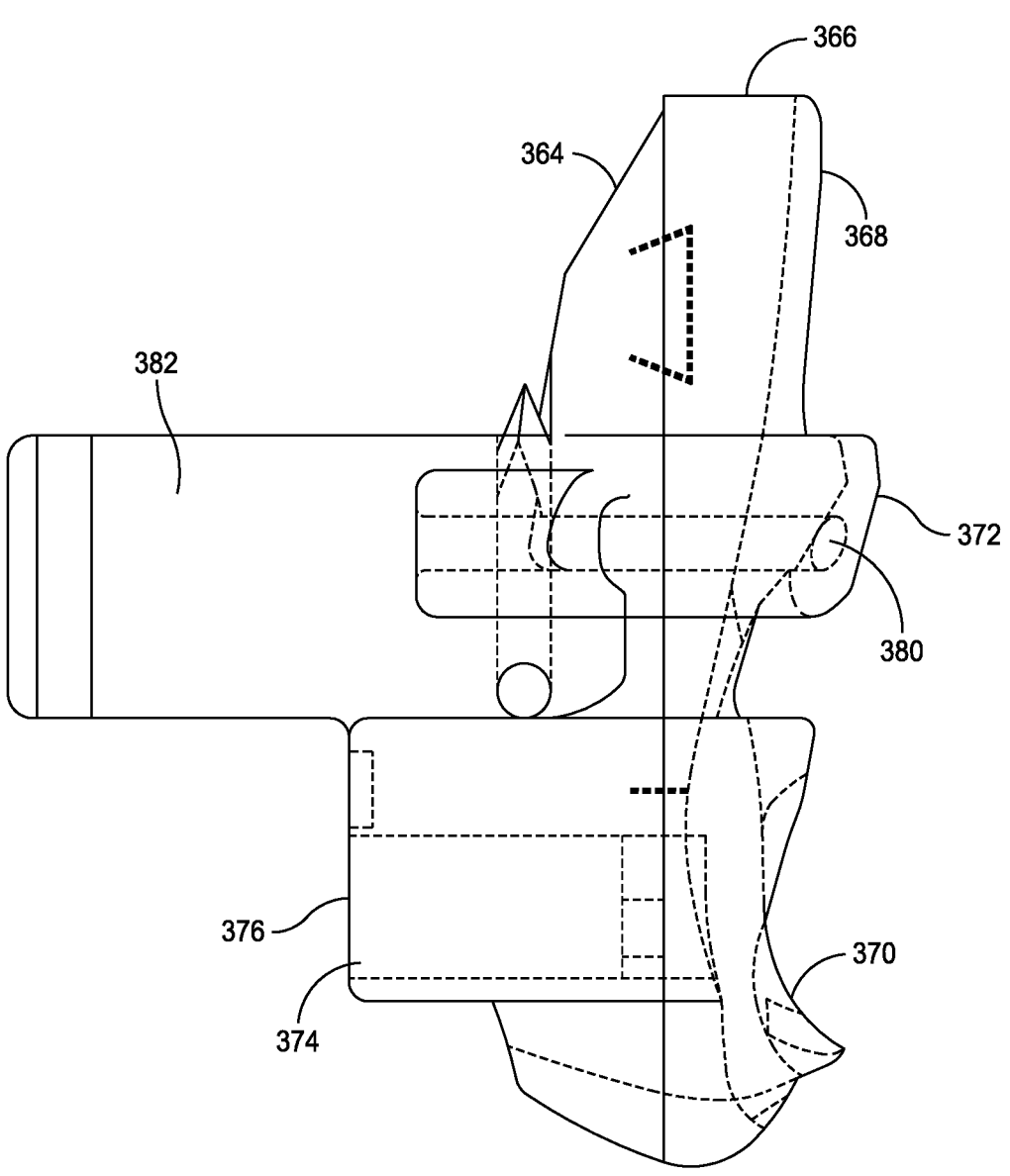
Figure 63:
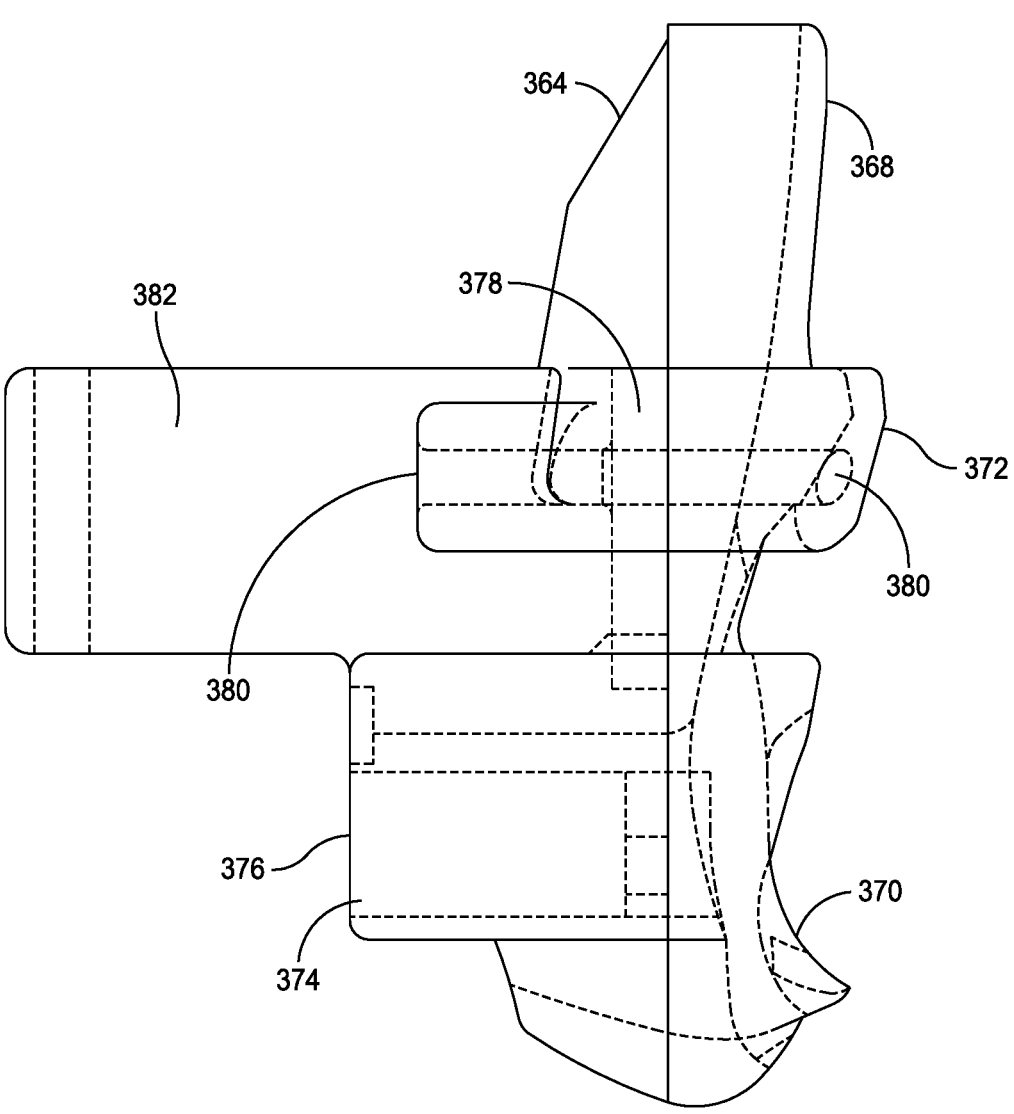

Devices may be formed from a patient-specific component and a standard body component that coupled in a manner that allows them to permanently coupled or temporarily coupled, for example, the standard body component may be separated from the patient-specific component such that the standard body component may be reused. In some instances, the patient-specific component and the standard body component may be affixed permanently to each other during an assembly manufacturing step using couplers including, but not limited to fasteners, adhesives such as glue, etc. and combinations thereof. FIGS. 61-62 depict different methods of coupling the sections together, namely screws and staples, respectively.

Resection guides shown in FIGS. 60-63 include body sections 364, 366 having indicators 382 on one or more surfaces. Indicators may be used to confirm that the proper device is being used prior to and/or during surgery. For example, a patient-specific section of the device body may include one or more indicators to identify orientation of the device and/or the patient-specific surface that should be used to engage the target area.

Body sections of devices may be formed using injection molding, insert molding, overmolding, additive manufacturing such as 3D printing, for example, stereolithography (SLA), laser sintering, selective laser sintering (SLS), fused deposition modeling (FDM), digital light process (DLP), multi-jet fusion (MJF), polyjet, direct metal laser sintering (DMLS), electron beam melting (EBM) and/or combinations thereof. In some instances, body sections may be formed from the same materials using similar methods of manufacturing. In alternate embodiments, body sections may be formed of differing materials and/or formed using different methods. In particular, materials used in 3D printed sections of devices and/or elements may be selected based on characteristics of the materials such as compatibility with in vivo use, strength such as yield strength and/or ultimate strength, Young's modulus, creep/viscoelasticity, fatigue, resistance to abrasive wear, magnetism, surface roughness, reflectivity, refractivity, compatibility with post-processing procedures such as cleaning, and sterilization and/or other properties of interest. Materials of interest may include, but are not limited to plastics such as polycarbonate (PC), polyethylene (PE), methyl methacrylate (MMA), polymethyl methacrylate (PMMA), polyether ether ketone (PEEK), poly ether ketone ketone (PEKK), acrylonitrile butadiene styrene (ABS), polylactic acid (PLA), hydroxyapatite, ceramics such as calcium phosphate ceramics, carbon-based materials such as carbon fiber, graphite, graphene, metals such as titanium, tantalum, and niobium, alloys like stainless steel, cobalt-chromium alloys, titanium alloys, aluminum alloys, and/or nitinol For example, some devices may include sections of and/or complete bodies and/or inserts formed from 3D printed metal and plastic.

In an embodiment, a device may be formed using injection molding that includes one or more surfaces that are configured to conform to a target surface on a bone of a specific patient. Patients may be evaluated prior to surgery using various imaging methods including, but not limited to three dimensional (3D) medical imaging such as computer tomography (CT), magnetic resonance imaging (MRI), and combinations thereof.

Images and/or other patient-specific data (i.e., patient identifiers, indicators of what part of the surgery the part should be utilized) may be positioned on one or more surfaces of the device. For example, predetermined patient-specific data may positioned on a surface of a device during formation, for example, molding and/or additive manufacturing and/or afterwards using an embossing process, an engraving process, or the like. Patient-specific data on one or more surfaces of a device may be used to confirm that the selected device has a surface that conforms to a target area of the patient undergoing a procedure.

Elements of the device such as inserts, liners, screws, staples, pins and/or sleeves may be formed using various manufacturing methods. For example, elements may be formed by standard manufacturing methods known in the art including, but not limited to metal fabrication methods, injection molding, insert molding, overmolding, additive manufacturing such as 3D printing, for example, stereolithography (SLA), laser sintering, selective laser sintering (SLS), fused deposition modeling (FDM), digital light process (DLP), multi-jet fusion (MJF), polyjet, direct metal laser sintering (DMLS), electron beam melting (EBM) and/or combinations thereof.

Figure 64:
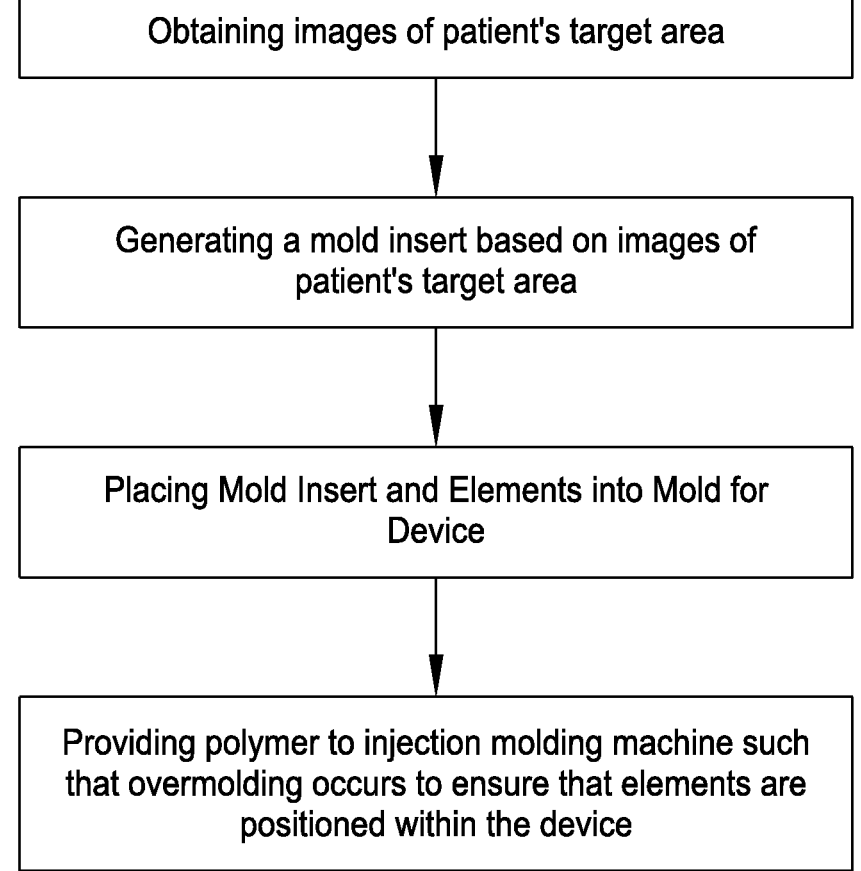

As outlined in FIG. 64 methods of forming a custom tool, instrument, and/or device having a patient-specific surface may include obtaining images of the patient's target area, generating a mold insert based on the images of the patient's target area, placing the mold insert and/or elements like sleeves into a mold for the device in predetermined positions specific to the patient and/or the procedure within the mold, and providing a preselected material to an injection molding machine to form the device. For example, a preselected polymer material may be provided to an injection molding machine to form a custom tool, instrument, device, and/or a portion thereof.

Obtaining images of the patient may include imaging by a computer tomography scanner (CT), magnetic resonance imaging machine (MRI), or the like medical imaging technology. For example, a CT or MRI scanned image or series of images may be taken of a patient's knee, shoulder, elbow, or ankle. In particular, when using images for an ankle surgery it may be helpful to include images of the limb from the pelvis and/or the foot. Any CT and/or MRI scanned image data may be converted to a solid computer model of the lower limb often including the pelvis, femur, patella, tibia, or foot to determine implant alignment, type and sizing using specialized modeling methods that are often embodied in computer software. Computer generated solid models that are derived from CT and/or MRI scan image data will often include precise and accurate information regarding the surface contours surrounding the structures that have been imaged, e.g., the surface topography (e.g., the location, shape, size and distribution of surface features such as concavities and prominences or the like) of the bones and/or contour of fascia that have been imaged.

Figure 65:
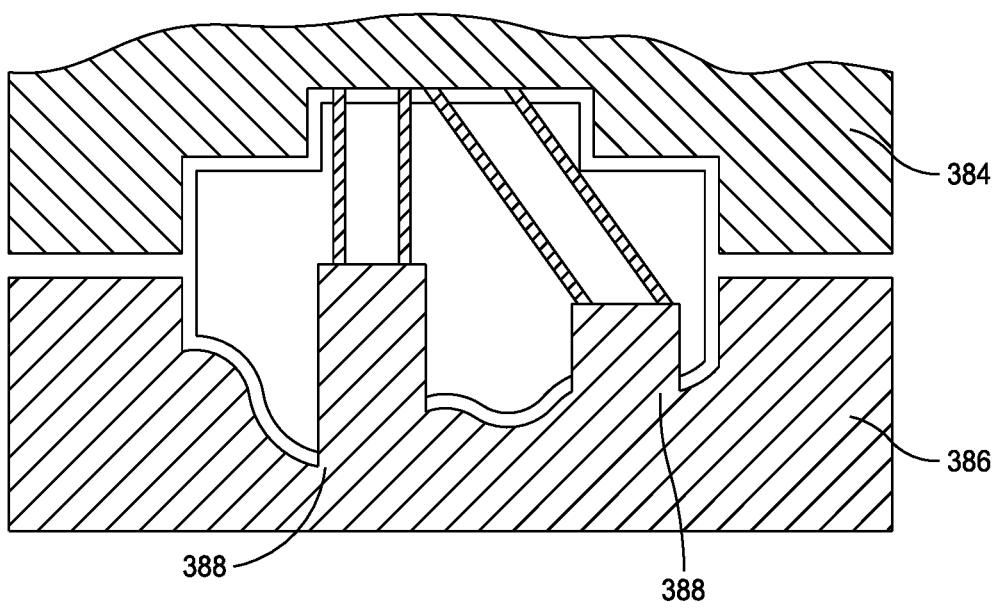

Data derived from the analysis described above may be used form a mold insert using additive manufacturing such as 3D printing and/or molding. As shown in FIG. 65, molds 384, 386 include standard mold 384 and patient-specific mold 386 having patient-specific surface 388. Molds may include locations to position elements within a device or an instrument as required for a patient and/or surgical procedure.

Figure 66:
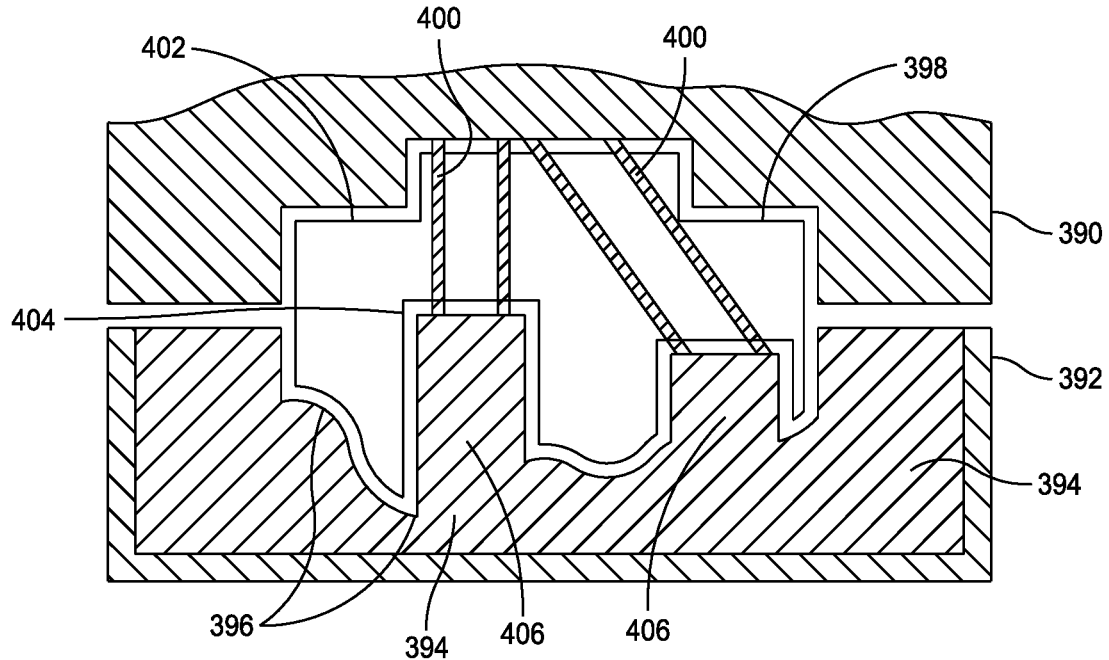

Using traditionally-formed custom molds for each patient may be costly, if not cost prohibitive in some instances. Thus, alternative manufacturing methods, such as multi-modal manufacturing may be used to meet the needs of customization while trying to control costs of production. In particular, mold inserts may be used to create custom objects using standard molds while reducing cost of production. For example, a 3D printed mold insert may be combined with standard molds to form a device and/or instrument having a patient-specific surface that conforms to the surface contours of a target area. As shown in FIG. 66, standard molds 390, 392 are used in combination with mold insert 394 having patient-specific surface to form device 398. Further, as illustrated in FIG. 66 are sleeves 400 are positioned proximate instrument engaging surface 402. Sleeves may provide an open channel that extends from the instrument-engaging surface to the opening, which extends to a patient specific surface. As shown in FIG. 66, sleeves 400 extend from instrument engaging surface 402 to openings 404. Thus, mold insert 394 includes projections 406 to define at least a portion of openings 404. In some embodiments, sleeves may extend the full length of the intended opening. Alternately, openings may be unlined in some instances.

Devices, as described herein, may include elements preselected based on the requirements for a specific surgical procedure, requirements due to patient, and/or compatibility with instruments. For example, elements of interest may include, but are not limited to metal elements such as sleeves (e.g., cut sleeves, sleeves of varying geometries such hollow oval prisms or other shapes), pins, BBs, cylinders (e.g., cannulated cylinders), fasteners such as screws, staples and/or other elements specific to a surgical procedure. Elements, in particular drill and/or cut sleeves may be chosen specifically based on the requirements for a surgical procedure, requirements due to patient, and/or compatibility with instruments.

During manufacturing of such a device, elements may be inserted into the molds in predetermined locations and/or orientations that depend on the type of surgery to be performed, the geometry of a patient's anatomy, and/or target surfaces, for example, surfaces of bone. In some instances, these elements may be metal inserts including, but not limited to drill sleeves such as cannulated cylinders, cut sleeves such as hollow oval prisms and/or other geometric shapes, metal cylinders, pins, spheres, pellets, BBs, labels, etc. Customization of a device may include selecting elements such as elements based on a position of use in vivo, geometry of the patient, surgical procedure, types of instruments to be used, for example, a blade or resection instrument.

Figure 67:
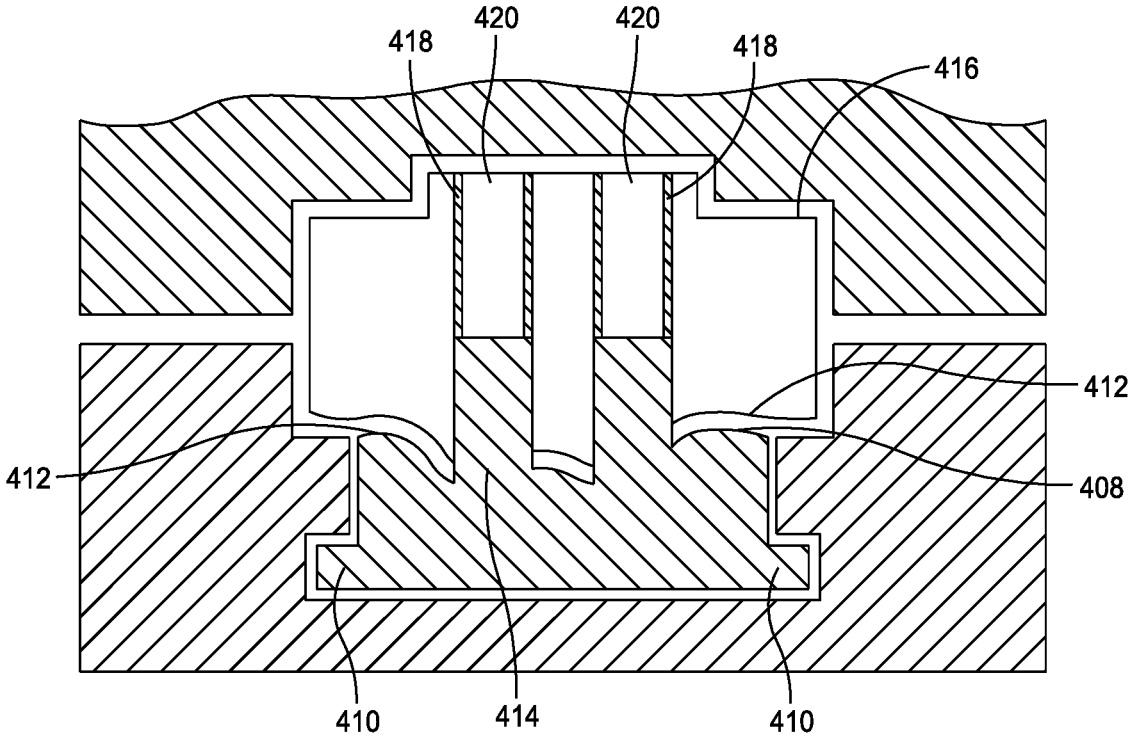
Figure 68:
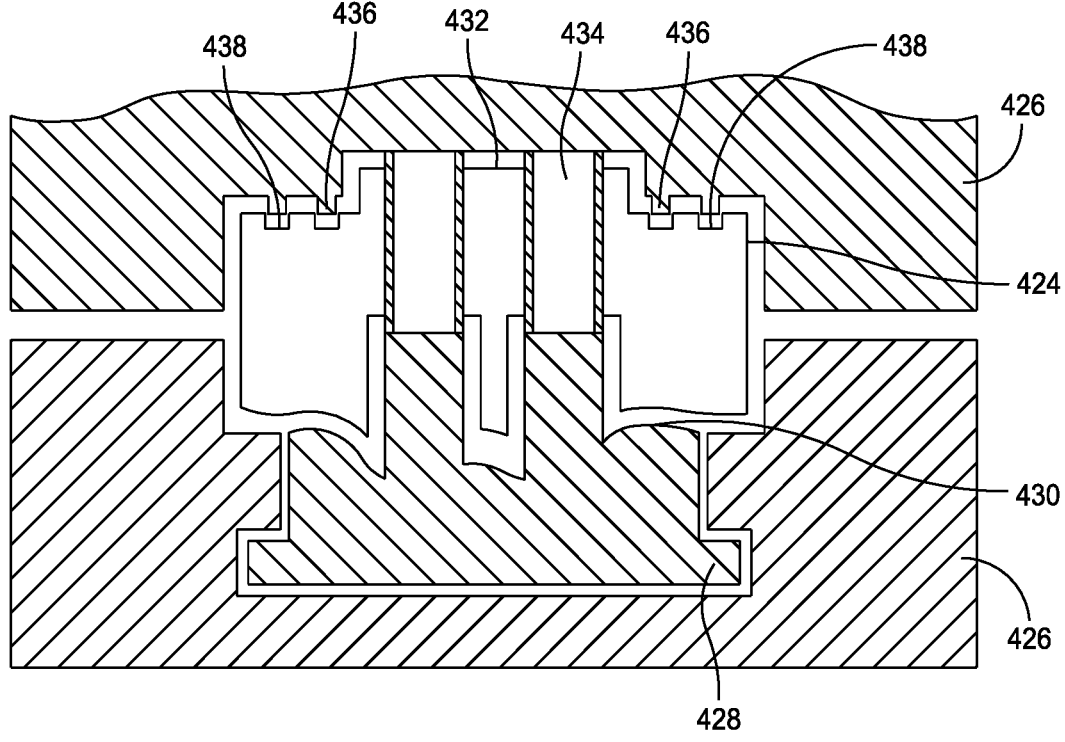

Molds and mold inserts may include shapes that form openings, channels and/or specific structures selected for a particular patient and/or procedure. As shown in FIG. 67, mold insert 408 includes engaging member 410 and target area surface 412, as well as projections 414. Projections may be used to form channels in the finished device 416 that are proximate sleeves 418. In the finished device, channels 420 extend through device 416 and sleeves 418 therein such that during use either an instrument and/or member may uses channels to access target areas, for example, bone surfaces. As depicted in FIGS. 67-68, device 416 includes patient-engaging surface 422 that conforms to contour of patient's region of interest on one side and the opposite surface having a contour that engages instruments of interest. FIG. 68 depicts device 424 for use in orthopedic surgery positioned within mold 426 that includes a mold insert 428 having patient-specific surface 430, instrument-engaging surface 432 of mold 426, and sleeves 434 positioned within device 424.

In some instances, portions of devices may include labels, images, indicators, such as those indicating patient, type of usage, for example, single use, multi-use, surfaces (e.g., instrument-engaging surfaces, patient-specific surfaces), side, measurements, etc. FIG. 68 shows mold 426 with indicator projection 436 such that indicator 438 forms on device 424. Indicator projection may include the negative image of the desired indicator.

Matching surfaces of a device to a patient, in particular, to the natural anatomical surface of a patient's bone may ensure a better fit during use, for example during surgery and/or use in vivo thereafter. For example, in a multi-sectional device components of the device may include a patient-specific component having a negative surface from the patient's target bone region on a bone-engaging surface and a coupling surface designed to be coupled to a standard body component. In some instances, the bone-engaging surface may be positioned on a surface opposite the coupling surface.

Figure 69:
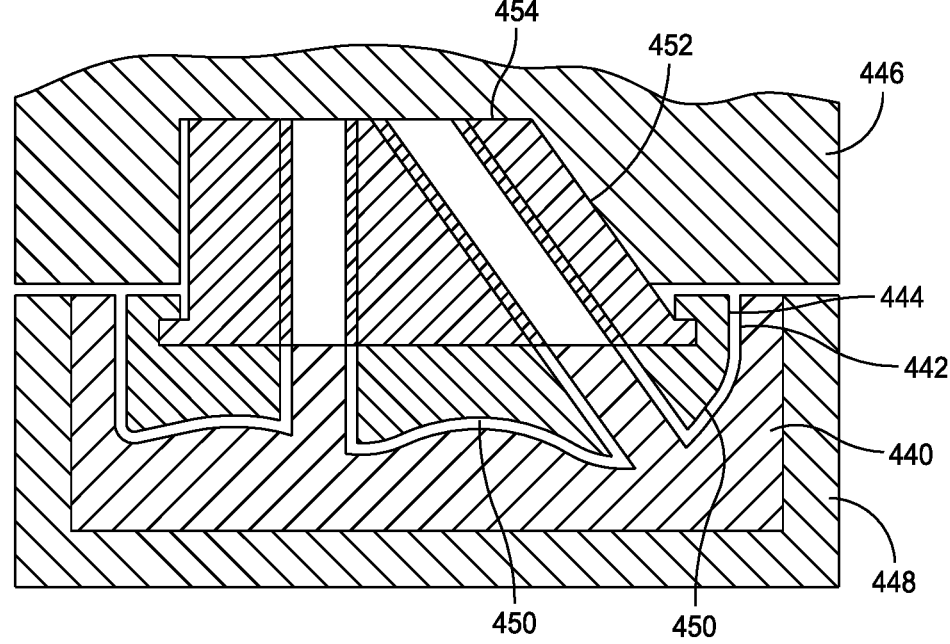

As shown in FIG. 69 mold insert 440 includes indicator projection 442 having the negative image of predetermined indicator 444 formed during molding on device 446. Predetermined indicators may include patient identifying information, orientation information, or the like. Mold insert 440 is positioned in mold 448 such that device 446 is formed with patient-specific surface 450. Mold 452 includes instrument contour 454 such that during molding device 446 is formed having the negative image of an instrument or tool.

Figure 70:
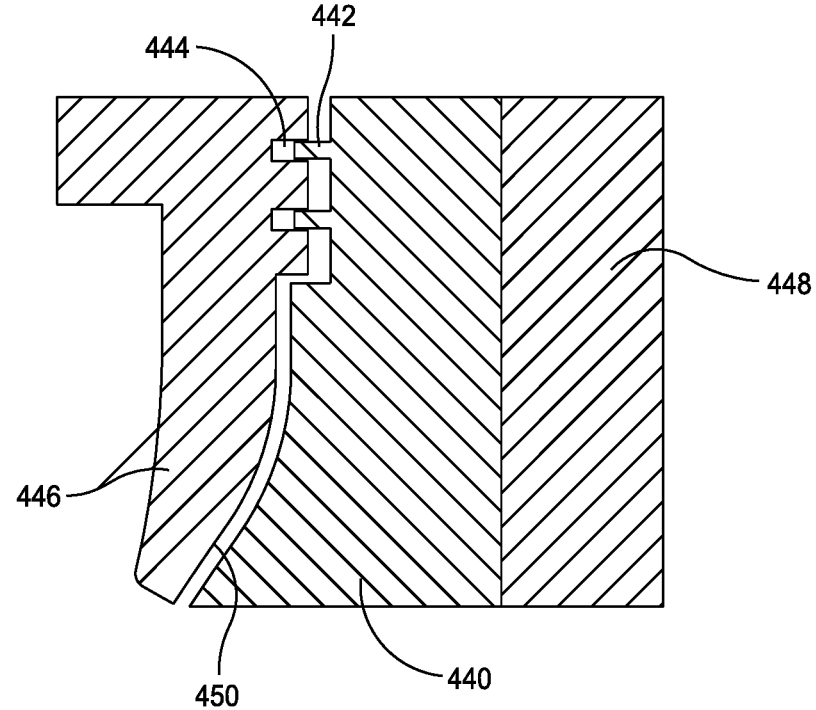

An enlarged version of the interface of device 446, mold insert 440, and mold 448 is depicted in FIG. 70. Indicator 444 on device is formed during molding by indicator projection 442 on mold insert 442.

Figure 71:
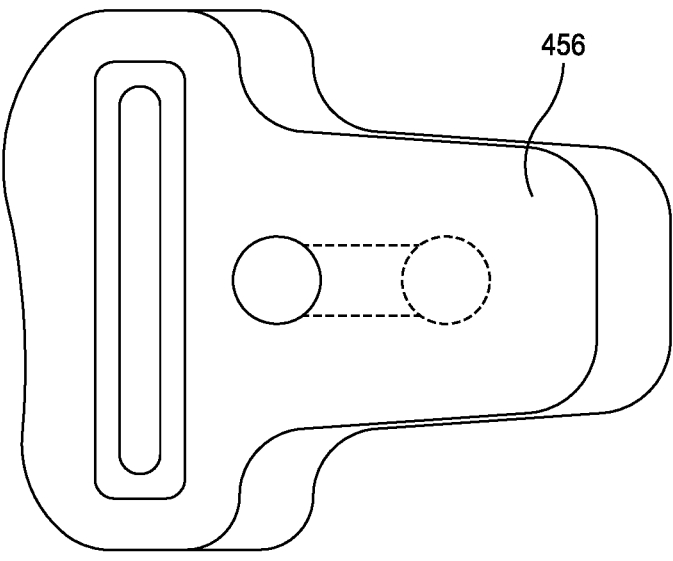

FIGS. 71-78 depict various views of hybrid devices that may benefit from a patient-specific surface. Hybrid devices may include multiple materials. For example, some embodiments may include a hybrid device including metal and plastic materials as shown in FIGS. 71-72. Components may be positioned after formation of the device by pressing the components into the device at predetermined locations. In some embodiments, components may be placed in device while the device is being formed through injection molding and/or 3D printing. Components may be placed in molds prior to forming the device using injection molding.

In particular, FIG. 72 depicts a schematic cross-sectional view of device 458 positioned proximate bone surface 460 having patient-specific surface 462, device engaging surface 464, and inserts 466 that extend from patient-specific surface 462 to device engaging surface 464.

In contrast, FIG. 73 depicts a cross-sectional view of device 468 for use in orthopedic surgery formed from multiple sections, for example, patient-specific section 470 and instrument-engaging section 472. Instrument-engaging section may be a standard design and in some cases mass-produced so that it can be used with various patient-specific sections. For example, as shown in FIG. 73, instrument-engaging section 472 includes sleeves 474, 478 and positioner element 476. Positioner element may be constructed from a radiopaque material to aid in positioning the device during use. Sleeve 474 extends through the instrument-engaging section 472 to opening 480 in the patient-specific section 470 thus providing access through the coupled sections during use. As shown patient-specific section and standard section 472 having instrument-engaging surface are coupled together during use.

In some instances, standard sections, for example, instrument-engaging sections may be reuseable. Thus, sections 470, 472 may be releaseably coupled together such that after use the sections may be decoupled. In some instances, sections may be coupled together using any method known in the art including, but not limited to friction fits such as joints, for example, dado joints, tongue and groove joints, rabbit joints, mortise and tenon joints, box joints, biscuit joints, dovetail joints, etc., fasteners such as screws, staples, pins (e.g., cross-hair pins), plates, adhesives such as glue, and/or combinations thereof.

FIG. 74 depicts a front perspective view of a resection guide that includes instrument-engaging section, patient-specific section 482, and components such as liners 484 positioned in openings 486 and/or slots 488. Configurations of the openings and/or slots may be selected based on the type of surgical procedure, the anatomy of the patient, instruments to be used, etc. For examples, instruments that may be considered when designing a device, openings, and/or slots positioned therein may include one or more instruments such as saws, drills, burrs, blades, electrocautery devices, lasers, rasps, etc.

FIG. 75 depicts a front perspective view of resection guide 490. Resection guides may include features that enable connection to one or more of a variety of instruments depending on the needs or step of a surgical procedure. For example, resection guide 490 includes features like openings 492, such as pin holes 494, and slots 496 to engage and/or guide cutting instruments. In particular, a resection device may include slots configured to guide saw blades such that a predetermined section of bone is contacted and/or removed.

Components of a device may be selected to create a customized device for use in surgery based on a number of factors including, but not limited to size, configurations, materials, radiolucency, procedures to be used, instruments used, etc. FIG. 76 depicts a front view of a resection guide selected for use in surgery. Instrument-engaging section 498 is facing outwards with a portion of patient-specific section 500 shown around the outside of device 502. As shown, lining elements 504 are positioned within openings 506, 508 extending through instrument-engaging section 498. A cross-sectional view of device 520 is depicted in FIG. 77 and includes patient-specific surface 510 on patient-engaging section 512 and standard section 514 having device engaging surface 516 and inserts 518 positioned within the standard section. To form such a standard component inserts may be placed in a mold and then an overmolding method may be used to form the standard section around the inserts.

FIG. 78 depicts a front view of a resection guide depicted in FIG. 77. Instrument-engaging portion 522 is depicted facing out and patient-engaging section 524 is positioned on the opposing face of device 520. Portions of the patient-engaging section 524 are visible as they extend beyond instrument-engaging section 522.

The disclosed embodiments provide for devices including devices in modular systems for enabling secure connections to a specific patient's bones. Accurate and secure placement of devices, tools and/or instruments may reduce risk to patients. For example, utilizing patient-specific surfaces on resection guides and/or resection guide locators while providing a variety of connection options for easily placing tools and/or cutting guides may reduce risk by reducing time necessary to complete procedures and/o increasing stability of connections during procedures.

Disclosed embodiments may be used in a variety of applications and methods, including surgical methods for operating on a patient, and, in particular, a joint (e.g., an ankle joint, elbow joint, knee joint, shoulder joint, etc.). The disclosed components may include features for positioning guide openings for receiving tools (e.g., saws, drills, drivers, etc.) for performing steps of a procedure.

In one example, a method includes positioning a resection guide locator having one or more patient-specific surfaces with respect to a joint. For example, the resection guide locator may be positioned with respect to a first bone (e.g., tibia) of an ankle joint. A first component, such as resection guide may be attached to the resection guide locator, such as by inserting the resection guide into the receptacle of the resection guide locator. A first operative step may be performed using the resection guide, such as a resection cut of the tibia. With the resection guide locator and the first component in place, a second component, such as a second resection guide, may be attached. For example, a second resection guide may be attached to the receptacle of the first resection guide, and a second operative step performed. For example, a talar resection guide may be attached to a first resection guide and a talar resection step performed. In another embodiment, the second component may be a corner protector peg attached to the first resection guide. In some embodiments, components may be assembled on the patient, or may be pre-assembled prior to positioning with respect to the patient. The disclosed embodiments are thus applicable as a modular system providing a user with multiple options for performing a procedure.

In another embodiment, a medical device is provided having a resection guide locator with a mount body having a conformal surface that is shaped to be complementary to a natural anatomical surface of a patient bone. The resection guide locator also defines a mount receptacle. In addition, a resection guide is provided having a guide body with a shape configured to fit within the mount receptacle to attach the resection guide to the resection guide locator. A guide receptacle is included with at least one opening for receiving a tool during an operation on the patient's bone. At least one corner protector peg is provided that is configured to be inserted through the guide receptacle for further guiding the tool during the operation. The corner protector pegs may be cannulated. The device may be configured so that the guide receptacle incudes at least one enlarged opening for receiving a corner protector peg, where the at least one opening defines a plurality of interconnected slotted channels and the at least one enlarged opening defines a first hole formed at an intersection of two of the slot channels. Also, the at least one corner protector peg may include a groove along the peg to limit a distance of travel of the tool, and the at least one corner protector peg may further include a locking shoulder configured to receive a portion of the resection guide locator. In some embodiments, the at least one corner protector peg includes a retention feature for inhibiting removal of the corner protector peg. A retention feature such as a spring clip may also be included with a variety of embodiments. In further embodiments, the retention feature is a projection on a shaft of the corner protector peg configured to be inserted through a slot in the resection guide with the corner protector peg being rotatable after the projection is inserted through the slot to inhibit removal. The device may also include a cutting guide having an attachment feature configured to be inserted into the open end of the cannulated corner protector pegs.

In a further embodiment, a medical device is provided that includes a resection guide locator having a mount body with a conformal surface that is shaped to be complementary to a natural anatomical surface of a patient's bone. The resection guide locator may also define a mount receptacle for receiving a resection guide. A plurality of stationary through-bores may be located adjacent to and defined outside of the mount receptacle with each configured to receive a pin. The plurality of through-bores each have open ends that are aligned with a path into gutters formed on opposing sides of the patient's bone. A resection guide may be provided that is configured to be inserted into the mount receptacle. The resection guide often defines at least one opening for receiving a tool during a surgical procedure. Often, the one or more surfaces of the mount receptacle and/or the resection guide are tapered to accommodate a press fit. In some versions of the invention, the mount body further includes a retention mechanism configured to attach the resection guide to the resection guide locator. Often, the retention mechanism utilizes a spring clip configured to retain the resection guide in the mount receptacle.

Additional methods are provided for a surgical procedure on a joint having at least a first bone and a second bone, where a resection guide locator is positioned with respect to the joint. A first component is attached to the resection guide locator, a second component is attached to the first component, and at least one operative step is performed on at least one of the first bone and the second bone, that is guided by the first component and the second component. In some embodiments, the first component is a first resection guide or the second component is a second resection guide. Additionally, the second component may be a corner protector peg. In some cases, the first component is attached to the resection guide locator by engaging a retention mechanism configured to hold the first component to the resection guide locator. In addition, the second component may be attached to the first component by engaging a retention mechanism configured to hold the first component to the resection guide locator.

Advantageously, the invention also includes a method for forming a device having a patient-specific surface in which data is acquired for a target area patient's anatomy and then forming at least a portion of a device based on the acquired patient data. For example, at least a portion of the device having a patient-specific surface may be formed using additive manufacturing techniques. In some embodiments, a procedure for forming device having a patient-specific surface includes acquisition of data regarding a target area of the patient's anatomy, forming at least a portion of a device based on the acquired patient data using at least one of additive manufacturing techniques or injection molding, then coupling the patient-specific section to a standard section of the device. In other inventive methods of forming a device having a patient-specific surface using data acquired from a target area of a patient's anatomy a mold is formed having at least one patient-specific surface that mimics at least a portion of a surface of the patient's target area, and then forming at least a portion of the device based on the acquired patient data using injection molding so as to allow for the coupling of the patient-specific section to a standard section of the device. In some embodiments a mold insert is formed using the acquired patient data having at least one contour of the patient's target area.

In a further alternative embodiment of the invention, a device having a patient-specific surface is provided that includes a body having at least one patient-specific surface, an instrument-engaging surface positioned opposite the patient-specific surface on the body, one or more openings in the body extending from the at least one patient-specific surface to the instrument-engaging surface, and an insert positioned in at least a portion of the body. At least a portion of the body may be formed from a radiolucent material. In a further embodiment, the body may include a patient-specific section having a patient-specific surface, an instrument-engaging section including an instrument-engaging surface coupled to the patient-specific section such that the instrument-engaging surface is positioned substantially opposite a least a portion of the patient-specific surface when the sections are coupled to form the body. In other embodiments, one or more inserts are provided that may be positioned at at least a portion of the body formed from a radiolucent material so that the insert is coupled to the body by a using an injection molding process such that the insert is fixedly positioned in the body.

In a yet further embodiment, a device is provided having a patient-specific surface with a body formed from a radiolucent material, a patient-specific section having a patient-engaging surface, an instrument-engaging section having an instrument-engaging surface positioned opposite the patient-specific surface on the body, and one or more openings in the body extending from the portion having at least one patient-specific surface to the instrument-engaging surface. The one or more openings may be lined. Alternatively, the device having a patient-specific surface may include a body with a patient-specific section formed from a first material having a patient-engaging surface, an instrument-engaging section formed from a second material having an instrument-engaging surface positioned opposite the patient-specific surface on the body, and one or more openings in the body extending from the at least one patient-specific surface to the instrument-engaging surface.

In further manufacturing methods, a standard guide body is positioned in a printing cavity of an additive manufacturing machine, where the geometry of the standard guide body is not patient specific. In this way, a patient match body is formed inn the printing cavity of the additive manufacturing machine such that the patient match body is affixed to the standard guide body, where the patient match body includes at least one surface that is adapted to match a surface topology of a bone. Some embodiments include positioning at least one sleeve in the printing cavity of the additive manufacturing machine, so that forming the patient match body includes forming the patient match body around the at least one sleeve such that the at least one sleeve extends at least partially through the standard guide body and the patient match body.

In other aspects of the invention, a surgical guide is provided that includes a patient match body having a surface that is complementary to a surface topology of a bone, the patient match body defining a first aperture, a standard guide body fixedly coupled to the patient match body, the standard guide body defining a second aperture, the second aperture aligned with the first aperture, and a sleeve extending through the first aperture and the second aperture. In some versions of the invention, the sleeve is radiopaque and both the patient match body and the standard guide body are radiolucent. In other versions of the invention, the patient match body includes a pocket and wherein the second body is at least partially disposed in the pocket.

Although the invention has been described in terms of exemplary embodiments, it is not limited thereto. Rather, the appended claims should be construed broadly, to include other variants and embodiments of the invention, which can be made by those skilled in the art without departing from the scope and range of equivalents of the invention.

What is claimed is:

1. A device having a patient-specific surface comprising:
a body having at least one patient-specific surface;
an instrument-engaging surface positioned opposite the patient-specific surface on the body;
one or more openings in the body extending from the at least one patient-specific surface to the instrument-engaging surface;
one or more inserts positioned in the body, a first insert of the one or more inserts comprise at least a radio-opaque sphere, the radio-opaque sphere being fully encapsulated within the body and positioned at a predetermined offset relative to at least one of the openings;
a reference component attached to the body and configured to provide an alignment check in two or more dimensions, including:
a post having a first side and a second side,
a rear portion on the first side of the post, and
a front portion on a second side of the post opposing the first side of the post, and
wherein the rear portion and the front portion together present a pattern when viewed from a straight-on direction so that the reference component provides the alignment check in two or more dimensions, and wherein the rear portion and the front portion are laterally registered about the post and are axially spaced by a fixed gap such that the pattern is formed by superposition in the straight-on direction and de-registers when viewed from a non-orthogonal direction; and
wherein at least a portion of the body is formed from a radiolucent material.

2. The device of claim 1 wherein a second insert of the one or more inserts comprise at least one of an alignment feature, an insert, a metallic component, a liner, a radio-opaque sphere, a cluster of radio-opaque spheres, a cutting sleeve, and a visualization aid.

3. The device of claim 2 further comprising at least one of one or more inserts positioned in at least a portion of the one or more openings in the body.

4. The device of claim 1 further comprising at least one liner positioned in at least a portion of the one or more openings.

5. The device of claim 1 wherein:
the at least one of the one or more inserts are coupled to the body using an injection molding process or additive manufacturing process such that the at least one insert is fixedly positioned in the body.

6. The device of claim 1 wherein the device comprises a resection guide.

7. The device of claim 1 further comprising at least one respective insert of the one or more inserts positioned within at least a portion of the body, the respective insert formed from a radio-opaque material.

8. The device of claim 1, wherein a second insert of the one or more inserts comprises a saw blade slot.

9. A resection guide comprising:

a body having at least one a bone engagement patient-specific surface;

an instrument-engaging surface positioned opposite the at least one a bone engagement patient-specific surface on the body, with two or more guide slots in a central portion of the body extending from the at least one a bone engagement patient-specific surface to the instrument-engaging surface;

a reference component configured to provide an alignment check in two or more dimensions, and attached to the body, including:

a post having a first side and a second side, a rear portion on the first side of the post, and a front portion on a second side of the post opposing the first side of the post;

wherein the rear portion and the front portion together present a pattern when viewed from a straight-on direction so that the reference component provides the alignment check in two or more dimensions, and wherein the rear portion and the front portion are laterally registered about the post and are axially spaced by a fixed gap such that the pattern is formed by superposition in the straight-on direction and de-registers when viewed from a non-orthogonal direction; and at least one wing projection outwardly from the central portion of body and configured to receive one or more k-wires to anchor the body to a bone adjacent to a joint, wherein the body is adapted to be seated on the bone adjacent to the joint with the at least one a bone engagement patient-specific surface adapted to be engaging the bone adjacent to the joint.

* * * * *